(12) United States Patent
Vigne et al.

(10) Patent No.: US 6,911,199 B2
(45) Date of Patent: Jun. 28, 2005

(54) TARGETED ADENOVIRUS VECTORS FOR DELIVERY OF HETEROLOGOUS GENES

(75) Inventors: Emmanuelle Vigne, L'Hay-les-Roses (FR); Jean-Francois Dedieu, Paris (FR); Martine Latta, Charenton le Pont (FR); Patrice Yeh, Gif sur Yvette (FR); Michel Perricaudet, Ecrosnes (FR)

(73) Assignee: Aventis Pharma S.A., Antony Cedex (FR)

( * ) Notice: Subject to any disclaimer, the term of this patent is extended or adjusted under 35 U.S.C. 154(b) by 372 days.

(21) Appl. No.: 09/791,524

(22) Filed: Feb. 22, 2001

(65) Prior Publication Data

US 2003/0143209 A1 Jul. 31, 2003

Related U.S. Application Data

(63) Continuation of application No. PCT/IB99/01524, filed on Aug. 27, 1999.
(60) Provisional application No. 60/098,028, filed on Aug. 27, 1998.

(51) Int. Cl.$^7$ .......................... A61K 48/00; C12N 15/63
(52) U.S. Cl. ................... 424/93.2; 435/91.4; 435/320.1
(58) Field of Search .............................. 435/320.1, 91.4, 435/69.1, 325, 455; 424/93.2

(56) References Cited

U.S. PATENT DOCUMENTS

| | | | | |
|---|---|---|---|---|
| 5,846,782 A | * | 12/1998 | Wickham et al. | 435/697 |
| 5,980,886 A | * | 11/1999 | Kay | 424/93.21 |
| 6,120,765 A | * | 9/2000 | Hibino | 424/96.43 |
| 6,127,525 A | * | 10/2000 | Crystal | 530/388.22 |
| 6,287,857 B1 | * | 9/2001 | O'Riordan et al. | 435/320.1 |

FOREIGN PATENT DOCUMENTS

| | | |
|---|---|---|
| WO | WO 95/05201 | 2/1995 |
| WO | WO 95/26412 | 10/1995 |
| WO | WO 96/26281 | 8/1996 |
| WO | WO 97/20051 | 6/1997 |
| WO | WO 98/07865 | 2/1998 |
| WO | WO 98/07877 | 2/1998 |
| WO | WO 98/40509 | 9/1998 |

OTHER PUBLICATIONS

Crompton J, Expression of a Foreign Epitope on the Surface of the Adenovirus Hexon, Journal of General Virology, GB, Society for General Microbiology, Reading, vol. 75, pp. 133–139.

Krasnykh Victor et al., Characterization of an Adenovirus Vector Containing a Heterologous Peptide Epitope in the HI Loop of the Fiber Knob, Journal of Virology, Mar. 1998, pp. 1844–1852.

Vigne Emmanuelle et al., RGD Inclusion in the Hexon Monomer Provides Adenovirus Type 5–Based Vectors with a Fiber Knob–Independent Pathway for Infection, Journal of Virology, Jun. 1999, vol. 73, No. 6, pp. 5156–5161.

Wickenham T J, Adenovirus Targeted to Heparan–containing Receptors Increases its Gene Delivery Efficiency to Multiple Cell Types, Biotechnology. The International Monthly for Industrial Biology, US, Nature Publishing Co., NY, vol. 14, No. 11, pp. 1570–1573.

* cited by examiner

*Primary Examiner*—Dave T. Nguyen
(74) *Attorney, Agent, or Firm*—Synnestvedt & Lechner LLP

(57) ABSTRACT

Modification of internal sites of the adenovirus fiber protein and hexon protein permit effective targeting of adenovirus vectors. Accessible sites to redirect adenovirus targeting were identified. The HVR5 loop of the hexon protein and the HI loop of the fiber protein (knob) were highly permissive for the insertion of foreign protein sequences, which apparently did not impact on the viability and productivity of corresponding viruses. Accessibility and functionality of the epitope strongly depend on the size of the neighboring spacers. Other results suggest that short targeting peptides can be effectively fused to the C-terminus of the fiber protein. In a specific embodiment, a series of adenovirus vectors modified at the HVR5 site, the fiber protein HI loop, or the fiber protein C-terminus to target urokinase-type plasminogen activator receptor bearing cells were prepared. Such vectors are particularly useful for targeting the vasculature, e.g., for gene therapy of cancers or cardiovascular conditions.

46 Claims, 15 Drawing Sheets

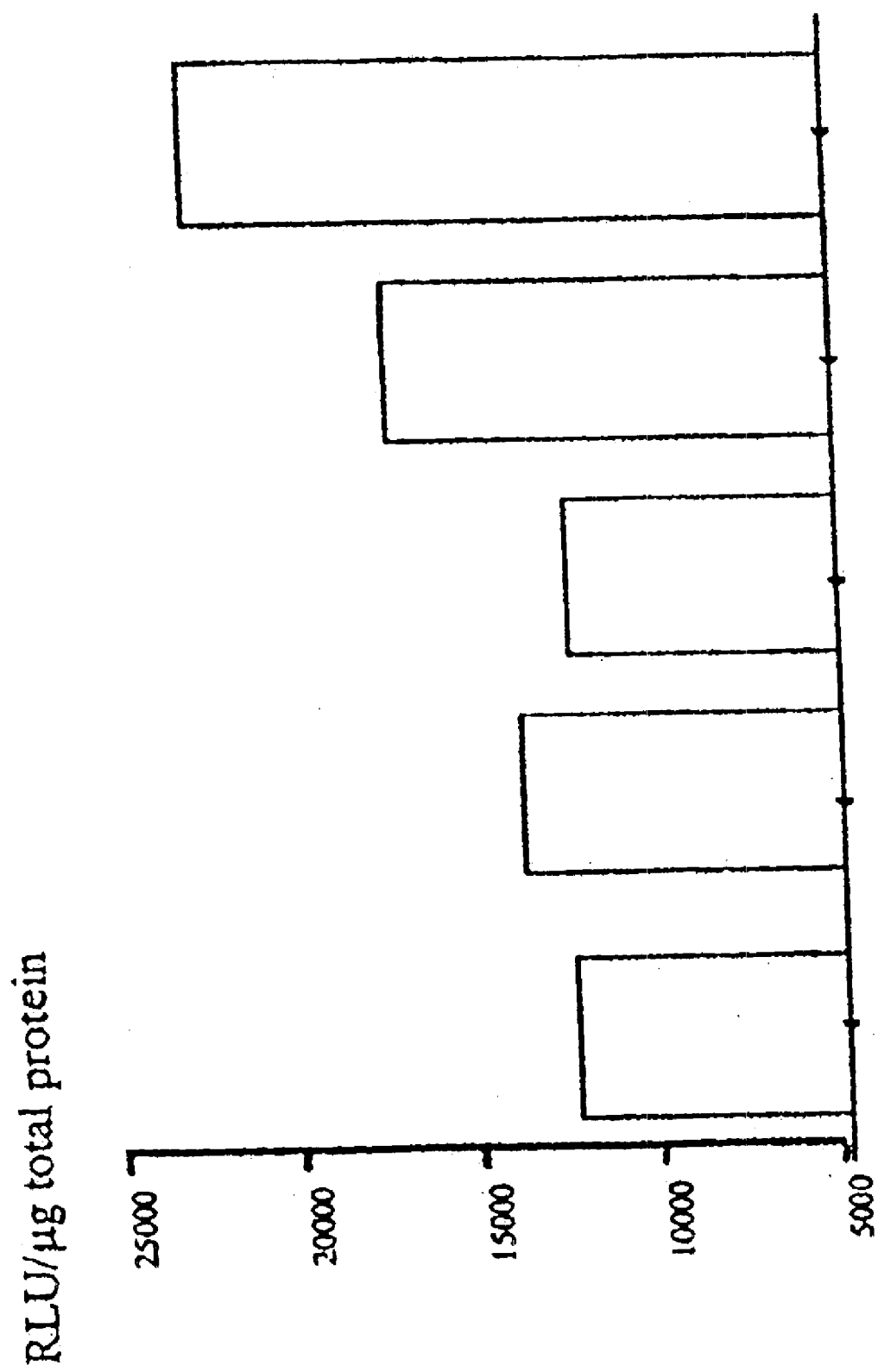

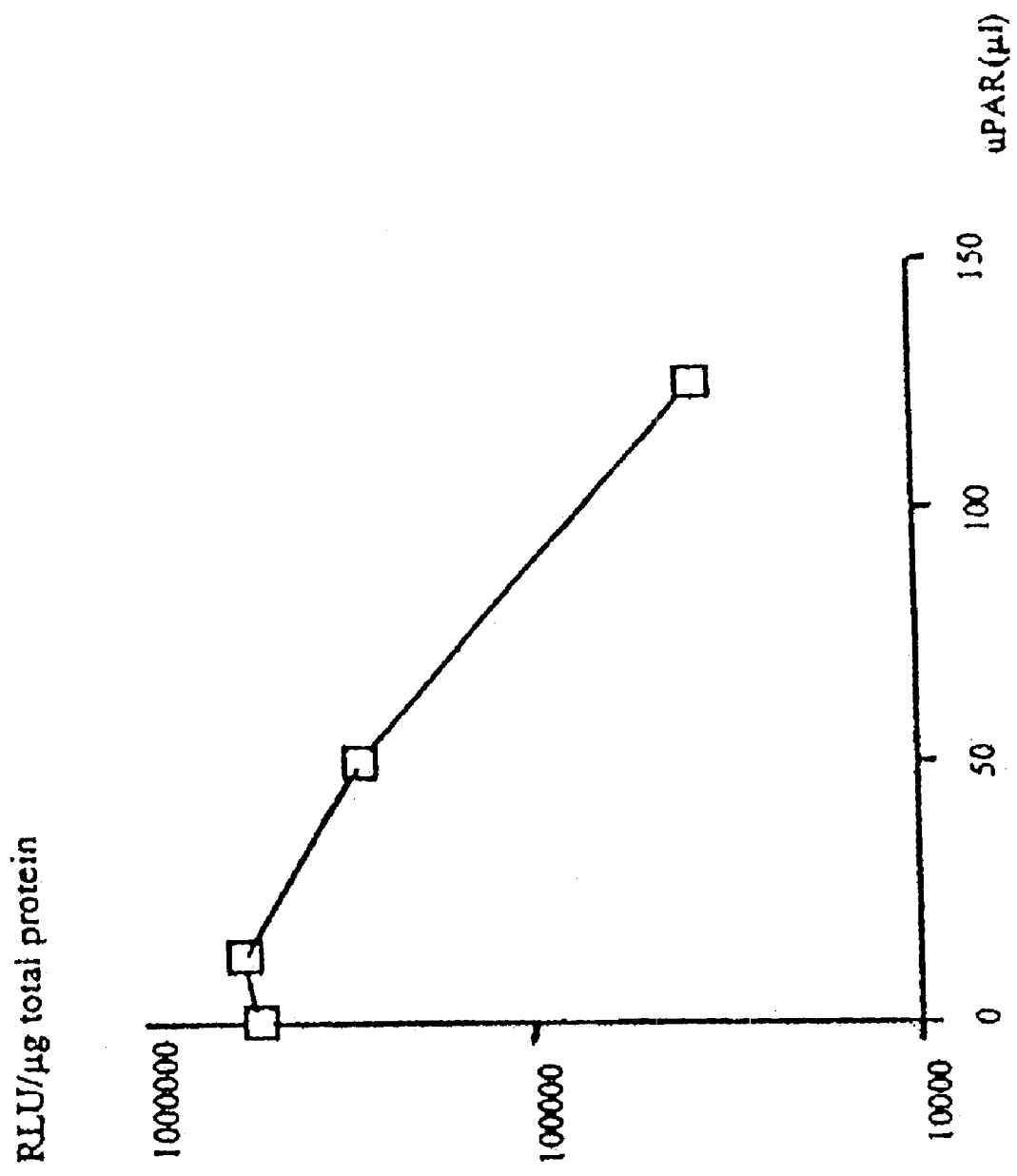

```
                              SEQUENCE LISTING

<160> NUMBER OF SEQ ID NOS: 165

<210> SEQ ID NO 1
<211> LENGTH: 19
<212> TYPE: PRT
<213> ORGANISM: Adenovirus

<400> SEQUENCE: 1

Leu Asn Gly Gly Thr Cys Val Ser Asn Lys Tyr Phe Ser Asn Ile His
1               5                   10                  15

Trp Cys Asn

<210> SEQ ID NO 2
<211> LENGTH: 19
<212> TYPE: PRT
<213> ORGANISM: Adenovirus

<400> SEQUENCE: 2

Leu Asn Gly Gly Thr Ala Val Ser Asn Lys Tyr Phe Ser Asn Ile His
1               5                   10                  15

Trp Cys Asn

<210> SEQ ID NO 3
<211> LENGTH: 16
<212> TYPE: PRT
<213> ORGANISM: Adenovirus

<400> SEQUENCE: 3

Ala Glu Pro Met Pro His Ser Leu Asn Phe Ser Gln Tyr Leu Trp Thr
1               5                   10                  15

<210> SEQ ID NO 4
<211> LENGTH: 17
<212> TYPE: PRT
<213> ORGANISM: Adenovirus

<400> SEQUENCE: 4

Ala Glu Pro Met Pro His Ser Leu Asn Phe Ser Gln Tyr Leu Trp Tyr
1               5                   10                  15

Thr

<210> SEQ ID NO 5
<211> LENGTH: 12
<212> TYPE: PRT
<213> ORGANISM: Adenovirus

<400> SEQUENCE: 5

Arg Gly His Ser Arg Gly Arg Asn Gln Asn Ser Arg
1               5                   10

<210> SEQ ID NO 6
<211> LENGTH: 10
<212> TYPE: PRT
<213> ORGANISM: Adenovirus

<400> SEQUENCE: 6

Asn Gln Asn Ser Arg Arg Pro Ser Arg Ala
1               5                   10
```

<210> SEQ ID NO 7
<211> LENGTH: 23
<212> TYPE: PRT
<213> ORGANISM: Adenovirus

<400> SEQUENCE: 7

Gly Ser Leu Asn Gly Gly Thr Cys Val Ser Asn Lys Tyr Phe Ser Asn
1               5                   10                  15

Ile His Trp Cys Asn Gly Ser
            20

<210> SEQ ID NO 8
<211> LENGTH: 23
<212> TYPE: PRT
<213> ORGANISM: Adenovirus

<400> SEQUENCE: 8

Gly Ser Leu Asn Gly Gly Thr Ala Val Ser Asn Lys Tyr Phe Ser Asn
1               5                   10                  15

Ile His Trp Cys Asn Gly Ser
            20

<210> SEQ ID NO 9
<211> LENGTH: 20
<212> TYPE: PRT
<213> ORGANISM: Adenovirus

<400> SEQUENCE: 9

Gly Ser Ala Glu Pro Met Pro His Ser Leu Asn Phe Ser Gln Tyr Leu
1               5                   10                  15

Trp Thr Gly Ser
            20

<210> SEQ ID NO 10
<211> LENGTH: 21
<212> TYPE: PRT
<213> ORGANISM: Adenovirus

<400> SEQUENCE: 10

Gly Ser Ala Glu Pro Met Pro His Ser Leu Asn Phe Ser Gln Tyr Leu
1               5                   10                  15

Trp Tyr Thr Gly Ser
            20

<210> SEQ ID NO 11
<211> LENGTH: 16
<212> TYPE: PRT
<213> ORGANISM: Adenovirus

<400> SEQUENCE: 11

Gly Ser Arg Gly His Ser Arg Gly Arg Asn Gln Asn Ser Arg Gly Ser
1               5                   10                  15

<210> SEQ ID NO 12
<211> LENGTH: 14
<212> TYPE: PRT
<213> ORGANISM: Adenovirus

<400> SEQUENCE: 12

Gly Ser Asn Gln Asn Ser Arg Arg Pro Ser Arg Ala Gly Ser
1               5                   10

<210> SEQ ID NO 13
<211> LENGTH: 13
<212> TYPE: PRT
<213> ORGANISM: Adenovirus

<400> SEQUENCE: 13

Gly Ser Cys Asp Cys Arg Gly Asp Cys Phe Cys Gly Ser
1               5                   10

<210> SEQ ID NO 14
<211> LENGTH: 11
<212> TYPE: PRT
<213> ORGANISM: Adenovirus

<400> SEQUENCE: 14

Gly Ser Asp Cys Arg Gly Asp Cys Phe Gly Ser
1               5                   10

<210> SEQ ID NO 15
<211> LENGTH: 11
<212> TYPE: PRT
<213> ORGANISM: Adenovirus

<400> SEQUENCE: 15

Gly Ser Lys Lys Lys Lys Lys Lys Gly Ser
1               5                   10

<210> SEQ ID NO 16
<211> LENGTH: 25
<212> TYPE: PRT
<213> ORGANISM: Adenovirus

<400> SEQUENCE: 16

Gly Ser Ser Leu Asn Gly Gly Thr Cys Val Ser Asn Lys Tyr Phe Ser
1               5                   10                  15

Asn Ile His Trp Cys Asn Gly Ser Ser
            20                  25

<210> SEQ ID NO 17
<211> LENGTH: 25
<212> TYPE: PRT
<213> ORGANISM: Adenovirus

<400> SEQUENCE: 17

Gly Ser Ser Leu Asn Gly Gly Thr Ala Val Ser Asn Lys Tyr Phe Ser
1               5                   10                  15

Asn Ile His Trp Cys Asn Gly Ser Ser
            20                  25

<210> SEQ ID NO 18
<211> LENGTH: 22
<212> TYPE: PRT
<213> ORGANISM: Adenovirus

<400> SEQUENCE: 18

Gly Ser Ser Ala Glu Pro Met Pro His Ser Leu Asn Phe Ser Gln Tyr
1               5                   10                  15

Leu Trp Thr Gly Ser Ser
            20

<210> SEQ ID NO 19
<211> LENGTH: 23
<212> TYPE: PRT

```
<213> ORGANISM: Adenovirus

<400> SEQUENCE: 19

Gly Ser Ser Ala Glu Pro Met Pro His Ser Leu Asn Phe Ser Gln Tyr
1               5                   10                  15

Leu Trp Tyr Thr Gly Ser Ser
            20

<210> SEQ ID NO 20
<211> LENGTH: 18
<212> TYPE: PRT
<213> ORGANISM: Adenovirus

<400> SEQUENCE: 20

Gly Ser Ser Arg Gly His Ser Arg Gly Arg Asn Gln Asn Ser Arg Gly
1               5                   10                  15

Ser Ser

<210> SEQ ID NO 21
<211> LENGTH: 16
<212> TYPE: PRT
<213> ORGANISM: Adenovirus

<400> SEQUENCE: 21

Gly Ser Ser Asn Gln Asn Ser Arg Arg Pro Ser Arg Ala Gly Ser Ser
1               5                   10                  15

<210> SEQ ID NO 22
<211> LENGTH: 15
<212> TYPE: PRT
<213> ORGANISM: Adenovirus

<400> SEQUENCE: 22

Gly Ser Ser Cys Asp Cys Arg Gly Asp Cys Phe Cys Gly Ser Ser
1               5                   10                  15

<210> SEQ ID NO 23
<211> LENGTH: 13
<212> TYPE: PRT
<213> ORGANISM: Adenovirus

<400> SEQUENCE: 23

Gly Ser Ser Asp Cys Arg Gly Asp Cys Phe Gly Ser Ser
1               5                   10

<210> SEQ ID NO 24
<211> LENGTH: 13
<212> TYPE: PRT
<213> ORGANISM: Adenovirus

<400> SEQUENCE: 24

Gly Ser Ser Lys Lys Lys Lys Lys Lys Lys Gly Ser Ser
1               5                   10

<210> SEQ ID NO 25
<211> LENGTH: 13
<212> TYPE: PRT
<213> ORGANISM: Adenovirus

<400> SEQUENCE: 25

Thr Thr Glu Ala Ala Ala Gly Asn Gly Asp Asn Leu Thr
1               5                   10
```

```
<210> SEQ ID NO 26
<211> LENGTH: 20
<212> TYPE: DNA
<213> ORGANISM: Adenovirus

<400> SEQUENCE: 26
atgggatgaa gctgctactg                                                    20

<210> SEQ ID NO 27
<211> LENGTH: 26
<212> TYPE: DNA
<213> ORGANISM: Adenovirus

<400> SEQUENCE: 27
tcgcgagaaa aattgcattt ccactt                                             26

<210> SEQ ID NO 28
<211> LENGTH: 21
<212> TYPE: DNA
<213> ORGANISM: Adenovirus

<400> SEQUENCE: 28
cctaaaggtg gtattgtaca g                                                  21

<210> SEQ ID NO 29
<211> LENGTH: 20
<212> TYPE: DNA
<213> ORGANISM: Adenovirus

<400> SEQUENCE: 29
agcagtaatt tggaagttca                                                    20

<210> SEQ ID NO 30
<211> LENGTH: 44
<212> TYPE: DNA
<213> ORGANISM: Adenovirus

<400> SEQUENCE: 30
aatactacct ctttgaacga ccggcaaggc aatgctacta aacc                         44

<210> SEQ ID NO 31
<211> LENGTH: 47
<212> TYPE: DNA
<213> ORGANISM: Adenovirus

<400> SEQUENCE: 31
ttaggtttag tagcattgcc ttgccggtcg ttcaaagagg tagtatt                      47

<210> SEQ ID NO 32
<211> LENGTH: 56
<212> TYPE: DNA
<213> ORGANISM: Adenovirus

<400> SEQUENCE: 32
aatctagact ctttggaaca acctactact cgcgctacaa aaaccacgtc tagatt           56

<210> SEQ ID NO 33
<211> LENGTH: 60
<212> TYPE: DNA
<213> ORGANISM: Adenovirus

<400> SEQUENCE: 33
gtacaaatct agacgtggtt tttgagcgcg agtagtaggt tgttccaaag agtctagatt       60
```

```
<210> SEQ ID NO 34
<211> LENGTH: 20
<212> TYPE: DNA
<213> ORGANISM: Adenovirus

<400> SEQUENCE: 34
tcaaccacta taaacattcc                                              20

<210> SEQ ID NO 35
<211> LENGTH: 23
<212> TYPE: DNA
<213> ORGANISM: Adenovirus

<400> SEQUENCE: 35
ttaggaatgt ttatagtggt tga                                          23

<210> SEQ ID NO 36
<211> LENGTH: 56
<212> TYPE: DNA
<213> ORGANISM: Adenovirus

<400> SEQUENCE: 36
ttaggtttgt attcttcgtt tccactaccg cctgctggag gatttgcgcc aggagt      56

<210> SEQ ID NO 37
<211> LENGTH: 56
<212> TYPE: DNA
<213> ORGANISM: Adenovirus

<400> SEQUENCE: 37
ttaggtttgt attcttcgtt tccactaccg cctgctggag gatttgcgcc aggagt      56

<210> SEQ ID NO 38
<211> LENGTH: 38
<212> TYPE: DNA
<213> ORGANISM: Adenovirus

<400> SEQUENCE: 38
gataacccag cgtcgaccac gaataaggat aagctacc                          38

<210> SEQ ID NO 39
<211> LENGTH: 41
<212> TYPE: DNA
<213> ORGANISM: Adenovirus

<400> SEQUENCE: 39
ttaggtagct tatccttatt cgtggtcgac gctgggttat c                      41

<210> SEQ ID NO 40
<211> LENGTH: 38
<212> TYPE: DNA
<213> ORGANISM: Adenovirus

<400> SEQUENCE: 40
ggagataacc cagcgtcgac cacgaataag gataagcc                          38

<210> SEQ ID NO 41
<211> LENGTH: 41
<212> TYPE: DNA
<213> ORGANISM: Adenovirus

<400> SEQUENCE: 41
ttaggcttat ccttattcgt ggtcgacgct gggttatctc c                      41
```

<210> SEQ ID NO 42
<211> LENGTH: 38
<212> TYPE: DNA
<213> ORGANISM: Adenovirus

<400> SEQUENCE: 42
tctgataacc cagcgtcgac cacgaataag gataagcc                    38

<210> SEQ ID NO 43
<211> LENGTH: 41
<212> TYPE: DNA
<213> ORGANISM: Adenovirus

<400> SEQUENCE: 43
ttaggcttat ccttattcgt ggtcgacgct gggttatcag a                41

<210> SEQ ID NO 44
<211> LENGTH: 40
<212> TYPE: DNA
<213> ORGANISM: Adenovirus

<400> SEQUENCE: 44
ggatctgata acccagcgtc gaccacgaat aaggataagc                  40

<210> SEQ ID NO 45
<211> LENGTH: 44
<212> TYPE: DNA
<213> ORGANISM: Adenovirus

<400> SEQUENCE: 45
ttaggcttat ccttattcgt ggtcgacgct gggttatcag atcc             44

<210> SEQ ID NO 46
<211> LENGTH: 47
<212> TYPE: DNA
<213> ORGANISM: Adenovirus

<400> SEQUENCE: 46
ggagataacc cagcgtcgac cacgaataag gataagctag gtggccc          47

<210> SEQ ID NO 47
<211> LENGTH: 50
<212> TYPE: DNA
<213> ORGANISM: Adenovirus

<400> SEQUENCE: 47
ttagggccac ctagcttatc cttattcgtg gtcgacgctg ggttatctcc       50

<210> SEQ ID NO 48
<211> LENGTH: 47
<212> TYPE: DNA
<213> ORGANISM: Adenovirus

<400> SEQUENCE: 48
ggagataacc cagcgtcgac cacgaataag gataagctag gttctcc          47

<210> SEQ ID NO 49
<211> LENGTH: 50
<212> TYPE: DNA
<213> ORGANISM: Adenovirus

<400> SEQUENCE: 49

```
ttaggagaac ctagcttatc cttattcgtg gtcgacgctg ggttatctcc        50

<210> SEQ ID NO 50
<211> LENGTH: 44
<212> TYPE: DNA
<213> ORGANISM: Adenovirus

<400> SEQUENCE: 50
ggagataacc cagcgtcgac cacgaataag gataagctat ctcc              44

<210> SEQ ID NO 51
<211> LENGTH: 47
<212> TYPE: DNA
<213> ORGANISM: Adenovirus

<400> SEQUENCE: 51
ttaggagata gcttatcctt attcgtggtc gacgctgggt tatctcc           47

<210> SEQ ID NO 52
<211> LENGTH: 47
<212> TYPE: DNA
<213> ORGANISM: Adenovirus

<400> SEQUENCE: 52
ggagataacc cagcgtcgac cacgaataag gataagctat ctggtcc           47

<210> SEQ ID NO 53
<211> LENGTH: 50
<212> TYPE: DNA
<213> ORGANISM: Adenovirus

<400> SEQUENCE: 53
ttaggaccag atagcttatc cttattcgtg gtcgacgctg ggttatctcc        50

<210> SEQ ID NO 54
<211> LENGTH: 47
<212> TYPE: DNA
<213> ORGANISM: Adenovirus

<400> SEQUENCE: 54
ggagataacc cagcgtcgac cacgaataag gataagctat ctagtcc           47

<210> SEQ ID NO 55
<211> LENGTH: 50
<212> TYPE: DNA
<213> ORGANISM: Adenovirus

<400> SEQUENCE: 55
ttaggactag atagcttatc cttattcgtg gtcgacgctg ggttatctcc        50

<210> SEQ ID NO 56
<211> LENGTH: 14
<212> TYPE: PRT
<213> ORGANISM: Adenovirus

<400> SEQUENCE: 56

Asn Thr Thr Ser Leu Asn Asp Arg Gln Gly Asn Ala Thr Lys
 1               5                  10

<210> SEQ ID NO 57
<211> LENGTH: 6
<212> TYPE: PRT
<213> ORGANISM: Adenovirus
```

```
<400> SEQUENCE: 57

Ser Thr Thr Ile Asn Ile
1               5

<210> SEQ ID NO 58
<211> LENGTH: 16
<212> TYPE: PRT
<213> ORGANISM: Adenovirus

<400> SEQUENCE: 58

Thr Pro Gly Ala Asn Pro Pro Ala Gly Gly Ser Gly Asn Glu Glu Tyr
1               5                   10                  15

<210> SEQ ID NO 59
<211> LENGTH: 17
<212> TYPE: PRT
<213> ORGANISM: Adenovirus

<400> SEQUENCE: 59

Thr Thr Glu Ala Thr Ala Gly Asn Gly Asp Asn Leu Thr Pro Lys Val
1               5                   10                  15

Val

<210> SEQ ID NO 60
<211> LENGTH: 13
<212> TYPE: PRT
<213> ORGANISM: Adenovirus

<400> SEQUENCE: 60

Thr Thr Glu Ala Thr Ala Gly Asn Gly Asp Asn Leu Tyr
1               5                   10

<210> SEQ ID NO 61
<211> LENGTH: 18
<212> TYPE: PRT
<213> ORGANISM: Adenovirus

<400> SEQUENCE: 61

Asn Leu Asp Ser Leu Glu Gln Pro Thr Thr Arg Ala Gln Lys Pro Arg
1               5                   10                  15

Leu Asp

<210> SEQ ID NO 62
<211> LENGTH: 11
<212> TYPE: PRT
<213> ORGANISM: Adenovirus

<400> SEQUENCE: 62

Asp Asn Pro Ala Ser Thr Thr Asn Lys Asp Lys
1               5                   10

<210> SEQ ID NO 63
<211> LENGTH: 12
<212> TYPE: PRT
<213> ORGANISM: Adenovirus

<400> SEQUENCE: 63

Asp Asn Pro Ala Ser Thr Thr Asn Lys Asp Lys Leu
1               5                   10

<210> SEQ ID NO 64
<211> LENGTH: 12
<212> TYPE: PRT
```

```
<213> ORGANISM: Adenovirus

<400> SEQUENCE: 64

Gly Asp Asn Pro Ala Ser Thr Thr Asn Lys Asp Lys
1               5                   10

<210> SEQ ID NO 65
<211> LENGTH: 12
<212> TYPE: PRT
<213> ORGANISM: Adenovirus

<400> SEQUENCE: 65

Ser Asp Asn Pro Ala Ser Thr Thr Asn Lys Asp Lys
1               5                   10

<210> SEQ ID NO 66
<211> LENGTH: 13
<212> TYPE: PRT
<213> ORGANISM: Adenovirus

<400> SEQUENCE: 66

Gly Ser Asp Asn Pro Ala Ser Thr Thr Asn Lys Asp Lys
1               5                   10

<210> SEQ ID NO 67
<211> LENGTH: 15
<212> TYPE: PRT
<213> ORGANISM: Adenovirus

<400> SEQUENCE: 67

Gly Asp Asn Pro Ala Ser Thr Thr Asn Lys Asp Lys Leu Gly Gly
1               5                   10                  15

<210> SEQ ID NO 68
<211> LENGTH: 15
<212> TYPE: PRT
<213> ORGANISM: Adenovirus

<400> SEQUENCE: 68

Gly Asp Asn Pro Ala Ser Thr Thr Asn Lys Asp Lys Leu Gly Ser
1               5                   10                  15

<210> SEQ ID NO 69
<211> LENGTH: 14
<212> TYPE: PRT
<213> ORGANISM: Adenovirus

<400> SEQUENCE: 69

Gly Asp Asn Pro Ala Ser Thr Thr Asn Lys Asp Lys Leu Ser
1               5                   10

<210> SEQ ID NO 70
<211> LENGTH: 15
<212> TYPE: PRT
<213> ORGANISM: Adenovirus

<400> SEQUENCE: 70

Gly Asp Asn Pro Ala Ser Thr Thr Asn Lys Asp Lys Leu Ser Gly
1               5                   10                  15

<210> SEQ ID NO 71
<211> LENGTH: 15
<212> TYPE: PRT
<213> ORGANISM: Adenovirus
```

```
<400> SEQUENCE: 71

Gly Asp Asn Pro Ala Ser Thr Thr Asn Lys Asp Lys Leu Ser Ser
1               5                   10                  15

<210> SEQ ID NO 72
<211> LENGTH: 11
<212> TYPE: PRT
<213> ORGANISM: Adenovirus

<400> SEQUENCE: 72

Gly Thr Gln Glu Thr Gly Asp Thr Thr Pro Ser
1               5                   10

<210> SEQ ID NO 73
<211> LENGTH: 30
<212> TYPE: DNA
<213> ORGANISM: Adenovirus

<400> SEQUENCE: 73
cagctccatc tcctaactgt agactaaatg                                30

<210> SEQ ID NO 74
<211> LENGTH: 30
<212> TYPE: DNA
<213> ORGANISM: Adenovirus

<400> SEQUENCE: 74
ggttaccggt ttagttttgt ctccgtttaa                                30

<210> SEQ ID NO 75
<211> LENGTH: 30
<212> TYPE: DNA
<213> ORGANISM: Adenovirus

<400> SEQUENCE: 75
agcgcttact ctatgtcatt ttcatgggac                                30

<210> SEQ ID NO 76
<211> LENGTH: 30
<212> TYPE: DNA
<213> ORGANISM: Adenovirus

<400> SEQUENCE: 76
gagtttatta atatcactga tgagcgtttg                                30

<210> SEQ ID NO 77
<211> LENGTH: 57
<212> TYPE: DNA
<213> ORGANISM: Adenovirus

<400> SEQUENCE: 77
gtaacactaa ccattacact aaacggtacc caggaaacag agacacaac tccaagt    57

<210> SEQ ID NO 78
<211> LENGTH: 52
<212> TYPE: DNA
<213> ORGANISM: Adenovirus

<400> SEQUENCE: 78
acttggagtt gtgtctcctg tttcctgggt accgtttagt gtaatggtta gt        52

<210> SEQ ID NO 79
<211> LENGTH: 60
```

```
<212> TYPE: DNA
<213> ORGANISM: Adenovirus

<400> SEQUENCE: 79
gtaacactaa ccattacact aaacggtacc agtgaatcca cagaaactag cgaggtaagc        60

<210> SEQ ID NO 80
<211> LENGTH: 55
<212> TYPE: DNA
<213> ORGANISM: Adenovirus

<400> SEQUENCE: 80
gcttaccctc gctagttttc tgtggatcac tggtaccgtt tagtgtaatg ttagt            55

<210> SEQ ID NO 81
<211> LENGTH: 42
<212> TYPE: DNA
<213> ORGANISM: Adenovirus

<400> SEQUENCE: 81
gtaacactaa ccattacact aaaccaagaa acacaatgtg aa                           42

<210> SEQ ID NO 82
<211> LENGTH: 37
<212> TYPE: DNA
<213> ORGANISM: Adenovirus

<400> SEQUENCE: 82
ttcacattgt gtttcttggt ttagtgtaat ggttagt                                 37

<210> SEQ ID NO 83
<211> LENGTH: 60
<212> TYPE: DNA
<213> ORGANISM: Adenovirus

<400> SEQUENCE: 83
gtaaccctaa ccattacact aaacggtgat aacccagcgt cgaccacgaa taaggataag        60

<210> SEQ ID NO 84
<211> LENGTH: 58
<212> TYPE: DNA
<213> ORGANISM: Adenovirus

<400> SEQUENCE: 84
gctcttatcc ttattcgtgg tcgacgctgg gttatcaccg tttagtgtaa tggttagg          58

<210> SEQ ID NO 85
<211> LENGTH: 66
<212> TYPE: DNA
<213> ORGANISM: Adenovirus

<400> SEQUENCE: 85
gtaaccctaa ccattacact aaacggtgat aacccagcgt cgaccacgaa taaggataag        60
ggaagc                                                                   66

<210> SEQ ID NO 86
<211> LENGTH: 61
<212> TYPE: DNA
<213> ORGANISM: Adenovirus

<400> SEQUENCE: 86
gcttccctta tccttattcg tggtcgacgc tgggttatca ccgtttagtg taatggttag        60
```

```
<210> SEQ ID NO 87
<211> LENGTH: 66
<212> TYPE: DNA
<213> ORGANISM: Adenovirus

<400> SEQUENCE: 87
gtaaccctaa ccattacact aaacggtgat aacccagcgt cgaccacgaa taaggataag      60
tcaagc                                                                66

<210> SEQ ID NO 88
<211> LENGTH: 61
<212> TYPE: DNA
<213> ORGANISM: Adenovirus

<400> SEQUENCE: 88
gcttgactta tccttattcg tggtcgacgc tgggttatca ccgtttagtg taatggttag      60
g                                                                     61

<210> SEQ ID NO 89
<211> LENGTH: 69
<212> TYPE: DNA
<213> ORGANISM: Adenovirus

<400> SEQUENCE: 89
gtaaccctaa ccattacact aaacggtgat aacccagcgt cgaccacgaa taaggataag      60
ggcggaagc                                                             69

<210> SEQ ID NO 90
<211> LENGTH: 64
<212> TYPE: DNA
<213> ORGANISM: Adenovirus

<400> SEQUENCE: 90
gcttccgccc ttatccttat tcgtggtcga cgctgggtta tcaccgttta gtgtaatggt      60
tagg                                                                  64

<210> SEQ ID NO 91
<211> LENGTH: 69
<212> TYPE: DNA
<213> ORGANISM: Adenovirus

<400> SEQUENCE: 91
gtaaccctaa ccattacact aaacggtgat aacccagcgt cgaccacgaa taaggataag      60
tcatctagc                                                             69

<210> SEQ ID NO 92
<211> LENGTH: 64
<212> TYPE: DNA
<213> ORGANISM: Adenovirus

<400> SEQUENCE: 92
gctagatgac ttatccttat tcgtggtcga cgctgggtta tcaccgttta gtgtaatggt      60
tagg                                                                  64

<210> SEQ ID NO 93
<211> LENGTH: 69
<212> TYPE: DNA
<213> ORGANISM: Adenovirus
```

-continued

<400> SEQUENCE: 93
gtaaccctaa ccattacact aaacggtgat aacccagcgt cgaccacgaa taaggataag    60
ggatccagc                                                            69

<210> SEQ ID NO 94
<211> LENGTH: 64
<212> TYPE: DNA
<213> ORGANISM: Adenovirus

<400> SEQUENCE: 94
gctggatccc ttatccttat tcgtggtcga cgctgggtta tcaccgttta gtgtaatggt    60
tagg                                                                 64

<210> SEQ ID NO 95
<211> LENGTH: 69
<212> TYPE: DNA
<213> ORGANISM: Adenovirus

<400> SEQUENCE: 95
gtaaccctaa ccattacact aaacggtgat aacccagcgt cgaccacgaa taaggataag    60
tcaggaagc                                                            69

<210> SEQ ID NO 96
<211> LENGTH: 64
<212> TYPE: DNA
<213> ORGANISM: Adenovirus

<400> SEQUENCE: 96
gcttcctgac ttatccttat tcgtggtcga cgctgggtta tcaccgttta gtgtaatggt    60
tagg                                                                 64

<210> SEQ ID NO 97
<211> LENGTH: 60
<212> TYPE: DNA
<213> ORGANISM: Adenovirus

<400> SEQUENCE: 97
gtaaccctaa ccattacact aaacggtgat aacccagcgt cgaccacgaa taaggataag    60

<210> SEQ ID NO 98
<211> LENGTH: 55
<212> TYPE: DNA
<213> ORGANISM: Adenovirus

<400> SEQUENCE: 98
cttatcctta ttcgtggtcg acgctgggtt atcaccgttt agtgtaatgg ttagg         55

<210> SEQ ID NO 99
<211> LENGTH: 12
<212> TYPE: PRT
<213> ORGANISM: Adenovirus

<400> SEQUENCE: 99

Gly Thr Ser Glu Ser Thr Glu Thr Ser Glu Val Ser
1               5                   10

<210> SEQ ID NO 100
<211> LENGTH: 11
<212> TYPE: PRT
<213> ORGANISM: Adenovirus

<400> SEQUENCE: 100

Gly Thr Gln Glu Thr Gly Asp Thr Thr Pro Ser
1               5                   10

<210> SEQ ID NO 101
<211> LENGTH: 6
<212> TYPE: PRT
<213> ORGANISM: Adenovirus

<400> SEQUENCE: 101

Gln Glu Thr Gln Cys Glu
1               5

<210> SEQ ID NO 102
<211> LENGTH: 12
<212> TYPE: PRT
<213> ORGANISM: Adenovirus

<400> SEQUENCE: 102

Asp Asn Pro Ala Ser Thr Thr Asn Lys Asp Lys Ser
1               5                   10

<210> SEQ ID NO 103
<211> LENGTH: 13
<212> TYPE: PRT
<213> ORGANISM: Adenovirus

<400> SEQUENCE: 103

Asp Asn Pro Ala Ser Thr Thr Asn Lys Asp Lys Gly Ser
1               5                   10

<210> SEQ ID NO 104
<211> LENGTH: 13
<212> TYPE: PRT
<213> ORGANISM: Adenovirus

<400> SEQUENCE: 104

Asp Asn Pro Ala Ser Thr Thr Asn Lys Asp Lys Ser Ser
1               5                   10

<210> SEQ ID NO 105
<211> LENGTH: 14
<212> TYPE: PRT
<213> ORGANISM: Adenovirus

<400> SEQUENCE: 105

Asp Asn Pro Ala Ser Thr Thr Asn Lys Asp Lys Gly Gly Ser
1               5                   10

<210> SEQ ID NO 106
<211> LENGTH: 14
<212> TYPE: PRT
<213> ORGANISM: Adenovirus

<400> SEQUENCE: 106

Asp Asn Pro Ala Ser Thr Thr Asn Lys Asp Lys Ser Ser Ser
1               5                   10

<210> SEQ ID NO 107
<211> LENGTH: 14
<212> TYPE: PRT
<213> ORGANISM: Adenovirus

<400> SEQUENCE: 107

Asp Asn Pro Ala Ser Thr Thr Asn Lys Asp Lys Gly Ser Ser
1               5                   10

<210> SEQ ID NO 108
<211> LENGTH: 14
<212> TYPE: PRT
<213> ORGANISM: Adenovirus

<400> SEQUENCE: 108

Asp Asn Pro Ala Ser Thr Thr Asn Lys Asp Lys Ser Gly Ser
1               5                   10

<210> SEQ ID NO 109
<211> LENGTH: 11
<212> TYPE: PRT
<213> ORGANISM: Adenovirus

<400> SEQUENCE: 109

Asp Asn Pro Ala Ser Thr Thr Asn Lys Asp Lys
1               5                   10

<210> SEQ ID NO 110
<211> LENGTH: 30
<212> TYPE: DNA
<213> ORGANISM: Adenovirus

<400> SEQUENCE: 110
atttctgtcg actttattca gcagcacctc                                    30

<210> SEQ ID NO 111
<211> LENGTH: 30
<212> TYPE: DNA
<213> ORGANISM: Adenovirus

<400> SEQUENCE: 111
gtttgacttg gttttttga gaggtgggct                                     30

<210> SEQ ID NO 112
<211> LENGTH: 30
<212> TYPE: DNA
<213> ORGANISM: Adenovirus

<400> SEQUENCE: 112
ttggatatta actacaacaa aggcctttac                                    30

<210> SEQ ID NO 113
<211> LENGTH: 30
<212> TYPE: DNA
<213> ORGANISM: Adenovirus

<400> SEQUENCE: 113
gaaactggag ctcgtatttg actgccacat                                    30

<210> SEQ ID NO 114
<211> LENGTH: 30
<212> TYPE: DNA
<213> ORGANISM: Adenovirus

<400> SEQUENCE: 114
atttctgtcg actttattca gcagcacctc                                    30

<210> SEQ ID NO 115
<211> LENGTH: 30

<212> TYPE: DNA
<213> ORGANISM: Adenovirus

<400> SEQUENCE: 115
gtttgacttg gttttttga gaggtgggct                30

<210> SEQ ID NO 116
<211> LENGTH: 30
<212> TYPE: DNA
<213> ORGANISM: Adenovirus

<400> SEQUENCE: 116
ctcaaaacaa aaattggcca tggcctagaa                30

<210> SEQ ID NO 117
<211> LENGTH: 30
<212> TYPE: DNA
<213> ORGANISM: Adenovirus

<400> SEQUENCE: 117
atccaagagc tcttgtatag gctgtgcctt                30

<210> SEQ ID NO 118
<211> LENGTH: 30
<212> TYPE: DNA
<213> ORGANISM: Adenovirus

<400> SEQUENCE: 118
tacaagtcga caaccaagcg tcagaaattg                30

<210> SEQ ID NO 119
<211> LENGTH: 30
<212> TYPE: DNA
<213> ORGANISM: Adenovirus

<400> SEQUENCE: 119
aagacttaaa accccagggg gactctcttg                30

<210> SEQ ID NO 120
<211> LENGTH: 30
<212> TYPE: DNA
<213> ORGANISM: Adenovirus

<400> SEQUENCE: 120
gagagtcccc ctggggtttt aagtcttaaa                30

<210> SEQ ID NO 121
<211> LENGTH: 30
<212> TYPE: DNA
<213> ORGANISM: Adenovirus

<400> SEQUENCE: 121
ggtccacaaa gtgttatttt tcagtgcaat                30

<210> SEQ ID NO 122
<211> LENGTH: 30
<212> TYPE: DNA
<213> ORGANISM: Adenovirus

<400> SEQUENCE: 122
ctgaaaaata acactttgtg gaccacacca                30

<210> SEQ ID NO 123

```
<211> LENGTH: 30
<212> TYPE: DNA
<213> ORGANISM: Adenovirus

<400> SEQUENCE: 123
tcctgagctc cgtttagtgt aatggttagt                              30

<210> SEQ ID NO 124
<211> LENGTH: 9
<212> TYPE: PRT
<213> ORGANISM: Adenovirus

<400> SEQUENCE: 124

Cys Asp Cys Arg Gly Asp Cys Phe Cys
1               5

<210> SEQ ID NO 125
<211> LENGTH: 13
<212> TYPE: PRT
<213> ORGANISM: Adenovirus

<400> SEQUENCE: 125

Thr Thr Glu Ala Thr Ala Gly Asn Gly Asp Asn Leu Thr
1               5                   10

<210> SEQ ID NO 126
<211> LENGTH: 31
<212> TYPE: DNA
<213> ORGANISM: Adenovirus

<400> SEQUENCE: 126
ggaactttag aaatggagat cttactgaag g                            31

<210> SEQ ID NO 127
<211> LENGTH: 33
<212> TYPE: DNA
<213> ORGANISM: Adenovirus

<400> SEQUENCE: 127 cgattctttta ttcttgcgca atgtatgaaa aag                         33

<210> SEQ ID NO 128
<211> LENGTH: 22
<212> TYPE: DNA
<213> ORGANISM: Adenovirus

<400> SEQUENCE: 128
cttaagtgag ctgcccgggg ag                                      22

<210> SEQ ID NO 129
<211> LENGTH: 23
<212> TYPE: DNA
<213> ORGANISM: Adenovirus

<400> SEQUENCE: 129
ggatccaatg aacttcatca agt                                     23

<210> SEQ ID NO 130
<211> LENGTH: 49
<212> TYPE: DNA
<213> ORGANISM: Adenovirus

<400> SEQUENCE: 130
aattctgcgc aagaaccaaa gagggccagg cccggatcct aagacgtct          49
```

<210> SEQ ID NO 131
<211> LENGTH: 49
<212> TYPE: DNA
<213> ORGANISM: Adenovirus

<400> SEQUENCE: 131
ctagagacgt cttaggatcc gggcctggcc ctctttggtt cttgcgcag          49

<210> SEQ ID NO 132
<211> LENGTH: 15
<212> TYPE: PRT
<213> ORGANISM: Adenovirus

<400> SEQUENCE: 132

Pro Lys Arg Ala Arg Pro Gly Ser Lys Lys Lys Lys Lys Lys Lys
1               5                   10                  15

<210> SEQ ID NO 133
<211> LENGTH: 10
<212> TYPE: PRT
<213> ORGANISM: Adenovirus

<400> SEQUENCE: 133

Arg Arg Leu Leu Arg Arg Leu Leu Arg Arg
1               5                   10

<210> SEQ ID NO 134
<211> LENGTH: 11
<212> TYPE: PRT
<213> ORGANISM: Adenovirus

<400> SEQUENCE: 134

Lys Arg Gly Pro Arg Thr His Tyr Gly Gln Lys
1               5                   10

<210> SEQ ID NO 135
<211> LENGTH: 9
<212> TYPE: PRT
<213> ORGANISM: Adenovirus

<400> SEQUENCE: 135

Gly Ser Lys Lys Lys Lys Lys Gly Ser
1               5

<210> SEQ ID NO 136
<211> LENGTH: 13
<212> TYPE: PRT
<213> ORGANISM: Adenovirus

<400> SEQUENCE: 136

Gly Ser Ser Lys Lys Lys Lys Lys Lys Lys Gly Ser Ser
1               5                   10

<210> SEQ ID NO 137
<211> LENGTH: 17
<212> TYPE: PRT
<213> ORGANISM: Adenovirus

<400> SEQUENCE: 137

Gly Ser Gly Ser Gly Ser Gly Ser Gly Ser Lys Lys Lys Lys Lys
1               5                   10                  15

Lys

<210> SEQ ID NO 138
<211> LENGTH: 15
<212> TYPE: PRT
<213> ORGANISM: Adenovirus

<400> SEQUENCE: 138

Pro Lys Arg Ala Arg Pro Gly Ser Lys Lys Lys Lys Lys Lys Lys
1               5                   10                  15

<210> SEQ ID NO 139
<211> LENGTH: 8
<212> TYPE: PRT
<213> ORGANISM: Adenovirus

<400> SEQUENCE: 139

Lys Lys Lys Lys Lys Lys Lys Lys
1               5

<210> SEQ ID NO 140
<211> LENGTH: 19
<212> TYPE: PRT
<213> ORGANISM: Adenovirus

<400> SEQUENCE: 140

Pro Lys Arg Ala Arg Pro Gly Ser Lys Arg Gly Pro Arg Thr His Tyr
1               5                   10                  15

Gly Gln Lys

<210> SEQ ID NO 141
<211> LENGTH: 18
<212> TYPE: PRT
<213> ORGANISM: Adenovirus

<400> SEQUENCE: 141

Pro Lys Arg Ala Arg Pro Gly Ser Arg Arg Leu Leu Arg Arg Leu Leu
1               5                   10                  15

Arg Arg

<210> SEQ ID NO 142
<211> LENGTH: 17
<212> TYPE: PRT
<213> ORGANISM: Adenovirus

<400> SEQUENCE: 142

Ser Ser Arg Gly His Ser Arg Gly Arg Asn Gln Asn Ser Arg Gly Ser
1               5                   10                  15

Ser

<210> SEQ ID NO 143
<211> LENGTH: 23
<212> TYPE: PRT
<213> ORGANISM: Adenovirus

<400> SEQUENCE: 143

Gly Ser Ser Arg Gly His Ser Arg Gly Arg Asn Gln Asn Ser Arg Arg
1               5                   10                  15

Pro Ser Arg Ala Gly Ser Ser
            20

<210> SEQ ID NO 144
<211> LENGTH: 19
<212> TYPE: PRT

```
<213> ORGANISM: Adenovirus

<400> SEQUENCE: 144

Gly Thr Ser Glu Arg Gly His Ser Arg Gly Arg Asn Gln Asn Ser Arg
1               5                   10                  15

Gly Ser Ser

<210> SEQ ID NO 145
<211> LENGTH: 19
<212> TYPE: PRT
<213> ORGANISM: Adenovirus

<400> SEQUENCE: 145

Gly Thr Gln Glu Arg Gly His Ser Arg Gly Arg Asn Gln Asn Ser Arg
1               5                   10                  15

Gly Ser Ser

<210> SEQ ID NO 146
<211> LENGTH: 19
<212> TYPE: PRT
<213> ORGANISM: Adenovirus

<400> SEQUENCE: 146

Gly Ser Ser Arg Gly His Ser Arg Gly Arg Asn Gln Asn Ser Arg
1               5                   10                  15

Gly Ser Ser

<210> SEQ ID NO 147
<211> LENGTH: 18
<212> TYPE: PRT
<213> ORGANISM: Adenovirus

<400> SEQUENCE: 147

Gly Ser Ser Arg Gly His Ser Arg Gly Arg Asn Gln Asn Ser Arg Gly
1               5                   10                  15

Gly Ser

<210> SEQ ID NO 148
<211> LENGTH: 7
<212> TYPE: PRT
<213> ORGANISM: Adenovirus

<400> SEQUENCE: 148

Asp Cys Arg Gly Asp Cys Phe
1               5

<210> SEQ ID NO 149
<211> LENGTH: 8
<212> TYPE: PRT
<213> ORGANISM: Adenovirus

<400> SEQUENCE: 149

Pro Lys Arg Ala Arg Pro Gly Ser
1               5

<210> SEQ ID NO 150
<211> LENGTH: 16
<212> TYPE: PRT
<213> ORGANISM: Adenovirus

<400> SEQUENCE: 150

Ser Ser Arg Gly His Ser Arg Gly Arg Asn Gly Asn Ser Arg Gly Ser
```

```
                1               5                    10                   15
```

<210> SEQ ID NO 151
<211> LENGTH: 13
<212> TYPE: PRT
<213> ORGANISM: Adenovirus

<400> SEQUENCE: 151

```
Gly Asp Asn Pro Ala Ser Thr Thr Asn Lys Asp Lys Ser
1               5                   10
```

<210> SEQ ID NO 152
<211> LENGTH: 14
<212> TYPE: PRT
<213> ORGANISM: Adenovirus

<400> SEQUENCE: 152

```
Gly Asp Asn Pro Ala Ser Thr Thr Asn Lys Asp Lys Gly Ser
1               5                   10
```

<210> SEQ ID NO 153
<211> LENGTH: 14
<212> TYPE: PRT
<213> ORGANISM: Adenovirus

<400> SEQUENCE: 153

```
Gly Asp Asn Pro Ala Ser Thr Thr Asn Lys Asp Lys Ser Ser
1               5                   10
```

<210> SEQ ID NO 154
<211> LENGTH: 15
<212> TYPE: PRT
<213> ORGANISM: Adenovirus

<400> SEQUENCE: 154

```
Gly Asp Asn Pro Ala Ser Thr Thr Asn Lys Asp Lys Gly Gly Ser
1               5                   10                  15
```

<210> SEQ ID NO 155
<211> LENGTH: 15
<212> TYPE: PRT
<213> ORGANISM: Adenovirus

<400> SEQUENCE: 155

```
Gly Asp Asn Pro Ala Ser Thr Thr Asn Lys Asp Lys Ser Ser Ser
1               5                   10                  15
```

<210> SEQ ID NO 156
<211> LENGTH: 15
<212> TYPE: PRT
<213> ORGANISM: Adenovirus

<400> SEQUENCE: 156

```
Gly Asp Asn Pro Ala Ser Thr Thr Asn Lys Asp Lys Gly Ser Ser
1               5                   10                  15
```

<210> SEQ ID NO 157
<211> LENGTH: 15
<212> TYPE: PRT
<213> ORGANISM: Adenovirus

<400> SEQUENCE: 157

```
Gly Asp Asn Pro Ala Ser Thr Thr Asn Lys Asp Lys Ser Gly Ser
1               5                   10                  15
```

```
<210> SEQ ID NO 158
<211> LENGTH: 5
<212> TYPE: PRT
<213> ORGANISM: Human

<400> SEQUENCE: 158

Lys Gln Ala Gly Asp
1               5

<210> SEQ ID NO 159
<211> LENGTH: 5
<212> TYPE: PRT
<213> ORGANISM: Human

<400> SEQUENCE: 159

Glu Ile Leu Asp Val
1               5

<210> SEQ ID NO 160
<211> LENGTH: 4
<212> TYPE: PRT
<213> ORGANISM: Human
<220> FEATURE:
<221> NAME/KEY: misc_feature
<222> LOCATION: (3)..(3)
<223> OTHER INFORMATION: Xaa can be any naturally occurring amino acid

<400> SEQUENCE: 160

Asn Pro Xaa Tyr
1

<210> SEQ ID NO 161
<211> LENGTH: 7
<212> TYPE: PRT
<213> ORGANISM: Adenovirus

<400> SEQUENCE: 161

Pro Gly Val Leu Ser Leu Lys
1               5

<210> SEQ ID NO 162
<211> LENGTH: 7
<212> TYPE: PRT
<213> ORGANISM: Adenovirus

<400> SEQUENCE: 162

Asn Asn Thr Leu Trp Thr Thr
1               5

<210> SEQ ID NO 163
<211> LENGTH: 21
<212> TYPE: DNA
<213> ORGANISM: Adenovirus

<400> SEQUENCE: 163
cctggggttt taagtcttaa a                                              21

<210> SEQ ID NO 164
<211> LENGTH: 21
<212> TYPE: DNA
<213> ORGANISM: Adenovirus

<400> SEQUENCE: 164
aataacactt tgtggaccac a                                              21
```

```
<210> SEQ ID NO 165
<211> LENGTH: 17
<212> TYPE: PRT
<213> ORGANISM: Human

<400> SEQUENCE: 165

Arg Gly His Ser Arg Gly Arg Asn Gln Asn Ser Arg Arg Pro Ser Arg
1               5                   10                  15
Ala
```

TARGETED ADENOVIRUS VECTORS FOR DELIVERY OF HETEROLOGOUS GENES

This is a continuation of PCT/IB99/01524, Filed Aug. 27, 1999, which claims the benefit of U.S. Provisional Application No. US60/098,028, Filed Aug. 27, 1998.

FIELD OF THE INVENTION

The present invention relates to effective targeting of adenovirus vectors by modifying surface accessible sites of the fiber or hexon proteins to include a targeting amino acid sequence. The key to success of the present invention lies in the discovery that additional spacer amino acid residues at the N-terminus and C-terminus of the inserted targeting sequence are critical to providing a recognizable binding structure of the targeting sequence. Thus, accessibility and functionality of the targeting sequence as well as structure of the modified protein strongly depend on the size and nature of the neighboring spacers. Other results suggest that short targeting peptides can be effectively fused to the C-terminus of the fiber protein. The invention further relates to the use of such vectors for delivering therapeutic genes to specific target cells in vitro and in vivo.

BACKGROUND OF THE INVENTION

Adenovirus Vectors

Adenoviruses exhibit certain properties which are particularly advantageous for use as vector for the transfer of genes in gene therapy. In particular, they have a fairly broad host spectrum, are capable of infecting quiescent cells, do not integrate into the genome of the infected cell, and have not been associated, up until now, with major pathologies in man. Adenoviruses have thus been used to transfer genes of interest into the muscle (Ragot et al., 1993, Nature 361:647), the liver (Jaffe et al., 1992, Nature Genetics 1:372), the nervous system (Akli et al., 1993, Nature Genetics 3:224), tumors (Griscelli et al., 1998, PNAS 95:6367), intact or injured vascular endotheliums (van Belle et al., 1998, Human Gene Therapy 9:1013), synovial tissue (Ghivizzani et al., 1998, PNAS 95:4613), and the like. Adenovirus vectors efficiently transfer genes to both replicating and non-replicating cells (see, e.g., Crystal, 1995, Science 270:404–410).

Adenovirus Capsid

Characteristics of the adenovirus capsid are well known (see, e.g. International Patent Publication WO 98/07877).

Various references describe the adenovirus hexon protein, and permit some estimation of accessible sites. For example, Athapilly et al. (1994, J. Mol. Biol. 242: 430–455) describes its refined crystal structure at 2.9A resolution. Crawford-Miksza et al. (1996, J. Virol. 70: 1836–1844) reports the location and structure of seven hexon protein hypervariable regions containing serotype-specific residues. Indeed, there has been a report of expression of a foreign epitope on the surface of the adenovirus hexon (Crompton et al., 1994, J. Gen. Virol. 75: 133–139). However, as shown in the examples, infra, the article by Crompton et al. does not teach a reproducible method of targeting adenovirus by modifying the hexon protein.

Additional references provide information about the fiber protein (Chroboczek et al., 1995, In Doerfler W. & P. Böhm (Eds.), *The molecular repertoire of adenoviruses*, pp. 163–200, Springer-Verlag; Stewart and Burnett, ibid., pp. 25–38; Xia et al., 1995, ibid., pp. 39–46Fender et al., 1995Virol., 214:110–117; Hong and Engler, 1996, J. Virol., 70: 7071–7078). Inhibition of cell adhesion to the virus by synthetic peptides of fiber knob of human adenovirus serotypes 2 and 3 and virus neutralization by anti-peptide antibodies has been reported (Liebermann et al., 1996, Virus Research, 45:111–121). Xia et al. (1994, Structure, 2:1259–1270) report the crystal structure of the receptor-binding domain of adenovirus type 5 fiber protein at 1.7 A resolution.

Adenoviruses are nonenveloped, regular icosahedrons of about 65 to 80 nm in diameter. The adenoviral capsid comprises 252 capsomers, of which 240 are hexons and 12 are pentons. The hexons and pentons are derived from three different viral polypeptides (Maizel et al., 1968, Virology, 36: 115–125; Weber et al., 1997, Virology: 76, 709–724. The Ad5 hexon comprises three identical polypeptides of 967 amino acids each, namely polypeptide II (Roberts et al., 1986, Science, 232: 1148–1151). The penton comprises a penton base, which provides a point of attachment to the capsid, and a trimeric fiber protein, which is noncovalently bound to and projects from the penton base.

The fiber protein comprises three identical proteinaceous subunits of polypeptide IV (582 amino acids) and comprises a tail, a shaft and a knob (Devaux et al., 1990, J. Molec. Biol., 215: 567–588). The fiber shaft comprises pseudorepeats of 15 amino acids, which are believed to form two alternating β-strands and β-bends (Green et al., 1983, EMBO J., 2: 1357–1365). The overall length of the fiber shaft and the number of 15 amino acid repeats varies between adenoviral serotypes. For example, the Ad2 fiber shaft is 37 nm long and comprises 22 repeats, whereas the Ad3 fiber is 11 nm long and comprises 6 repeats. Sequencing of over ten fiber proteins from different adenoviral serotypes has revealed a greater sequence diversity than that observed among other adenoviral proteins. For example, the knob regions of the fiber proteins from the closely related Ad2 and Ad5 serotypes are only 63% similar at the amino acid level (Chroboczek et al., 1992, Virology, 186: 280–285), whereas their penton base sequences are 99% identical. Ad2 and Ad5 fiber proteins, however, both likely bind to the same cellular receptor, since they cross-block each other's binding. In contrast, Ad2 and Ad3 fibers are only 20% identical (Signas et al., 1985, J. Virol., 53:672–678), and bind to different receptors (Defer et al., 1990, J. Virol., 64(8), 3661–3673).

Adenovirus serotype 2 has been shown to use the fiber and the penton base to interact with distinct cellular receptors to attach to and efficiently infect a cell (Wickham et al., 1993, Cell, 73: 309–319). First, the virus uses a receptor binding domain localized in the fiber knob (Henry et al., 1994, J. Virol., 68(8): 5239–5246) to attach to one of at least two cell-surface receptors (Hong et al., 1997, EMBO J., 16:2294–2306; Bergelson et al., 1997, Science, 275:1320–1323; Phillipson et al., 1968, J. Virol., 2: 1064–1075; Wickham et al., 1993 supra.; Svensson et al., 1981, J. Virol., 38: 70–81; and DiGuilmi et al., 1995, Virus Res., 38: 71–81). Then, following viral attachment, the penton base binds to a specific member of a family of heterodimeric cell-surface receptors called integrins. For the Ad2 and Ad5 serotypes, which possess the long-shafted fibers, the penton base is not significantly involved in the initial viral attachment to host cells (Wickham et al., 1993, supra).

Most integrins recognize short linear stretches of amino acids in a ligand, such as the tripeptide RGD, which is found in the majority of extracellular matrix ligands. The integrin $\alpha_{IIb}\beta_3$ binds fibrinogen via the amino acid sequence KQAGD (SEQ ID NO: 158) (Kloczewiak et al., 1984, Biochemistry, 23, 1767–1774), and $\alpha_4\beta_1$ binds fibronectin via the core sequence EILDV (SEQ ID NO: 159) (Komoriya et al., 1991, J. Biol. Chem., 266: 15075–15079). Another structural motif, NPXY (SEQ ID NO: 160), which is present in the β subunits of $\alpha_v$-containing integrins, also has been shown to be important for integrin-mediated internalization (Suzuki et al., 1990, Proc. Natl. Acad. Sci. USA, 87: 5354).

Once Ad2 or Ad5 attaches to a cell via its fiber, it undergoes receptor-mediated internalization into clathrin-coated endocytic vesicles by penton base binding to integrins. Ultimately, the viral particles are transported to the nuclear pore complex of the cell, where the viral genome enters the nucleus, thereby initiating expression from the virus chromosome.

A drawback to the use of adenovirus in gene therapy, however, is that all cells that comprise receptors for the adenoviral fiber and penton base will internalize the adenovirus, and, consequently, the gene(s) being administered—not just the cells in need of therapeutic treatment. Also, cells that lack either the fiber receptor or the penton base receptor will be impaired in adenoviral-mediated gene delivery. Cells that appear to lack an adenoviral fiber receptor, are transduced by adenovirus, if at all, with a very low efficiency (Curiel et al., 1992, supra; Cotton et al., 1990, Proc. Natl. Acad. Sci. USA, 87: 4033–4037; Wattel et al., 1996, Leukemia, 10:171–174). Accordingly, effectively directing adenoviral entry to specific cells and in some cases expanding the repertoire of cells amenable to adenovirus-mediated gene therapy, represents an important goal to improve current vectors. Both approaches also could potentially reduce the amount of adenoviral vector that is necessary to obtain gene expression in the targeted cells and, thus, potentially reduce side effects and complications associated with higher doses of adenovirus.

Adenovirus Targeting Strategies

Various strategies have been employed to modify adenovirus tropism, i.e., to target adenovirus to specific cell types not normally infected efficiently by wild-type adenovirus vectors (see, e.g., International Patent Publication WO 98/07877). Fiber protein, hexon protein, and penton base protein modification strategies have been employed.

U.S. Pat. No. 5,559,099 describes a recombinant virus comprising a chimeric penton base protein with a nonpenton amino acid sequence specific for a receptor, antibody, or epitope in addition to or in place of a wild-type penton base sequence, and a therapeutic gene.

U.S. Pat. No. 5,543,328 claims an adenovirus wherein the adenovirus fiber includes a ligand specific for a receptor located on a desired cell type. Such an adenovirus fiber can be prepared by removing all or a portion of the fiber protein head portion and replacing it with ligand, or by creating a fusion between a full length fiber protein and a ligand.

International Patent Publication WO 95/26412 discloses modification of adenovirus full length fiber protein to contain a C-terminial linker for attachment of a ligand. Inclusion of a linker is stated to avoid steric interference with formation of a fiber protein homotrimer.

International Patent Publication WO 96/26281 discloses a recombinant adenovirus comprising (a) a chimeric fiber protein with a nonnative amino acid sequence in addition to or in place of a native fiber sequence, (b) a therapeutic gene, and, optionally, (c) a nonnative trimerization domain in place of the native fiber amino acid trimerization domain. The nonnative amino acid sequence can be a protein binding sequence, and may be located at the C-terminus.

International Patent Publication WO 97/20051 discloses a chimeric adenovirus coat protein with a nonnative amino acid sequence that is able to direct vector entry into cells more efficiently than a vector with wild-type coat protein. The nonnative sequence can be inserted into or in place of an internal coat protein sequence, at or near the C-terminus of the coat protein, or in an exposed loop of the coat protein. The coat protein can be a fiber protein, a penton base protein, or a hexon protein. A spacer sequence can be included.

Other targeting techniques rely on post-expression modification of the viral coat protein, e.g., by covalent or noncovalent binding of bridging targeting groups or targeting groups (see, e.g., International Patent Application No. WO 97/05266; International Patent Publication WO 97/23608; International Patent Publication WO 97/32026).

Despite these efforts, there remains a need in the art to identify suitable modes of insertion of the binding peptide so that it is accurately displayed at the capsid surface to allow virus growth and specific binding to its cognate receptor(s).

There is a further need to define critical parameters that permit recognition of such sequences. Yet another need in the art is to provide specific targeting peptide sequences suitable for directing adenovirus vectors to target cells in vivo. These and other needs of the art are addressed by the present invention.

The citation of any reference herein should not be construed as an admission that such reference is available as "Prior Art" to the instant application. Each of the references disclosed herein is incorporated by reference in the application in its entirety.

SUMMARY OF THE INVENTION

The present invention advantageously provides an effective targeted adenovirus vector. The targeted vector of the invention is characterized by an appropriate deletion of amino acids from an effective site in either the hexon protein or the fiber protein.

Thus, in a more specific embodiment the invention relates to an adenovirus from which at least a part of the hexon HRV5 loop is replaced with a binding peptide, or targeting sequence, flanked by connecting amino acid spacers so as to functionnaly display its binding specificity at the capsid surface. In a specific embodiment the adenovirus comprises a deletion of about 6 to 17 amino acids from the hexon HVR5 loop preferably not exceeding 14 amino acids.

In an other specific embodiment the invention relates to an adenovirus from which at least a part of the fiber HI loop is replaced with a binding peptide, or targeting sequence, flanked by connecting amino acid spacers so as to functionnaly display its binding specificity at the capsid surface. In a specific embodiment the adenovirus comprises a deletion of about 6 to 17 amino acids from the hexon HI loop preferably not exceeding 11 amino acids.

In a further embodiment the invention relates to a recombinant adenovirus vector wherein a binding peptide, or targeting sequence, is connected to the C-terminus of the fiber by a connecting spacer, or linker, so as to functionaly display its binding specificity at the capsid surface.

In a more specific embodiment, about 13 amino acids are deleted from the hexon HVR5 loop corresponding to about amino acid residue 269 to about amino acid residue 281 of adenovirus serotype 5 (Ad5). In another specific embodiment, about 11 amino acids are deleted from the fiber protein HI loop corresponding to about amino acid residue 538 to about amino acid residue 548 of adenovirus serotype 5 (Ad5). A targeting peptide is inserted at the site of the deletion. A particular advantage of the invention is the discovery that the targeting peptide sequence should be connected by a first spacer at the N-terminus and a second spacer at the C-terminus of the targeting sequence, wherein the spacers comprise a flexible amino acid residue. Preferably, the first spacer or the second spacer, or both, comprises an amino acid selected from the group consisting of glycine and serine.

In a specific aspect, the targeted adenovirus modified in the hexon protein advantageously employs dipeptide spacers consisting of flexible amino acid residues. In a specific embodiment, the first and second spacers are a Gly-Ser dipeptide. In a further specific embodiment of this aspect, the first spacer is a glycine residue.

In an aspect of the invention in which the fiber protein HI loop is modified, the first and second spacers are advantageously tri-peptides consisting of flexible amino acid residues. In a specific embodiment of this aspect of the invention, the first and second spacers are a Gly-Ser-Ser tri-peptide.

Preferably, the targeting sequence is a ligand epitope for a urokinase-type plasminogen activator receptor (UPAR). In particular, the targeting sequence can be selected from the group consisting of LNGGTCVSNKYFSNIHWCN (SEQ ID NO: 1); LNGGTAVSNKYFSNIHWCN (SEQ ID NO: 2); AEPMPHSLNFSQYLWT (SEQ ID NO:3); AEPMPHSLNFSQYLWYT (SEQ ID NO: 4); RGHSRGRNQNSR (SEQ ID NO: 5); and NQNSRRPSRA (SEQ ID NO: 6).

In an alternative embodiment in which the hexon protein is modified, the targeting sequence including the spacers is selected from the group consisting of:
gly-ser-LNGGTCVSNKYFSNIHWCN-gly-ser (SEQ ID NO: 7);
gly-ser-LNGGTAVSNKYFSNIHWCN-gly-ser (SEQ ID NO: 8);
gly-ser-AEPMPHSLNFSQYLWT-gly-ser (SEQ ID NO:9);
gly-ser-AEPMPHSLNFSQYLWYT-gly-ser (SEQ ID NO:10);
gly-ser-RGHSRGRNQNSR-gly-ser (SEQ ID NO: 11);
gly-ser-NQNSRRPSRA-gly-ser (SEQ ID NO:12);
gly-ser-CDCRGDCFC-gly-ser (SEQ ID NO:13);
gly-ser-DCRGDCF-gly-ser (SEQ ID NO:14); and
gly-ser-KKKKKKK-gly-ser (SEQ ID NO:15).

In an alternative embodiment in which the fiber protein is modified, the targeting sequence including the spacers is selected from the group consisting of:
gly-ser-ser-LNGGTCVSNKYFSNIHWCN-gly-ser-ser (SEQ ID NO:16);
gly-ser-ser-LNGGTAVSNKYFSNIHWCN-gly-ser-ser (SEQ ID NO:17);
gly-ser-ser-AEPMPHSLNFSQYLWT-gly-ser-ser (SEQ ID NO:18);
gly-ser-ser-AEPMPHSLNFSQYLWYT-gly-ser-ser (SEQ ID NO:19);
gly-ser-ser-RGHSRGRNQNSR-gly-ser-ser (SEQ ID NO:20);
gly-ser-ser-NQNSRRPSRA-gly-ser-ser (SEQ ID NO:21:);
gly-ser-ser-CDCRGDCFC-gly-ser-ser (SEQ ID NO:22);
gly-ser-ser-DCRGDCF-gly-ser-ser (SEQ ID NO:23);
gly-ser-ser-KKKKKKK-gly-ser-ser (SEQ ID NO:24)
ser-ser-RGHSRGRNQNSRRPSRA-gly-ser (SEQ ID NO:143);
tyr-glu-RGHSRGRNQNSR-gly-ser (SEQ ID NO:144);
tyr-gln-glu-RGHSRGRNQNSR-gly-ser (SEQ ID NO: 145);
ser-ser-ser-RGHSRGRNQNSR-gly-ser (SEQ ID NO: 146); and
ser-ser-RGHSRGRNQNSR-gly-gly (SEQ ID NO: 147).

Preferably the connecting spacer or linker comprises an amino acid selected from the group consisting of glycine, serine, threonine, alanine, cysteine, aspartate, asparagine, methionine and proline. In a refered embodiment the first amino acid in the spacer is a proline.

The recombinant adenovirus can be derived from a human adenovirus serotype, in particular from human adenovirus subgroup C, such as human adenovirus serotype 5.

The fiber protein can be modified to have a fiber shaft that is shorter than a wild-type fiber shaft, in particular by an in-frame deletion or by replacing it with the shaft from another serotype. The fiber shaft can be from subgroup C and comprises an in-frame deletion encompassing repeats 4 to 16 or repeats 4 to 19 or from subgroup C and has been shortened by replacing it with the shaft from serotype 3 (Ad3)

According to either aspect of the invention (modification of the hexon or the fiber), the fiber protein can be modified to be shorter than in the wild-type sequence. For example, the fiber protein can be modified to contain only repeats 1 to 3 and 17 to 22 of Ad5; repeats 1 to 3 and 20 to 22 of Ad5; or an adenovirus serotype 3 (Ad3) shaft in place of the endogenous Ad5 shaft.

In a specific embodiment, exemplified infra, the adenovirus is a serotype 5 adenovirus.

In a further embodiment, the present invention provides a specific targeted adenovirus vector comprising a linker peptide and a targeting peptide at the C-terminus of the fiber protein.

Preferably, the targeting sequence is a ligand for a UPAR, such as CD87, a peptide fragment from FGF-1 binding to heparin, comprising between 7 and 15 amino acids, is composed of 5 to 10 lysine residues, preferably of almost 7 lysine residues, or is composed of between 5 and 10 Arg-Arg and Leu-Leu motifs.

Preferably, the targeting sequence is selected from the group consisting of LNGGTCVSNKYFSNIHWCN (SEQ ID NO: 1); LNGGTAVSNKYFSNIHWCN (SEQ ID NO: 2); AEPMPHSLNFSQYLWT (SEQ ID NO: 3); AEPMPHSLNFSQYLWYT (SEQ ID NO:4); RGHSRGRNQNSR (SEQ ID NO:5); NQNSRRPSRA (SEQ ID NO:6); RRLLRRLLRR (SEQ ID NO: 133); and KRGPRTHYGQK (SEQ ID NO: 134);

Preferably the linker peptide comprises the sequences PKRARPGS (SEQ ID NO: 149) and the targeting sequence including the linker peptide comprises the sequences PKRARPGSKKKKKKK (SEQ ID NO: 132), PKRARPGSRRLLRRLLRR (SEQ ID NO: 141) or PKRARPGSKRGPRTHYGOK (SEQ ID NO: 140).

Naturally, given the targeted adenoviruses disclosed above and in greater detail herein, the present invention provides a method for modifying the cellular tropism of an adenovirus vector, comprising deleting a native amino acid sequence from a site in a capsid protein of the adenovirus; and inserting a targeting peptide sequence connected by a first spacer at the N-terminus and a second spacer at the C-terminus of the targeting sequence, wherein the spacers comprise a flexible amino acid residue. According to this aspect of the invention, the targeting peptide is inserted in a deletion site selected from the group consisting of about 13 amino acids from the hexon HVR5 loop corresponding to about amino acid residue 269 to about amino acid residue 281 of adenovirus Ad5; and about 11 amino acids from the fiber protein HI loop corresponding to about amino acid residue 538 to about amino acid residue 548 of Ad5. In a preferred embodiment, the first spacer comprises an amino acid selected from the group consisting of glycine and serine. In another preferred embodiment, the second spacer comprises an amino acid selected from the group consisting of glycine and serine.

Are also encompassed by the present invention:

- an adenovirus hexon comprising a deletion of about 13 amino acids from the HVR5 loop corresponding to about amino acid residue 269 to about amino acid residue 281 of adenovirus serotype 5 (Ad5) and an insertion at the site of the deletion of a targeting peptide sequence connected by a first spacer at the N-terminus and a second spacer at the C-terminus of the targeting sequence, wherein the first and second spacers comprise a flexible amino acid residue.
- an adenovirus fiber protein comprising a deletion of about 11 amino acids from the HI loop corresponding to about amino acid residue 538 to about amino acid residue 548 of adenovirus serotype 5 (Ad5) and an insertion at the site of the deletion of a targeting peptide sequence connected by a first spacer at the N-terminus and a second spacer at the C-terminus of the targeting sequence, wherein the first and second spacers comprise a flexible amino acid residue.
- an adenovirus fiber protein comprises a linker peptide and a targeting peptide at its C-terminus.

The invention further specifically provides a method for targeting cells that express a urokinase-type plasminogen activator receptor (UPAR). In particular, this method comprises using adenoviruses modified to expose at the capsid surface the specific UPAR targeting peptides disclosed above. Alternatively, the invention provides for modifying the hexon HVR5 loop or the fiber protein HI loop by inserting the specific sequences, including spacer groups, defined above.

The method for targeting a specific cell type in accordance with the invention can be further enhanced by shortening the fiber protein shaft, e.g., such that the fiber shaft only contains repeats 1 to 3 and 17 to 22 of Ad5; repeats 1 to 3 and 20 to 22 of Ad5; or with an Ad3 shaft. Repeats are as described by Chroboczek et al (1995, Current Topics in Microbiology and Immunology, Springer Verlag, 199 :163–200).

The invention further provides a method for preferentially expressing a gene in a target cell comprising contacting a population of cells containing the target cell with the targeted adenovirus vector of the invention, wherein the targeting sequence is a ligand epitope for a receptor on the target cell. In particular, the invention provides a method for preferentially expressing a gene in a target cell that expresses a UPAR comprising contacting a population of cells containing the target cell with the targeted adenovirus vectors of the invention that are modified to display a UPAR binding peptide. In this embodiment, the targeted adenovirus vector preferably comprises a heterologous therapeutic gene or nucleic acid for transduction of actively dividing and/or motile cells, including tumor cells and its metastases, tumor vasculature, activated endothelial cells, activated smooth muscle cells . . . However, UPAR targeted vectors can also be considered as candidate vectors for transduction of other tissues as muscle, brain, heart, etc. More particularly, the nucleic acid encodes a therapeutic polypeptide which acts as an angiogenesis inhibitor, an angiogenic factor, a conditional suicide effector, a tumor suppressor, a growth-arrest protein (GAX), or any secreted polypeptide.

In particular, the invention provides a method for preferentially expressing a gene in a target cell that expresses an integrin comprising contacting a population of cells containing the target cell with the targeted adenovirus vector of the invention that are modified to display an integrin binding peptide. In this embodiment, the targeted adenovirus vector preferably comprises a therapeutic gene or nucleic acid for transduction of actively dividing and/or motile cells, including tumor cells and its metastases, tumor vasculature, activated endothelial cells, activated smooth muscle cells . . . However, integrin targeted vectors can also be considered as candidate vectors for transduction of other tissues as skeletal muscle, brain, heart, hematopoietic cells, ischemic tissues, etc. More particularly, the nucleic acid encodes a therapeutic polypeptide which acts as an angiogenesis inhibitor, an angiogenic factor, a conditional suicide effector, a tumor suppressor, a growth-arrest protein (GAX), a cell survival-promoting factor (in particular members of the Akt/PKB family) or any secreted polypeptide.

Thus a further object of the present invention is a method for the treatment of a disease by gene therapy comprising the step of administering a targeted adenovirus vector as disclosed hereabove, or obtained according to the method disclosed hereabove.

Still an object of the present invention is a medecine containing a targeted adenovirus vector as disclosed hereabove, or obtained according to the method as disclosed hereabove and the use of such a targeted adenovirus vector for manufacturing a medecine for the treatment of a disease by gene therapy. A further object of the present invention is a pharmaceutical composition containing such targeted adenovirus vectors and a efficient quantity of a pharmaceutically active excipient.

Thus, an object of the invention is to provide for tropism-modified adenovirus vectors without adversely impacting productivity of the vectors.

A further object of the invention is to identify suitable mode of insertion so that the binding peptide is accessible and effectively recognizes its specific receptors.

Still another object of the invention is to identify the number of amino acid residues that can be deleted from the native adenovirus capsid protein so that the targeting peptide sequence can be effectively inserted.

Yet another object of the invention is to provide the effective size and characteristics of spacer sequences to be included at the ends of the inserted targeting peptide to permit adoption by the targeting peptide of an accessible conformation that permits effective binding to the target receptor.

These and other objects of the invention are further provided by the accompanying Drawings and the following Detailed Description of the Invention.

BRIEF DESCRIPTION OF THE DRAWINGS

FIGS. 14A and 14B:: Infection of Hs578T with virus viruses BC15X (A) and AE43 (B) preincubated with increasing doses of soluble uPAR.

DETAILED DESCRIPTION OF THE INVENTION

Figure 1:
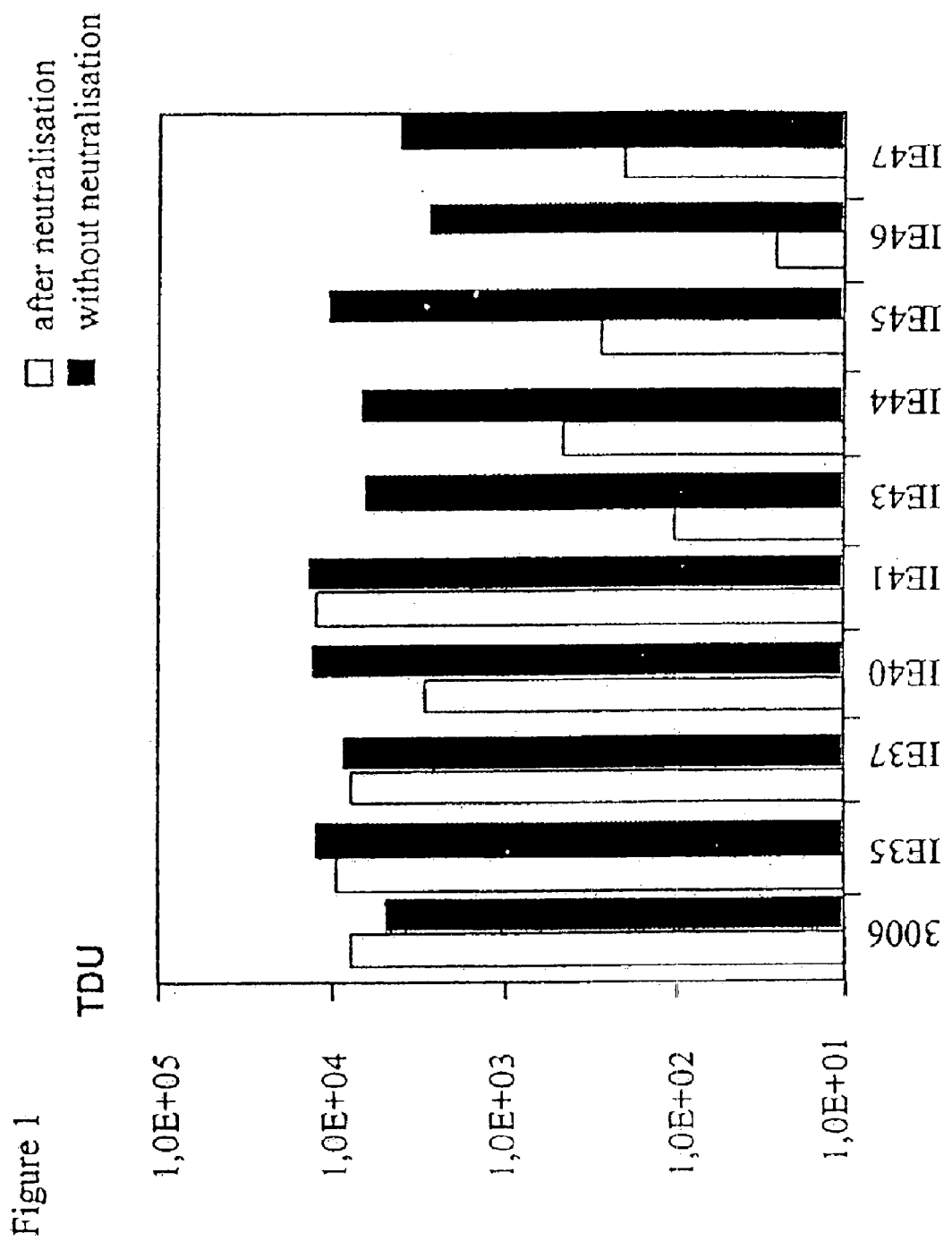
FIG. 1. Neutralization assay on W162 cells with virus modified in the hexon HVR5 region.

As noted above, there has been keen interest in the art to modify adenovirus tropism so as to permit targeting adenovirus vectors to specific target cells, including those cells that are not efficiently infected by adenoviruses. While there have been some successes in achieving this goal, the present inventors recognized that a practical solution to this problem, i.e., a solution that would not adversely affect viral productivity and that would permit a satisfactory increase in cell specificity, had not been achieved. In particular, optimum sites for incorporation of a targeting peptide in a viral capsid protein, the size of a deletion from the native capsid protein (if any), the size of an inserted targeting sequence, and the presence and nature of any linker sequences joining the targeting sequence to the capsid protein, are not described in the prior art. The present invention advantageously addresses these issues, and provides highly effective targeting by: providing optimized sites for insertion of a targeting sequence, including the size of the native sequence to be deleted to make room for the targeting peptide; identifying an appropriate size for the targeting sequence; and disclosing the size and characteristics of linkers that permit accessibility and specific recognition of the targeting peptide; and identifying interesting cell marker as a target receptor.

In particular, the present inventors set out to introduce an accessible foreign peptide on the surface of the adenoviral capsid, and thus to modify the natural tropism of the virus. With this in mind, a series of constructs with modified hexons or fibers incorporating a neutralizing epitope from poliovirus type 1 were designed. The poliovirus sequence was chosen as cognate neutralizing antibodies were readily available to document in great details its accessibility and functionality.

Modification of the hexon and fiber to restrict infection to specific target cells requires that the adenovirus fiber not be able to efficiently interact with its native cellular receptors. In the case of hexon modified capsid, it also requires that the binding peptide can interact directly with its cognate receptor on the cell surface without steric hindrance from the fiber. For these purposes, the possibility of shortening the shaft of the fiber was investigated.

The invention is based, in part, on experiments that identified sites suitable for insertion of functional targeting sequences in the hexon protein and in the fiber protein. It was discovered that replacement of a portion of the hexon HVR5 loop and fiber HI loop permitted insertion of targeting sequences without adversely affecting viral productivity. Furthermore, the data showed that incorporation of flexible linker peptides at the ends of the inserted sequences was critical to accessibility or recognition of the targeting sequence. Moreover, incorporation of ligands specific for uPAR or for some integrins was successfully achieved in terms of accessibility of the ligand, productivity of the modified viruses, transduction efficiency of the target cell types as shown in in vitro and in vivo experiments. Finally, it was also shown that shortening of the fiber efficiently reduces virus affinity for natural host cell, which makes this strategy attractive for ablation of natural tropism of Ad5.

In a preferred embodiment, the different approaches are combined. Preferably, the fiber protein is shortened in a virus having a modified hexon HVR5 loop or fiber HI loop. In a further example, a virus with a shortened fiber could have an insertion in HVR5 or in HI to target UPAR as the primary step of the infection, and an insertion in HI loop or in HVR5 (respectively) to target an integrin to favor the internalization of the virus in the endosome. Any suitable membrane receptor can also be targeted using the same strategy, i.e. incorporation of high affinity ligands in the hexon and/or the fiber in combination with shortening of the fiber.

The Detailed Description of the Invention is further elaborated in sections relating to specific definitions, adenovirus vectors, targeting peptide sequences, and uses of the targeted adenovirus vectors. The various headers and organization of the sections are provided for the sake of clarity and convenience, and are not in any way to be deemed limiting.

Definitions

Various terms are used throughout the specification and claims. Where not otherwise defined, the following definitions apply:

As used in the art, a <<vector>> is any means for the transfer of a nucleic acid according to the invention into a host cell. For purposes of the present invention, the term vector is used to modify "adenovirus" so as to reflect that the adenovirus has been genetically engineered to transfer a nucleic acid of interest (a gene under control of, or operably linked to, an expression control sequence) into the target cell. Adenovirus vectors of the invention are described in greater detail, infra.

A cell has been "transfected" or "infected" by an adenovirus vector of the invention when viral DNA has been introduced inside the cell. A cell has been "transformed" by exogenous or heterologous DNA when the transfected DNA effects a phenotypic change.

The term "corresponding to" is used herein to refer similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases. Examples include hexon proteins or fiber proteins from other adenovirus serotypes (2, 3, etc.) besides the type 5 adenovirus (Ad5) exemplified herein. Those of ordinary skill in the art are familiar with homologous adenovirus capsid proteins.

In other words, the present invention provides for modification of homologous capsid proteins from other adenovirus species using the optimized parameters defined herein for Ad5. As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667). Such proteins (and their encoding genes) have sequence homology, as reflected by their high degree of sequence similarity.

The term "deletion" refers to the removal of native amino acid residues from a defined region of an adenovirus capsid protein, i.e., a hexon or fiber protein. According to the invention, a preferred size for such a deletion is between about 10 and about 20 amino acids. More preferably, the size of the deletion is between about 10 and about 15 amino acids. In specific embodiments, 11 and 13 amino acid sequences were deleted.

The term "spacer" or "spacer peptide" or <<linker>> or <<linker peptide>> is used herein to refer to a sequence of about one to about three amino acids that is included to connect the binding peptide to its capsid carrier protein. The spacer or the linker is preferably made up of amino acid residues with high degrees of freedom of rotation, which permits the targeting peptide to adopt a conformation that is recognized by its binding partner (e.g., receptor). Preferably no more than three amino acids are included in the spacer; more preferably, the spacer consists of two amino acids. Preferred amino acids for the spacer are glycine and serine. In specific embodiments, the spacer is a peptide having the sequence Gly-Ser or Gly-Ser-Ser.

As used herein, the term "about" or "approximately" means within 20%, preferably within 10%, and more preferably within 5% of a given value or range.

Adenovirus Vectors

Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mavl, Beard et al., Virology 75 (1990) 81), ovine, porcine, avian, and simian (example: SAV) origin. Preferably, the adenovirus of animal origin is a canine adenovirus, more preferably a CAV2 adenovirus (e.g., Manhattan or A26/61 strain (ATCC VR-800)).

Adenoviral vectors are commonly used for in vitro, in vivo or ex vivo transfection and gene therapy procedures. Preferably, the adenoviral vectors are replication defective, that is, they are unable to replicate autonomously in the target cell. In general, the genome of the replication defective viral vectors within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to a region required for virus propagation. Such techniques may be performed in vitro (on the isolated DNA) or in situ, using the techniques of genetic manipulation or by treatment with mutagenic agents. For purposes of the present invention, the replication defective virus retains the sequences of its genome which are necessary for encapsidating the viral particles. Defective viruses, which entirely or almost entirely lack viral genes, may also be used.

The replication defective adenoviral vectors of the invention comprise at least the ITRs, an encapsidation sequence and the nucleic acid of interest. Preferably, at least the E1 region of the adenoviral vector is rendered non-functional. The deletion in the E1 region preferably extends from nucleotides 455 to 3329 in the sequence of the Ad5 adenovirus (PvuII-BglII fragment) or 382 to 3446 (HinfII-Sau3A fragment), or 382–3512 (HinfI-RsaI fragment). Other regions may also be modified, in particular the E3 region (WO95/02697), the E2 region (WO94/28938), the E4 region (WO94/28152, WO94/12649 and WO95/02697), the IVa2 region (WO96/10088) or in any of the late genes L1–L5.

In a preferred embodiment, the adenoviral vector has a deletion in the E1 region (Ad 1.0). Examples of E1-deleted adenoviruses are disclosed in EP 185,573, and in FR 97/14383, filed 11, Nov. 1997, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which an E4 functional region and the nucleic acid sequence are inserted (see FR94 13355, the contents of which are incorporated herein by reference). Another adenovirus vector for use in the invention is described in WO 96/10088.

The replication defective recombinant adenoviruses according to the invention can be prepared by any technique known to the person skilled in the art (Levrero et al., 1991, Gene 101: 195; EP 185 573; Graham, 1984, EMBO J. 3: 2917). In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., 1977, J. Gen. Virol. 36: 59) which contains the left-hand portion of the genome of an Ad5 adenovirus (12%) integrated into its genome, PER.C6 (Bout et al., 1997, Cancer Gene Therapy 4:324; Fallaux et al, 1998, Hum Gen Ther 9: 1909–1917), and cell lines which are able to complement the E1 and E4 functions, as described in applications WO94/26914 and WO95/02697. In a preferred embodiment, an *E. coli* vector system is used to generate the adenovirus backbone (International Patent Publication WO 96/25506; Crouzet et al. 1997, Proc. Natl. Acad. Sci. 94:1414–1419).

Indeed, the general techniques for preparing adenoviruses of the invention are well known in the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. ÊHiggins eds. (1985)]; *Transcription And Translation* [B. D. Hames & S. J. Higgins, eds. (1984)]; *Animal Cell Culture* [R. I. Freshney, ed. (1986)]; *Immobi-*

*lized Cells And Enzymes* [IRL Press, (1986)]; B. ÊPerbal, *A Practical Guide To Molecular Cloning* (1984); F. M. Ausubel et al. (eds.), *Current Protocols in Molecular Biology*, John Wiley & Sons, Inc. (1994). Incorporation of cassette insertion sites, whether for insertion of a heterologous gene or for insertion of the targeting sequence in the hexon or fiber protein (as exemplified infra) facilitates such genetic manipulations. A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

Recombinant adenoviruses are recovered and purified using standard molecular techniques, which are well known to one of ordinary skill in the art (see, e.g., International Patent Publication WO 98/00524, International Patent Publication WO 96/27677; and International Patent Publication WO 97/08298).

Expression of heterologous genes by adenovirus vectors of the invention. The adenovirus vectors of the invention preferably contain a DNA coding sequence for a heterologous gene. A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence. A coding sequence is "under the control" of transcriptional and translational control sequences in a cell when RNA polymerase transcribes the coding sequence into mRNA, which is then trans-RNA spliced and translated into the protein encoded by the coding sequence. In another embodiment, the nucleic acid of interest is not translated into a polypeptide but acts as a specific anti-sense therapeutic molecule, or as a therapeutic decoy.

Transcriptional and translational control sequences are DNA regulatory sequences, such as promoters, enhancers, terminators, and the like, that provide for the expression of a coding sequence in a host cell. In eukaryotic cells, polyadenylation signals are control sequences. A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

Expression of a heterologous protein may be controlled by any promoter/enhancer element known in the art, but these regulatory elements must be functional in the target cell selected for expression. Promoters which may be used to control gene expression include, but are not limited to, the cytomegalovirus immediate early (CMV-IE or CMV) promoter, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in embryonic liver and hepatomas (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

A "signal sequence" is included at the beginning of the coding sequence of a protein to be exported at the cell surface, or secreted. This sequence encodes a signal peptide, N-terminal to the mature polypeptide, that directs the host cell to translocate the polypeptide into the secretion pathway/compartment. The term "translocation signal sequence" is used herein to refer to this sort of signal sequence. Translocation signal sequences can be found associated with a variety of proteins native to eukaryotes and prokaryotes, and are often functional in both types of organisms.

Specific heterologous genes are discussed in the section relating to uses of the vectors of the invention, infra.

Targeting Peptide Sequences

Any known targeting sequence can be incorporated in a hexon HVR5 loop or fiber protein in accordance with the present invention. Examples of targeting peptides are ample in the literature. In general, any peptide ligand can provide a targeting sequence based on the receptor-binding sequence of the ligand. In immunology, such a sequence is referred to as an epitope, and the term epitope may be used herein to refer to the sequence of a ligand recognized by a receptor. Specifically, the term "ligand epitope of a receptor" refers to the sequence of a protein or peptide that is recognized by a binding partner on the surface of a target cell, which for the sake of convenience is termed a receptor. However, it should be understood that for purposes of the present invention, the term "receptor" encompasses signal-transducing receptors (e.g., receptors for hormones, steroids, cytokines, insulin, and other growth factors), recognition molecules (e.g., MHC molecules, B- or T-cell receptors), nutrient uptake receptors (such as transferrin receptor), lectins, ion channels, adhesion molecules, extracellular matrix binding proteins, and the like that are located and accessible at the surface of the target cell. Targeting peptides of the invention can bind to polypeptide or carbohydrate moieties on such receptors.

The size of the targeting peptide can vary within certain parameters. As shown in the examples, inserting peptides longer than the deleted sequence did not adversely impact viral productivity. Thus, the invention contemplates using a targeting sequence that is several fold longer than the deleted segment; preferably, the inserted peptide is no more than 200% longer than the deleted segment, and more preferably the inserted peptide is about the same size as the deleted segment.

Due to the degeneracy of nucleotide coding sequences, other DNA sequences which encode substantially the same amino acid sequence as a targeting peptide sequence may be used in the practice of the present invention. These include but are not limited to allelic variants, homologous variants from other species, variants in which a conservative amino acid substitution is effected, and variants in which a highly polymorphic amino acid residue (which is presumably not important for binding specificity) is changed. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to significantly affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $CONH_2$ can be maintained.

Such variants may be encoded by highly similar nucleic acids. Such nucleic acids will, in general, hybridize to a nucleic acid (including an oligonucleotide probe) that encodes the native amino acid sequence. As demonstrated in the examples, infra, various modifications can be introduced by single base changes that do not affect hybridization (of PCR primers), but that can create an endonuclease cleavage site or a altered amino acid residue.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; preferably at least about 15 nucleotides; and more preferably the length is at least about 20 nucleotides. In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

Integrin-binding peptides. Targeting peptide sequences include the well known integrin-binding peptides (see, e.g., U.S. Pat. No. 4,517,686; U.S. Pat. No. 4,589,881; U.S. Pat. No. 4,661,111; U.S. Pat. No. 4,578,079; U.S. Pat. No. 4,614,517; U.S. Pat. No. 5,453,489; U.S. Pat. No. 5,627,263). Other useful targeting peptides are described in International Patent Publication WO 98/17242 and European Patent Application EP 773 441.

Concerning the targeting of integrins, as noted above there are many publications describing peptides that bind specific integrins, some of which are overexpressed in different tumor or cell types. In a specific embodiment, αv integrins (and consequently actively dividing and/or motile cells including tumor cells and its metastases, tumor vasculature, activated endothelial, activated smooth muscle cells, skeletal muscle cells, etc.) are targeted, e.g., through a peptide selected by phage display. Naturally, any peptide specific of integrins, e.g., as described in the literature, can be used in the invention. The targeting of integrins could also favor the internalization of the virus, and could be a mean to restore the infectivity of Ad with shortened fibers.

Urokinase receptor targeted peptides. In a specific embodiment exemplified infra, peptides that target a receptor for urokinase-type plasminogen activator (UPAR; e.g., CD87) were selected from various publications. Naturally, there is a much more exhaustive list of peptides binding a UPAR. Any peptide binding UPAR could be used. Basic targeting peptides. Specific embodiments of the invention, with particular targeting peptides, are described in detail in Examples 4–6, infra. For example, a targeting peptide comprising primarily basic amino acid residues, e.g., lysine, arginine, and histidine, and more preferably either lysine or arginine, or both (see, e.g., WO 97/20051) was used in the examples, infra. In another example, ligands binding to heparan sulfate proteoglycans such as the arginine-leucine repeated motif RRLLRRLLRR (SEQ ID NO: 133), described in the RPR patent application WO95/21931, and the peptide fragment KRGPRTHYGQK (SEQ ID NO: 134) from the FGF-1 binding domain to heparin (Digabriele et al, 1998, Science, 393:812–817) were used.

Also, sequences that bind to heparin or glycosaminoglycans may be involved in binding to a heparin-like receptor (Sawitzky et al., 1993, Med. Microbiol. Immunol., 182: 285–92). Similarly, so-called <<heparin binding sequences>> may mediate the interaction of the peptide or protein in which they are contained with other cell surface binding sites, such as with cell surface heparan sulfate proteoglycan (Thompson et al., 1994, J. Biol. Chem., 269: 2541–9).

Alternatively, the targeting amino acid sequence comprises two basic amino acids (frequently Arg) located about 20 Angstroms apart, facing in opposite directions of an alpha helix (Margalit et al., 1993, J. Biol. Chem., 268: 19228–31; Ma et al., 1994, J. Lipid Res., 35: 2049–2059). Other basic amino acids can be dispersed between these two residues, facing one side, while nonpolar residues face the other side, forming a helical amphipathic structure with basic residues segregated to one side.

Also, the targeting sequence can comprise common heparin binding motifs present in fibronectin and heat shock proteins (Hansen et al., 1995, Biochim. Biophys. Acta, 1252: 135–45); insertions of 7 residues of either Lys or Arg, or mixtures of Lys and Arg (Fromm et al., 1995, Arch. Biochem. Biophys., 323: 279–87); the common basic C-terminal region of IGFBP-3 and IGFBP-5 of about 18 amino acids and which comprises a heparin binding sequence (Booth et al., 1995, Growth Regul., 5: 1–17); either one or both of the two hyaluronan (HA) binding motifs located within a 35 amino acid region of the C-terminus of the HA receptor RHAMM (Yang et al., 1994, J. Cell Biochem., 56: 455–68); a synthetic peptide (Ala347-Arg361) modeled after the heparin-binding form of *Staphylococcus aureus* vitronectin comprising heparin-binding consensus sequences (Liang et al., 1994, J. Biochem., 116: 457–63); any one or more of five heparin binding sites between amino acid 129 and 310 of bovine herpesvirus 1 glycoprotein gIII or any one of four heparin binding sites between amino acids 90 and 275 of pseudorabies virus glycoprotein gIII (Liang et al., 1993, Virol., 194: 233–43); amino acids 134 to 141 of pseudorabies virus glycoprotein gIII (Sawitzky et al., 1993, Med. Microbiol. Immunol., 182: 285–92); heparin binding regions corresponding to charged residues at positions 279–282 and 292–304 of human lipoprotein lipase (Ma et al., supra); a synthetic 22 residue peptide, N22W, with a sequence modeled after fibronectin and which exhibits heparin binding properties (Ingham et al., 1994, Arch. Biochem. Biophys., 314: 242–246); the motif present in the ectodomain zinc binding site of the Alzheimer beta-amyloid precursor protein (APP), as well as various other APP-like proteins, which modulates heparin affinity (Bush et al, 1994, J. Biol. Chem., 229: 26618–21), 8 amino acid residue peptides derived from the cross-region of the laminin A chain (Tashiro et al., 1994, Biochem. J., 302: 73–9); peptides based on the heparin binding regions of the serine protease inhibitor antithrombin III including peptides F123-G148 and K121-A134 (Tyler-Cross et al., 1994, Protein Sci., 3: 620–7); a 14 K N-terminal fragment of APP and a region close to the N-terminus (i.e., residues 96–110) proposed as heparin binding regions (Small et al., 1994, J. Neurosci., 14: 2117–27); a stretch of 21 amino acids of the heparin binding epidermal growth factor-like growth factor (HB-EGF) characterized by a high content of lysine and arginine residues (Thompson et al., 1994, J. Biol. Chem;., 269: 2541–9); a 17 amino acid region comprising the heparin binding region of thrombospondin and corresponding to a hep 1 synthetic peptide (Murphy-Ullrich et al., 1993, J. Biol. Chem., 268: 26784–9); a 23 amino acid sequence (Y565-A587) of human von Willebrand factor that binds heparin (Tyler-Cross et al., 1993, Arch. Biochem. Biophys., 306: 528–33); the fibronectin-derived peptide PRARI, and larger peptides comprising this motif, that bind heparin (Woods et al., 1993, Mol. Biol. Cell., 4:605–613); the heparin binding region of platelet factor 4 (Sato et al., Jpn. J. Cancer Res., 84: 485–8); and K18K sequence in the fibroblast growth factor receptor tyrosine kinase transmembrane glycoprotein (Kan et al., 1993, Science259: 1918–21).

Identification of targeting peptide sequences. In another embodiment, targeting peptides can be derived from various types of combinatorial libraries, using well known strategies for identifying ligands (see U.S. Pat. No. 5,622,699 and International Patent Application No. PCT/US96/14600). One approach uses recombinant bacteriophage to produce large libraries. Using the "phage method" (Scott and Smith, 1990, Science 249:386–390; Cwirla, et al., 1990 Proc. Natl. Acad. Sci., 87:6378–6382; Devlin et al., 1990, Science, 249:404–406), very large libraries can be constructed ($10^6$–$10^8$ chemical entities). A second approach uses primarily chemical methods, of which the Geysen method [Geysen et al., 1986, Molecular Immunology 23:709–715; Geysen et al., 1987, J. Immunologic Method 102:259–274) and the method of Fodor et al. (1991, Science 251:767–773) are examples. Furka et al. (1988, 14th International Congress of Biochemistry, VolumeÊ5, Abstract FR:013; Furka, 1991, Int. J. Peptide Protein Res. 37:487–493), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as targeting sequences. In another aspect, synthetic libraries (Needels et al., 1993, Proc. Natl. Acad. Sci. USA 90:10700–4; Ohlmeyer et al., 1993, Proc. Natl. Acad. Sci. USA 90:10922–10926; Lam et al., International Patent Publication No. WO 92/00252; Kocis et al., International Patent Publication No. WO 9428028), and the like can be used to screen for targeting peptides.

Uses of the Vectors of the Invention

The references provided above regarding preparation of adenovirus vectors describe various uses for such vectors.

Targeted introduction of therapeutic genes into malignant cells in vivo can provide an effective treatment of tumors. Several treatment modalities have been attempted. For example, one treatment involves the delivery of normal tumor suppressor genes (e.g., p53, retinoblastoma protein, p16, etc.) and/or inhibitors of activated oncogenes into tumor cells. A second treatment involves the enhancement of immunogeneity of tumor cells in vivo by the introduction of cytokine genes. A third treatment involves the introduction of genes that encode enzymes capable of conferring to the tumor cells sensitivity to chemotherapeutic agents. The herpes simplex virus-thymidine kinase (HSV-tk) gene can specifically convert a nucleoside analog (ganciclovir) into a toxic intermediate and cause death in dividing cells. It has recently been reported by Culver et al. (*Science,* 1992, 256:1550–1552) that after delivery of the HSV-tk gene by retroviral transduction, subsequent ganciclovir treatment effectively caused brain tumor regression in laboratory animals. U.S. Pat. No. 5,631,236 by Woo et al. describes gene therapy for solid tumors with an adenovirus vector that encodes HSV-tk or VZV-tk.

In a preferred embodiment, a vector of the invention can be used to target a nucleic acid of interest to the tumor itself, its metastases or the tumor vasculature, e.g. by using peptides that bind to a UPAR. In a preferred embodiment, such vectors encode genes for inhibitors of angiogenesis or an anti-angiogenic factor. An "anti-angiogenic factor" is a molecule that inhibits angiogenesis, particularly by blocking endothelial cell migration. Such factors include fragments of angiogenic proteins that are inhibitory (such as the amino-terminal fragment of urokinase), angiogenesis inhibitory factors, such as angiostatin and endostatin; soluble receptors of angiogenic factors, such as the urokinase type receptor or FGF/VEGF receptor; molecules which block endothelial cell growth factor receptors [O'Reilly et. al. *Cell* 88:277–285 (1997); O'Reilly, *Nat. Med.* 2:689–692 (1996)], and Tie-1 or Tie-2 inhibitors. Generally, an anti-angiogenic factor for use in the invention is a protein or polypeptide, which may be encoded by a gene transfected into tumors using the vectors of the invention. For example, the vectors of the invention can be used to deliver a gene encoding an anti-angiogenic protein into a tumor, its metastases or the tumor vasculature in accordance with the invention. Examples of anti-angiogenic factors include, but are not limited to, the amino terminal fragment (ATF) of urokinase, containing the EGF-like domain (e.g., amino acid residues about 1 to about 135 of ATF); ATF provided as a fusion protein, e.g., with immunoglobulin or human serum albumin [WO93/15199]; angiostatin [O'Reilly et al., *Cell* 79:315–328 (1994)]; tissue inhibitors of metalloproteinases [Johnson et al., *J. Cell. Physiol.* 160:194–202 (1994)]; or inhibitors of FGF or VEGF such as soluble forms of receptors for angiogenic factors, including but not limited to soluble VGF/VEGF receptors, and soluble urokinase receptors [Wilhem et al., *FEBS Letters* 337:131–134 (1994)].

In another preferred embodiment, a vector of the invention can be used to target migrating smooth muscle cells to inhibit post-angioplastic restenosis. An example of the use of an adenovirus to inhibit restenosis by delivery of a suicide gene is disclosed in WO96/05321. Use of an adenovirus encoding a GAX protein (growth arrest protein) to inhibit vascular smooth muscle cell proliferation and restenosis is disclosed in WO96/30385. Other genes can be cytotoxic genes (HSV thymidine kinase), metalloproteinases inhibitors (TIMP), endothelial NOS or atherosclerose protecting factors (e.g. ApoE).

A vector of the invention in which a muscle or a brain specific peptide has been included can also be used to selectively deliver protecting or regenerating growth factors for central nervous system (CNS) disorders. Examples of the use of adenoviruses to deliver genes to the CNS are disclosed in WO94/08026, WO95/25804 and WO95/26408.

A vector of the invention in which a skeletal muscle- or cardiac-specific peptide has been included can also be used to selectively deliver angiogenic factors (e.g; members of the VEGF, FGF, angiopoietin famillies), cell survival-promoting factors (e.g. members of the akt/PKB family), genes involved in the energetic metabolism (e.g. phospholamban or adenylyl cyclase), cytokins and their receptors (e.g. IL-6, IL 10, CXCR4, CXCR1, sdf1, MCP 1, GM-CSF and genes protecting against apoptose (akt) useful for the treatment of peripheral artery diseases or coronary artery diseases.

In a more general way the vectors of the present invention to deliver to targeting cells genes enzymes, blood derivatives, hormones such as insulin or growth hormone, lymphokines: interleukins, interferons, TNF, and the like (French Patent No. 92 03120), growth factors, for example angiogenic factors such as VEGF or FGF, neurotransmitters or precursors thereof or synthesis enzymes, trophic, in particular neurotrophic, factors for the treatment of neurodegenerative diseases, of traumas which have damaged the nervous system, or of retinal degeneration: BDNF, CNTF, NGF, IGF, GMF, IFGF, NT3, NT5, HARP/pleiotrophin, or bone growth factors, haematopoietic factors, and the like, dystrophin or a minidystrophin (French Patent No. 91 11947), genes encoding factors involved in coagulation: for example, factors VII, VIII and IX, suicide genes (e.g. thymidine kinase and cytosine deaminase), genes for haemoglobin or other protein carriers, genes corresponding to the proteins involved in the metabolism of lipids, of the apolipoprotein type chosen from apolipoproteins A-I, A-II, A-IV, B, C-I, C-II, C-III, D, E, F, G, H, J and apo(a), metabolic enzymes such as, for example, lipoprotein lipase, hepatic lipase, lecithin-cholesterol acyltransferase, 7-alpha-cholesterol hydroxylase, phosphatidyl acid phosphatase, or lipid transfer proteins such as the cholesterol ester transfer protein and the phospholipid transfer protein, an HDL-binding protein or a receptor chosen, for example, from the LDL receptors, the remnant chylomicron receptors and the scavenger receptors, and the like. It is possible to add, in addition, leptin for the treatment of obesity.

Among the other proteins or peptides which may be encoded by the gene of the targeted vector, it is important to underline antibodies, the variable fragments of single-chain antibody (ScFv) or any other antibody fragment possessing recognition capacities for its use in immunotherapy, for example for the treatment of infectious diseases, of tumours, of autoimmune diseases such as multiple sclerosis (which may involve the use of antiidiotype antibodies). Other proteins of interest are, in a nonlimiting manner, soluble receptors such as, for example, the soluble CD4 receptor or the soluble receptor for TNF which may be used for example for anti-HIV therapy, the soluble receptor for acetylcholine which may be used for example for the treatment of myasthenia; substrate peptides or enzyme inhibitors, or peptides which are agonists or antagonists of receptors or of adhesion proteins such as, for example, for the treatment of asthma, thrombosis and restenosis; artificial, chimeric or truncated proteins. Among the hormones of interest, there may be mentioned insulin in the case of diabetes, growth hormone and calcitonin.

The said gene may also be replaced by an antisense sequence or gene whose expression in the target cell makes it possible to control the expression of genes or the transcription of cellular mRNAs. Such sequences may, for example, be transcribed in the target cell into RNA complementary to cellular mRNAs and thus block their translation into protein, according to the technique described in European Patent No. 140 308. The therapeutic genes may also comprise the sequences encoding ribozymes, which are capable of selectively destroying target RNAs (European Patent No. 321201).

EXAMPLES

The present invention may be better understood by reference to the following non-limiting Examples, which are provided as exemplary of the invention. All the modifications presented in the examples can be combined when not cited.

Example 1

Manipulation of the Hexon HVR5 Loop of Ad5

The present example demonstrates that manipulation of the HVR5 loop of Ad5 hexon from amino acids (aa) 269 to 281, keeping intact the most conserved residues at the extremities of the loop (a serine in position 268, and a proline in position 282), unexpectedly provides for effective adenovirus tropism engineering. The sequence removed from the Ad5 hexon was: TTEAAAGNGDNLT (SEQ ID NO: 25) (i.e., our constructs naturally display a threonine to alanine substitution at hexon residue 273 as compared to the published refence sequence of Ad5), and the flanking sequences conserved were FFS (upstream) and PKVV (downstream).

Materials and Methods

Construction of shuttle plasmids for the manipulation of the HVR5 loop of the hexon. A first intermediate plasmid IE28 containing the flanking regions of the HVR5 loop and in which the HVR5 loop was replaced with the xylE marker gene from *Pseudomones putida* (Zukowski et al., 1983, PNAS 80:1101–1105) was made using the following two primer pairs:
hex-19243G (5'-ATGGGATGAAGCTGCTACTG-3') (SEQ ID NO:26) and
hex-19623D (5'-tcgcgaGAAAAATTGCATTTCCACTT-3') (SEQ ID NO:27), and
hex-19685G (5'-CCTAAGGTGGTATTGTACAG-3') (SEQ ID NO:28) and
hex-20065D (5'-AGCAGTAATTTGGAAGTTCA-3') (SEQ ID NO:29).
These primers were used to amplify portions of the hexon gene corresponding respectively to nucleotides 19245 to 19639 and 19685 to 20084 of the Ad5 genome (Genbank access number M73260) according to standard PCR techniques. Primer hex-19623D contains the restriction site NruI and the primer hex-19685G was slightly modified with respect to Ad5 sequence to create a Bsu36I site without modifying the protein sequence of the hexon (nucleotide 19690: A to G). Each PCR product was cloned in the plasmid pCRII (Invitrogen) to generate the plasmids IE21 and IE22, respectively. Proper cloning was confirmed by DNA sequencing.

The plasmid pαxylEΩ (Frey et al., 1988, Gene 62:237–247) containing the expression cassette of the xylE gene was restricted with EcoRI, blunt-ended with the T4 DNA polymerase, and digested with HindIII. This DNA fragment was cloned into the blunt-ended BamHI-HindIII IE21 plasmid, resulting in plasmid IE26. Finally, the HindIII-XbaI fragment from IE26 and the XhoI-HindIII fragment from IE22 were cloned into the SalI-XbaI cleaved plasmid pXL2756 previously described (Crouzet et al., 1997, PNAS 94: 1414–1419) to generate the shuttle plasmid IE28.

All the plasmids modified in the HVR5 loop were derived from plasmid IE28 by replacement of the xylE gene with double-stranded oligonucleotides. Briefly, complementary single-stranded oligonucleotides were annealed to form duplexes and cloned into the NruI-Bsu36I digested IE28, except for the IE31 plasmid, which was obtained by ligation of the double-stranded oligonucleotide with the BsrGI-NruI cleaved IE28. Phenotypic screening based on the yellow staining of bacteria expressing xylE after spraying with 0.5 M catechol was used (Zukowski et al., 1983 supra.). The following table indicates the list of the oligonucleotides used and the names of the corresponding shuttle plasmids:

TABLE 1

Oligonucleotides used to produce specific hexon insert plasmid constructs.

| shuttle plasmid | oligonucleotides | SEQ ID NO: |
|---|---|---|
| IE30 (Ad2 HVR5) | 5'-AATACTACCTCTTTGAACGACCGGCAAGGCAATGCTACTAAACC-3' | 30 |
|  | 5'-TTAGGTTTAGTAGCATTGCCTTGCCGGTCGTTCAAAGAGGTAGTATT-3' | 31 |
| IE31 (epitope from poliovirus type 3)* | 5'-AATCTAGACTCTTTGGAACAACCTACTACTCGCGCTCAAAAACCACGTCTAGATTT-3' | 32 |
|  | 5'-GTACAAATCTAGACGTGGTTTTTGAGCGCGAGTAGTAGGTTGTTCCAAAGAGTCTAGATT-3' | 33 |
| IE32 (Ad 30 HVR5) | 5'-TCAACCACTATAAACATTCC-3' | 34 |
|  | 5'-TTAGGAATGTTTATAGTGGTTGA-3' | 35 |
| IE33 (Ad 19 HVR5) | 5'-ACTCCTGGCGCAAATCCTCCAGCAGGCGGTAGTGGAAACGAAGAATACAAACC-3' | 36 |
|  | 5'-TTAGGTTTGTATTCTTCGTTTCCACTACCGCCTGCTGGAGGATTTGCGCCAGGAGT-3' | 37 |
| IE35 (epitope from poliovirus type 1 (5)) | 5'-GATAACCCAGCGTCGACCACGAATAAGGATAAGCTACC-3' | 38 |
|  | 5'-TTAGGTAGCTTATCCTTATTCGTGGTCGACGCTGGGTTATC-3' | 39 |
| IE37 (epitope from poliovirus type 1) | 5'-GGAGATAACCCAGCGTCGACCACGAATAAGGATAAGCC-3' | 40 |
|  | 5'-TTAGGCTTATCCTTATTCGTGGTCGACGCTGGGTTATCTCC-3' | 41 |
| IE40 (epitope from poliovirus type 1) | 5'-TCTGATAACCCAGCGTCGACCACGAATAAGGATAAGCC-3' | 42 |
|  | 5'-TTAGGCTTATCCTTATTCGTGGTCGACGCTGGGTTATCAGA-3' | 43 |
| IE41 (epitope from poliovirus type 1) | 5'-GGATCTGATAACCCAGCGTCGACCACGAATAAGGATAAGCC-3' | 44 |
|  | 5'-TTAGGCTTATCCTTATTCGTGGTCGACGCTGGGTTATCAGATCC-3' | 45 |
| IE43(epitope from polioviris type 1) | 5'-GGAGATAACCCAGCGTCGACCACGAATAAGGATAAGCTAGGTGGCCC-3' | 46 |
|  | 5'-TTAGGGCCACCTAGCTTATCCTTATTCGTGGTCGACGCTGGGTTATCTCC-3' | 47 |
| IE44 (epitope from poliovirus type 1) | 5'-GGAGATAACCCAGCGTCGACCACGAATAAGGATAAGCTAGGTTCTCC-3' | 48 |
|  | 5'-TTAGGAGAACCTAGCTTTATCCTTATTCGTGGTCGACGCTGGGTTATCTCC-3' | 49 |
| IE45 (epitope from poliovirus type 1) | 5'-GGAGATAACCCAGCGTCGACCACGAATAAGGATAAGCTATCTCC-3' | 50 |
|  | 5'-TTAGGAGATAGCTTATCCTTATTCGTGGTCGACGCTGGGTTATCTCC-3' | 51 |
| IE46 (epitope from poliovirus type 1) | 5'-GGAGATAACCCAGCGTCGACCACGAATAAGGATAAGCTATCTGGTCC-3' | 52 |
|  | 5'-TTAGGACCAGATAGCTTATCCTTATTCGTGGTCGACGCTGGGTTATCTCC-3' | 53 |
| IE47 (epitope from poliovirus type 1) | 5'-GGAGATAACCCAGCGTCGACCACGAATAAGGATAAGCTATCTAGTCC-3' | 54 |
|  | 5'-TTAGGACTAGATAGCTTATCCTTATTCGTGGTCGACGCTGGGTTATCTCC-3' | 55 |

*Crompton, et al., 1994, J. Gen. Vir. 75:133–139.

Construction of the associated plasmid backbones and viruses. An intermediate plasmid backbone containing the xylE gene instead of the HVR5 loop of the hexon gene was constructed to facilitate subsequent manipulation of the HVR5 loop. For this purpose, the shuttle plasmid IE28 was recombined with the plasmid backbone pXL3006 (this plasmid contains a PacI-excisable E1E3-deleted adenoviral genome with a CMV-lacZ expression cassette in place of the E1 region) in the G4977 bacterial strain according to the method described by Crouzet et al. (1997 supra.) to obtain the plasmid backbone IE28c, which differs from plasmid backbone pXL3006 by the xylE-containing HVR5 sequence.

All the shuttle plasmids IE30 to IE47 were then recombined with the plasmid backbone IE28c using the "xylE screening" to get the plasmid backbones IE30c to IE47c. After cleavage with the PacI enzyme, 2 μg (or 5 μg) of these digested backbones were transfected in the 911 cells (or 293 cells) using Lipofectamine (Gibco BRL) to generate the corresponding viruses AdIE30 to AdIE47. These HVR5-modified E1E3-deleted adenoviruses therefore express the same CMV-lacZ expression cassette.

All other HVR5-modified adenoviruses (e.g., displaying uPAR- or integrin-binding peptides; see examples thereafter) were constructed by the same strategy.

Cells and antibodies. 293 and W162 cells were maintained in MEM (Gibco BRL) supplemented with 10% fetal calf serum. 911 cells (Fallaux et al., 1996, Hum. Gene Ther. 7:215) were grown in DMEM supplemented with 10% fetal calf serum. The C3 monoclonal antibody (C3 mAb) directed against the poliovirus type 1 described in Blondel et al, 1983, Virology 126:707 was provided by Dr. R. Crainic (Pasteur Institute, Paris, France). L5 rabbit polyclonal antibodies directed against the whole Ad5 capsid were produced in RPR-Gencell's facilities (RPR SA, Vitry, France).

Viruses. All the viruses were amplified in E1-transcomplementing cells (e.g., 293 cells) according to classical methods. The pattern/identity of the viruses was controlled by restriction analysis and sequencing of the inserts on viral DNA obtained using the Hirt procedure. Viral stocks were prepared in 293 cells, purified by CsCl gradient, desalted using PD10 columns (Pharmacia) and stored in PBS supplemented with 10% glycerol at −80° C. Biological quantification was carried out by numbering the plaque-forming units (PFU) on 911 cells and/or numbering the lacZ-transducing units (TDU) two days post-infection of W162 cells following X-Gal staining (Dedieu et al. 1997, J. Virol. 71 :4626). Physical quantification was carried out by anion-exchange by numbering the viral particles (VP).

Neutralization test. One-half μl of anti poliovirus C3 monoclonal antibody were incubated in PBS for 1 h at 37° C. with $10^5$ TDU of purified virus, and the mix was then absorbed onto W162 cells in a 6 wells-plate for a further 1 h at 37° C. Cells were then washed twice with PBS, and fresh medium was added to the cells which were incubated at 37° C. for 2 days. Cell monolayers were fixed with formaldehyde (0.37%)-glutaraldehyde (0.2%), X-Gal stained, and blue cells were counted.

Immunoprecipitation protocol. Viral particles ($10^{10}$) of CsCl-purified virus were resuspended in 400 μl of non-denaturing incubation buffer (50 mM Tris pH7.5, 150 mM NaCl, 0.05% NP40) and then incubated with 0.1 μl of anti poliovirus C3 monoclonal antibody for 1 h at 4° C. Four hundred μl of protein A-Sepharose previously equilibrated with incubation buffer was then added, and further incubated for 1 h at 4° C. Following incubation, the mix was spun down by brief centrifugation in a microcentrifuge. The pellet was washed twice with 1 ml of incubation buffer and once with 1 ml of 10 mM Tris pH7.5, 0.1% NP40 for 20 min at 4° C. The pellet containing the protein A-antibody-virus complex was resuspended in 50 μl of Laemmli buffer 1×, boiled 2 min and the supernatant was collected after a brief centrifugation. Ten μl of supernatant was analyzed by SDS-polyacrylamide gel electrophoresis (Novex). Western blot was carried out using the L5 rabbit polyclonal serum directed against the whole Ad5 capsid according to the ECL procedure (Amersham).

Results

Construction strategy for modification of the HVR5 loop. Two series of constructions were made. The first one was designed to assess the "capacity" of the Ad5 HVR5 loop for foreign sequences, by replacement of this loop by the HVR5 loops from other Ad serotypes, which greatly differ in size.

TABLE 2

Ad5-based adenoviruses with heterospecific HVR5 loops.

| Virus | HVR5 sequence of | sequence replacing the HVR5 loop of Ad5 | SEQ ID NO: |
|---|---|---|---|
| Ad IE 30 | Ad2:14 aa | NTTSLNDRQGNATK | 56 |
| Ad IE 32 | Ad30:6 aa | STTINI | 57 |
| Ad IE 33 | Ad 19:17 aa | TPGANPPAGGSGNEEYK | 58 |

As a viability control, we introduced the modification published by Crompton et al. (1994, J. Gen. Virol. 75:133–139) in which a poliovirus type 3 epitope was introduced in place of a larger deletion encompassing HVR5. Importantly, the crompton virus was initially constructed by homologous recombination between a plasmid containing the Ad2 modified hexon and an Ad5-based adenoviral genome. This virus therefore displays a chimeric hexon protein between Ad2 and Ad5 in which a 4-residue larger HVR5 deletion has been substituted for a foreign peptide. To reproduce the Crompton et al. construct as closely as possible, an Ad5-based virus (Ad IE31) was constructed by the EDRAG technology in which the foreign peptide of Crompton et al. was introduced in place of hexon residues 269 to 285 (TTEAAAGNGDNLTPKVV; SEQ ID NO:59) of Ad5 instead of TTEAAAGNGDNLT (SEQ ID NO:60).

TABLE 3

Insert of control virus AdIE31.

| Virus | sequence replacing the HVR5 loop of Ad5 |
|---|---|
| Ad IE31 | NLDSLEQPTTRAQKPRLD (SEQ ID NO: 61) |

In the second series of constructs, the HVR5 loop (aa 269 to 281) was replaced by a neutralizing linear epitope of poliovirus type 1 (DNPASTTNKDK; SEQ ID NO:62). This model binding-peptide was inserted in various neighboring contexts (i.e., various linkers composed of leucine and/or glycine and/or serine residues were used) to assess their importance for virus viability and peptide accessibility.

TABLE 4

Insertions of a poliovirus type 1 epitope in the HVR5 loop.

| Virus | upstream linker | epitope used | downstream linker | SEQ ID NO: |
|---|---|---|---|---|
| Ad IE35 | none | DNPASTTNKDK | L | 63 |
| Ad IE37 | G | DNPASTTNKDK | none | 64 |
| Ad IE40 | S | DNPASTTNKDK | none | 65 |

TABLE 4-continued

Insertions of a poliovirus type 1 epitope in the HVR5 loop.

| Virus | upstream linker | epitope used | downstream linker | SEQ ID NO: |
|---|---|---|---|---|
| Ad IE41 | G S | DNPASTTNKDK | none | 66 |
| Ad IE43 | G | DNPASTTNKDK | LG G | 67 |
| Ad IE44 | G | DNPASTTNKDK | LG S | 68 |
| Ad IE45 | G | DNPASTTNKDK | LS | 69 |
| Ad IE46 | G | DNPASTTNKDK | LSG | 70 |
| Ad IE47 | G | DNPASTTNKDK | LS S | 71 |

Viability of the viruses. The three viruses with Ad2, Ad19, or Ad30 HVR5 loops instead of the Ad5 HVR5 loop, and the nine chimeric virus containing the poliovirus type 1 epitope were viable. No loss of productivity was observed. Unexpectedly, the control virus Ad IE31 could not be recovered despite intensive efforts.

Assessment of poliovirus epitope accessibility by immunoprecipitation assay. Immunoprecipitation experiments were performed on the viruses carrying the poliovirus epitope using a cognate antipoliovirus monoclonal antibody (C3 mAb) in non-denaturing conditions. The following table 5 summarizes the data obtained:

TABLE 5

Immunoprecipitation with C3 mAb.

| Virus | peptide inserted in the HVR5 loop | SEQ ID NO: | Immunoprecipitation |
|---|---|---|---|
| Ad IE35 | DNPASTTNKDK-L | 63 | – |
| Ad IE37 | G-DNPASTTNKDK | 64 | – |
| Ad IE40 | S-DNPASTTNKDK | 65 | – |
| Ad IE41 | GS-DNPASTTNKDK | 66 | – |
| Ad IE43 | G-DNPASTTNKDK-LGG | 67 | ++ |
| Ad IE44 | G-DNPASTTNKDK-LGS | 68 | ++ |
| Ad IE45 | G-DNPASTTNKDK-LS | 69 | ++ |
| Ad IE46 | G-DNPASTTNKDK-LSG | 70 | ++ |
| Ad IE47 | G-DNPASTTNKDK-LSS | 71 | ++ |

The presence of a linker downstream of the poliovirus epitope was thus found critical for C3 mAb binding to the modified viral capsids, most likely because it allows proper presentation and/or accessibility of the binding peptide at the hexon surface. When the modified viruses were denatured prior to immunoprecipitation, all of them were efficiently immunoprecipitated by C3 mAb (not shown).

Assessment of poliovirus epitope functionality by neutralization assay. As the C3mAb is neutralizing for poliovirus infection, we anticipated that it could also neutralize the infectivity of Ad carrying the poliovirus epitope. Incubation of C3mAb with the whole series of Ad IE viruses was performed in PBS (i.e., under native conditions) prior to infection of W162 monkey cells. The data are shown in FIG. 1. These data correlate perfectly with the immunoprecipitation results, i.e., all the viruses that could bind C3 mAb in non-denaturing conditions were also neutralized by this antibody.

Discussion

The data show that modification of the HVR5 loop of adenovirus can allow functional and specific interaction of the modified hexons with a specific binding protein. Particular modes of insertion are however required as the data showed that accessibility (immunoprecipitation assay) and functionality (neutralization assay) of the binding peptide epitope were dependent on minimal spacer/neighboring sequences.

Contrasting with the conclusion of Crompton et al., our results also show that the deletion of aa 269 to 285 of Ad5 hexon is deleterious for virus growth and/or viability. This can be explained by the fact that the residues 282 to 285 are localized in the bêta-strand located downstream of the HVR5 loop, which is probably essential for the structure of the hexon as a monomer or a trimer. Therefore, the present approach, which is more precise and rigorous than that described in Crompton et al., unexpectedly overcame the disadvantages of that reference and provided viable viruses equipped with a modified tropism (see below).

Example 2

Manipulation of the Fiber HI Loop

Deletion of the HI loop of the Ad5 fiber was performed: the sequence removed from the fiber knob includes residues 538 to 548 (i.e., sequence GTQETGDTTPS) (SEQ ID NO:72). Its flanking sequences are thus TLN (upstream) and AYS (downstream).

Materials and Methods

Construction of shuttle plasmids for the manipulation of the HI loop of the fiber. A first intermediate plasmid pJD3 containing the flanking regions of the HI loop and in which the HI loop was replaced with the xylE gene was made using the following two primer pairs:

HIgu1 (5'-CAGCTCCATCTCCTAACTGTAGACTAAATG-3') (SEQ ID NO:73) and HIgd1 (5'-GGTTACCGGTTTAGTTTTGTCTCCGTTTAA-3') (SEQ ID NO:74), and HIdu1 (5'-AGCGCTTACTCTATGTCATTTTCATGGGAC-3') (SEQ ID NO:75) and HIdd1 (5'-GAGTTTATTAATATCACTGATGAGCGTTTG-3') (SEQ ID NO:76).

These primer pairs were used to amplify portions of the fiber and E4orf7 genes corresponding respectively to nucleotides 32255 to 32634 and 32712 to 33090 of the Ad5 genome (Genbank access number M73260) according to standard PCR techniques. The primers HIgd1 and HIdu1 are designed in such a way that they create the restriction sites BstEII and Eco47III, respectively, without modifying the fiber protein sequence at the immediate vicinity of the HI loop. These sites were further used for direct cloning of foreign peptides into HI (see below and table 5).

Each PCR product was cloned into the plasmid PCR2.1 (Invitrogen) to generate the plasmids PCR2.1-H4 and PCR2.1-I2, respectively, and sequenced.

The plasmid pαxylEΩ containing the expression cassette for the xylE gene was restricted with EcoRI, blunt-ended with the T4 DNA polymerase, and digested with HindIII. This DNA fragment was subcloned into HindIII-restricted PCRII (Invitrogen) resulting in the plasmid IE23. A NsiI-XhoI fragment of IE23 was introduced into the NsiI-XhoI digested PCR2.1-H4 plasmid, resulting in the plasmid pJD2. Finally, the SacI-XbaI fragment from pJD2 and the SpeI-XhoI fragment from PCR2.1-I2 were cloned into the previously described (Crouzet et al., 1997, supra.) plasmid pXL2756 cleaved by SacI-SalI to generate the shuttle plasmid pJD3.

All the plasmids modified in the HI loop were derived from plasmid pJD3 by replacement of the xylE gene with double-stranded oligonucleotides. Briefly, complementary single-stranded oligonucleotides were annealed to form duplexes and cloned into BstEII-Eco47III digested pJD3. A phenotypic screening based on the yellow staining of bacteria expressing xylE after spraying with 0.5M catechol was used. The following table indicates the list of the oligonucleotides used and the name of the corresponding shuttle plasmids:

Shuttle plasmids pJD5, 7 and 6, and pCF1 to pCF8 were then recombined with the plasmid backbone pBX using the "xylE screening" to get the plasmid backbones pBV2, 5 and 9, and pBC1 to pBC8, respectively. After cleavage with the PacI enzyme, 2 µg (or 5 µg) of DNA were transfected in the 911 cells (or 293 cells) using Lipofectamine (Gibco BRL) to

TABLE 5

Examples of oligonucleotides used to replace the HI loop.

| Shuttle plasmid | oligonucleotides | SEQ ID NO: |
|---|---|---|
| pJD7 (HI loop from Ad5) | 5'-GTAACACTAACCATTACACTAAACGGTACCCAGGAAACAGGAGACACAACTCCAAGT-3'<br>5'-ACTTGGAGTTGTGTCTCCTGTTTCCTGGGTACCGTTTAGTGTAATGGTTAGT-3' | 77<br>78 |
| pJD5 (HI loop from Ad2) | 5'-GTAACACTAACCATTACACTAAACGGTACCAGTGAATCCACAGAAACTAGCGAGGTAAGC-3'<br>5'-GCTTACCTCGCTAGTTTCTGTGGATTCACTGGTACCGTTTAGTGTAATGGTTAGT-3' | 79<br>80 |
| pJD6 (HI loop from Ad9) | 5'-GTAACACTAACCATTACACTAAACCAAGAAACACAATGTGAA-3'<br>5'-TTCACATTGTGTTTCTTGGTTTAGTGTAATGGTTAGT-3' | 81<br>82 |
| pCF1 (epitope from poliovirus type 1) | 5'-GTAACCCTAACCATTACACTAAACGGTGATAACCCAGCGTCGACCACGAATAAGGATAAGAGC-3'<br>5'-GCTCTTATCCTTATTCGTGGTCGACGCTGGGTTATCACCGTTTAGTGTAATGGTTAGG-3' | 83<br>84 |
| pCF2 (epitope from poliovirus type 1) | 5'-GTAACCCTAACCATTACACTAAACGGTGATAACCCAGCGTCGACCACGAATAAGGATAAGGGAAGC-3'<br>5'-GCTTCCCTTATCCTTATTCGTGGTCGACGCTGGGTTATCACCGTTTAGTGTAATGGTTAGG-3' | 85<br>86 |
| pCF3 (epitope from poliovirus type 1) | 5'-GTAACCCTAACCATTACACTAAACGGTGATAACCCAGCGTCGACCACGAATAAGGATAAGTCAAGC-3'<br>5'-GCTTGACTTATCCTTATTCGTGGTCGACGCTGGGTTATCACCGTTTAGTGTAATGGTTAGG-3' | 87<br>88 |
| pCF4 (epitope from poliovirus type 1) | 5'-GTAACCCTAACCATTACACTAAACGGTGATAACCCAGCGTCGACCACGAATAAGGATAAGGGCGGAAGC-3'<br>5'-GCTTCCGCCCTTATCCTTATTCGTGGTCGACGCTGGGTTATCACCGTTTAGTGTAATGGTTAGG-3' | 89<br>90 |
| pCF5 (epitope from poliovirus type 1) | 5'-GTAACCCTAACCATTACACTAAACGGTGATAACCCAGCGTCGACCACGAATAAGGATAAGTCATCTAGC-3'<br>5'-GCTAGATGACTTATCCTTATTCGTGGTCGACGCTGGGTTATCACCGTTTAGTGTAATGGTTAGG-3' | 91<br>92 |
| pCF6 (epitope from poliovirus type 1) | 5'-GTAACCCTAACCATTACACTAAACGGTGATAACCCAGCGTCGACCACGAATAAGGATAAGGGATCCAGC-3'<br>5'-GCTGGATCCCTTATCCTTATTCGTGGTCGACGCTGGGTTATCACCGTTTAGTGTAATGGTTAGG-3' | 93<br>94 |
| pCF7 (epitope from poliovirus type 1) | 5'-GTAACCCTAACCATTACACTAAACGGTGATAACCCAGCGTCGACCACGAATAAGGATAAGTCAGGAAGC-3'<br>5'-GCTTCCTGACTTATCCTTATTCGTGGTCGACGCTGGGTTATCACCGTTTAGTGTAATGGTTAGG-3' | 95<br>96 |
| pCF8 (epitope from poliovirus type 1) | 5'-GTAACCCTAACCATTACACTAAACGGTGATAACCCAGCGTCGACCACGAATAAGGATAAG-3'<br>5'-CTTATCCTTATTCGTGGTCGACGCTGGGTTATCACCGTTTAGTGTAATGGTTAGG-3' | 97<br>98 |

Construction of the associated plasmid backbones and viruses. An intermediate plasmid backbone containing the xylE gene instead of the HI loop of the fiber gene was first constructed to facilitate subsequent screening of any plasmid backbone displaying a modified HI loop. For this purpose, the shuttle plasmid pJD3 was recombined with the plasmid backbone pXL3006 in the G4977 bacterial strain according to the method described by Crouzet et al, supra, to obtain the plasmid backbone pBX, which therefore displays a PacI-excisable E1E3-deleted adenoviral genome containing a CMV-lacZ expression cassette in place of E1, as well as the xylE marker in the HI loop.

generate the corresponding viruses vBV2, 5 and 9, and vBC1 to vBC8.

Other methods. The cells, antibodies, viruses, immunoprecipitation assays, and neutralization assays were as described in Example 1, supra.

Results

Construction strategy for the HI loop insertion vectors. Two series of constructions were made. The first one was designed to assess the "capacity" of the Ad5 HI loop for foreign sequences, by replacement of this loop by the HI loops of other adenovirus serotypes, with some variations in size.

TABLE 6

Capacity insertions in the fiber protein HI loop.

| Virus | HI sequence of | sequence replacing the HI loop of Ad5 | SEQ ID NO: |
|---|---|---|---|
| VBV2 | Ad2:12 aa | GTSESTETSEVS | 99 |
| VBV5 | Ad5:11 aa | GTQETGDTTPS | 100 |
| VBV9 | Ad9:6 aa | QETQCE | 101 |

In the second series of constructs, the HI loop was replaced by a neutralizing epitope of poliovirus type 1 (DNPASTTNKDK) (SEQ ID NO:62). Due to the very close 3D structures at the N-terminal sides of the Ad5 HI loop and the poliovirus sequences in their native environment/protein, a minimal one residue linker (glycine) was added usptream of the epitope. This was not the case downstream of the insertion site for which spacers of different length and composition were included to assess their impact on virus growth and peptide accessibility.

TABLE 7

Insertions of a poliovirus type 1 epitope in the fiber protein HI loop.

| Virus | epitope used | downstream linker | SEQ ID NO: |
|---|---|---|---|
| vBC1 | DNPASTTNKDK | S | 102 |
| vBC2 | DNPASTTNKDK | G S | 103 |
| vBC3 | DNPASTTNKDK | S S | 104 |
| vBC4 | DNPASTTNKDK | G G S | 105 |
| vBC5 | DNPASTTNKDK | S S S | 106 |
| vBC6 | DNPASTTNKDK | G S S | 107 |
| vBC7 | DNPASTTNKDK | S G S | 108 |
| vBC8 | DNPASTTNKDK | none | 109 |

Viability of the viruses. The three control viruses with Ad2, Ad5 or Ad9 HI loops instead of the Ad5 HI loop and the 8 chimaeric virus containing the poliovirus epitope were viable. No loss of productivity was observed.

Assessment of poliovirus epitope accessibility by immunoprecipitation assay. Immunoprecipitation experiments of the viruses carrying the poliovirus epitope were performed with the cognate antipoliovirus C3mAb in non-denaturing conditions. The following table summarizes the data:

TABLE 8

Recognition of the targeting sequence as detected by immunoprecipitation with C3 mAb.

| Virus | Peptide inserted in the HI loop | SEQ ID NO: | Immuno-precipitation |
|---|---|---|---|
| VBC1 | G-DNPASTTNKDK-S | 151 | – |
| VBC2 | G-DNPASTTNKDK-GS | 152 | +/– |
| VBC3 | G-DNPASTTNKDK-SS | 153 | + |
| VBC4 | G-DNPASTTNKDK-GGS | 154 | ++ |
| VBC5 | G-DNPASTTNKDK-SSS | 155 | ++ |
| VBC6 | G-DNPASTTNKDK-GSS | 156 | ++ |
| VBC7 | G-DNPASTTNKDK-SGS | 157 | ++ |
| VBC8 | G-DNPASTTNKDK | 64 | – |

These data show that, as for HVR5 loop insertion, binding of the C3 mAb antibody to the modified capsids was criticaly dependent on the presence of a spacer sequences of minimal length. In particular, a downstream linker of 3 residues conferred the most efficient binding. When the viruses were denatured prior to the immunoprecipitation assay, they were all able to bind the C3 mAb antibody (not shown).

Assessment of poliovirus epitope functionality by neutralisation assay. The ability of C3mAb to neutralize infectivity of the fiber-modified viruses was then assessed to determine if it also correlated with the immunoprecipitation data as exemplified in Example 1 for the hexon-modified capsids. However, unlike the results with hexon modification, there was no inhibition of infectivity following incubation of any of the fiber-modified virus with C3mAb (data not shown). Different explanations can be suggested. In particular, there are only 12 fiber trimers on the virion surface versus 240 hexon trimers. Therefore, the density of antibody binding to the hexon-modified capsids may have decreased virus infectivity either directly, or following steric hindrance of the RGD motif of the penton base so integrin-mediated internalisation was affected. In any case, C3mAb specific binding to the HI-modified capsids did not prevent native interaction between the virus and its target cells.

Discussion

The data demonstrate that the HI loop of adenovirus can be replaced by a foreign peptide and that the corresponding viruses are: i) viable, and ii) with no drastic effect on virus productivity. The data also demonstrate that specific recognition of the introduced peptide requires suitable neighboring linkers (i.e., flexible linkers of minimal size).

Example 3

Modification of Fiber Protein Length—Short Fibers

Taking into account the comparison of the cell-binding pathway of Ad5 (a long-fiber serotype) with other serotypes such as Ad9 (a short-fiber serotype), the length of the shaft of the fiber was modified by designing either an intertypic fiber (substitution of the Ad5 shaft by the Ad3, another short-fiber serotype, shaft), or a shortened Ad5 shaft that retained only 6 or 9 repeats instead of 22 in the native protein.

Materials and Methods

Construction of shuttleplasmids with shortened fibers. Three shuttle plasmids containing shortened fibers were constructed. Two of them (pSF1 and pSF2) display major deletions within the fiber shaft, whereas the third one (pIF1) harbors the Ad3 shaft instead of that of Ad5. All constructs therefore retain the Ad5 tail and knob domains.

To construct pSF1, two pairs of primers were used:

5M3g (5'-ATTTCTGTCGACTTTATTCAGCAGCACCTC-3') (SEQ ID NO:110) and

5M3d (5'-GTTTGACTTGGTTTTTTGAGAGGTGGGCT-3') (SEQ ID NO:111), and

5M17g (5'-TTGGATATTAACTACAACAAAGGCCTTTAC-3') (SEQ ID NO:112) and

5M17d (5'-GAAACTGGAGCTCGTATTTGACTGCCACAT-3') (SEQ ID NO:113).

These primers were used to amplify portions of the fiber gene corresponding respectively to nucleotides 30885 to 31329 and 31936 to 32351 of the Ad5 genome (Genbank access number M73260) according to standard PCR techniques. The primers 5M3g and 5M17d slightly differ from the Ad5 sequence by respectively containing the restriction sites SalI and SacI. After digestion by SalI or SacI, these PCR products were ligated and cloned into the SacI-SalI cleaved pXL2756, resulting in the pSF1 plasmid which displays an in frame deletion encompassing shaft repeats 4 to 16.

To construct pSF2, two pairs of primers were used:
5M3g (5'-ATTTCTGTCGACTTTATTCAGCAGCACCTC-3') (SEQ ID NO: 114) and
5M3d (5'-GTTTGACTTGGTTTTTTTGAGAGGTGGGCT-3') (SEQ ID NO:115), and
5M20g (5'-CTCAAAACAAAAATTGGCCATGGCCTAGAA-3') (SEQ ID NO:116) and
5M20d (5'-ATCCAAGAGCTCTTGTATAGGCTGTGCCTT-3') (SEQ ID NO:117).

These primers were used to amplify portions of the fiber gene corresponding respectively to nucleotides 30885 to 31329 and 32110 to 32530 of the Ad5 genome according to standard PCR techniques. The primers 5M3g and 5M20d slightly differ from the Ad5 sequence by respectively containing the restriction sites SalI and SacI. After digestion by SalI or SacI, these PCR products were ligated and cloned into the SacI-SalI cleaved pXL2756, resulting in the pSF2 plasmid which displays an in frame deletion encompassing shaft repeats 4 to 19.

The pIF1 plasmid was made using the gene SOEing method described by Horton et al (4) consisting of recombining DNA sequences by PCR without relying on restriction sites. Five successive steps were necessary to construct the pIF1 plasmid, which contains an intertypic fiber gene, composed of the Ad5 tail and knob and the Ad3 shaft. A first PCR product containing the Ad5 fiber tail was amplified from the Ad5 genome using the primers:
SOE35Tg (5'-TACAAGTCGACAACCAAGCGTCAGAAATTG-3') (SEQ ID NO:118) and
SOE35Td (5'-AAGACTTAAAACCCCAGGGGGACTCTCTTG-3') (SEQ ID NO:119).

The primer SOE35Tg nearly matches the Ad5 nucleotides 30660 to 30689 with a slight modification resulting in the creation of a SalI site. The 15 underlined bases in the SOE35Td primer match with the sequence of the first repeat of the Ad3 fiber shaft and the 15 remaining bases correspond to the sequence of the fiber tail end of Ad5.

A second PCR product containing the Ad3 fiber shaft was amplified from the Ad3 fiber gene using the primers:
SOE35Sg (5'-GAGAGTCCCCCTGGGGTTTTAAGTCTTAAA-3') (SEQ ID NO: 120) and
SOE35Sd (5'-GGTCCACAAAGTGTTATTTTTCAGTGCAAT-3') (SEQ ID NO:121).

The underlined bases in both primers are contained in the Ad5 fiber gene (respectively within the tail and knob subdomains), the remaining ones are from the Ad3 shaft.

A third PCR product containing part of the Ad5 fiber knob was amplified from the Ad5 fiber gene using the primers
SOE35Kg (5'-CTGAAAAATAACACTTTGTGGACCACACCA-3') (SEQ ID NO: 122) and
SOE35Kd (5-TCCTGAGCTCCGTTTAGTGTAATGGTTAGT-3') (SEQ ID NO:123).

Figure 2A:
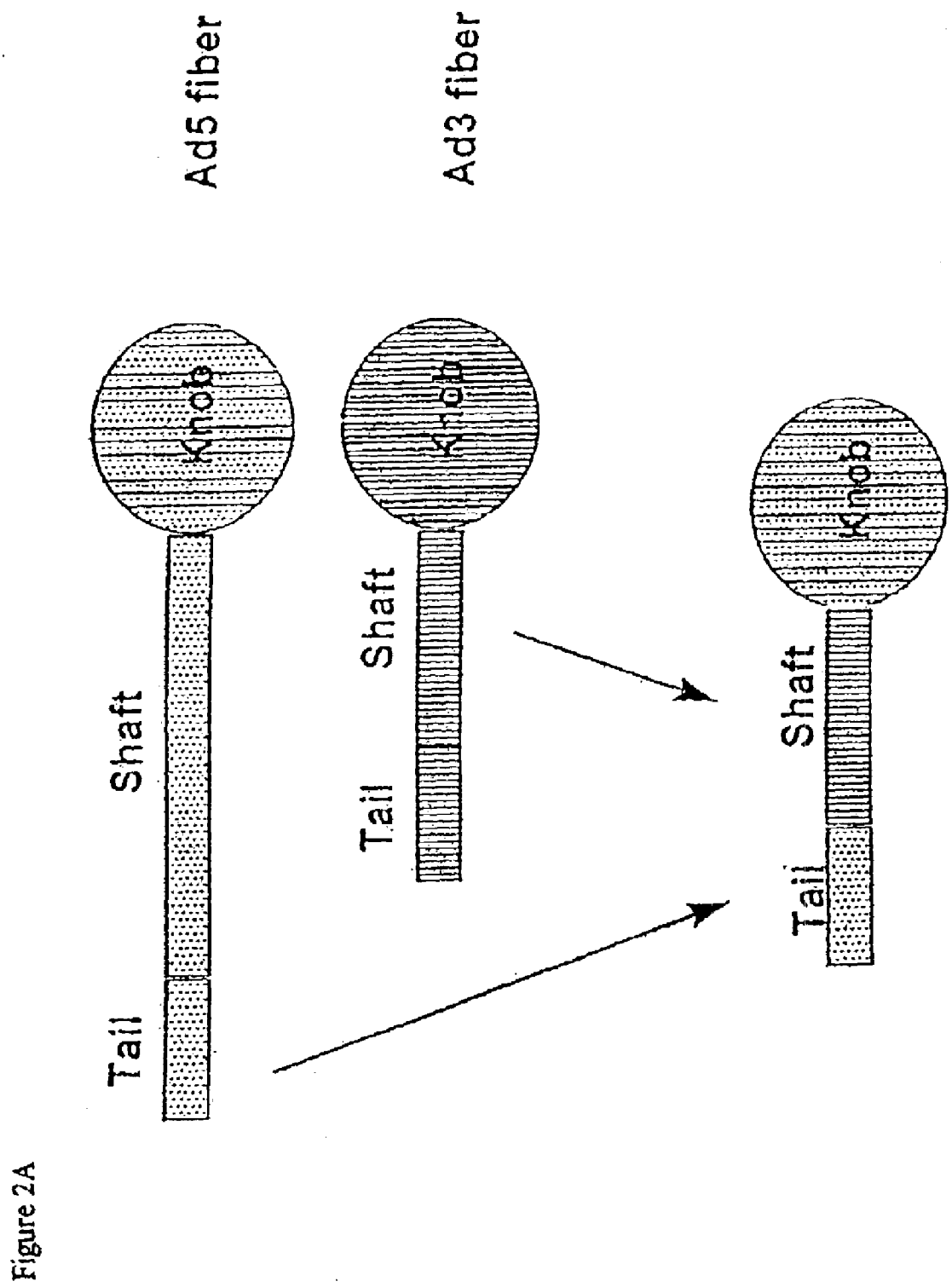
FIG. 2A. General structure of the shortened fiber construct in which the adenovirus serotype 3 (Ad3) shaft is inserted in place of the Ad5 shaft.
Figure 2B:
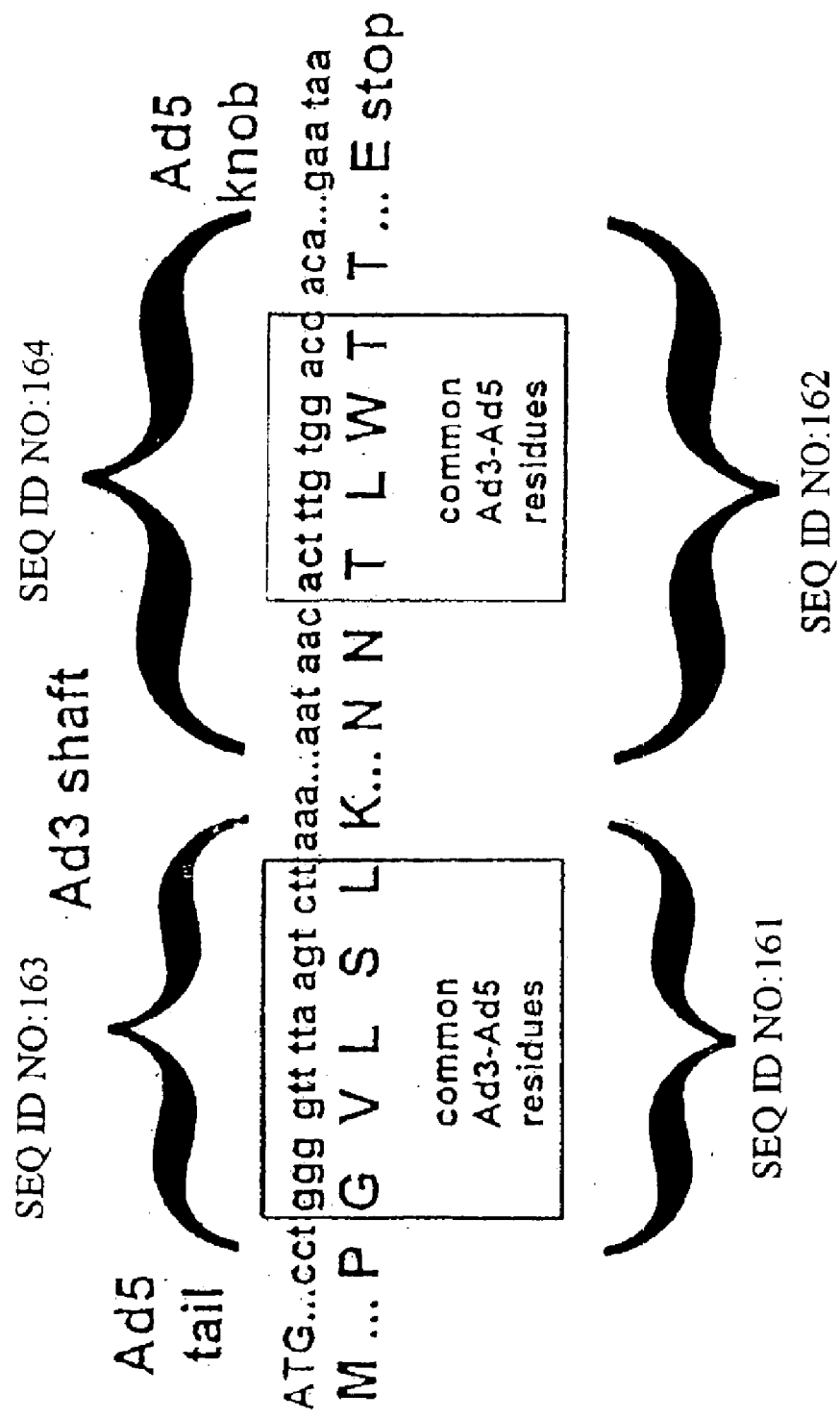
FIG. 2B. Detailed structure of the shortened fiber construct in which the adenovirus serotype 3 (Ad3) shaft is inserted in place of the Ad5 shaft. SEQ ID NOS: 161 and 162 illustrate portions of amino acid sequences of such a shortened fiber construct. SEQ ID NOS: 163 and 164 illustrate nucleic acid sequences that encode these amino acid sequences.

The underlined bases in the SOE35Kg primer fit with the sequence of the last repeat of the Ad3 fiber shaft, whereas the remaining ones correspond to the first nucleotides of the Ad5 fiber knob. The primer SOE35Kd nearly matches the Ad5 nucleotides 32634 to 32663 with a slight modification resulting in the creation of a SacI site. The two first PCR products were mixed, denatured and reannealed under PCR conditions, so that the top strand of the first product and the bottom strand of the second one overlap and act as primers on one another. The hybrid product was formed when this overlap was extended by polymerase. Inclusion of the primers SOE35Tg and SOE35Sd in the SOE reaction caused the recombinant product to be PCR amplified right after it is formed (see figure of Horton et al, previously cited). This resulted in a PCR product containing the Ad5 tail followed by the Ad3 shaft. Finally, the same SOE procedure was carried out with this last PCR product and the third PCR product using the primers SOE35Tg and SOE35Kd, giving rise to a DNA fragment containing an intertypic fiber composed of the Ad5 tail, the Ad3 shaft and part of the Ad5 knob, and flanked with the unique restriction sites SalI and SacI (FIG. 2). After digestion with these enzymes, the final PCR product was cloned into the SalI-SacI cleaved pXL2756 plasmid, resulting in the pIF1 shuttle plasmid.

Plasmids pSF1, pSF2 and pIF1 were sequenced.

Construction of the associated plasmid backbones and viruses. The three shuttle plasmids pSF1, pSF2 and pIF1 were recombined with the plasmid backbone pXL3006 (contains a PacI-excisable E1E3-deleted recombinant adenoviral genome with a CMV-lacZ expression cassette in place of the E1 region) in the G4977 bacterial strain according to the method described by Crouzet et al., supra, to obtain the plasmid backbones pBS1, pBS2 and pBI1, respectively. After cleavage with PacI, 2 $\mu$g (or 5 $\mu$g) of DNA were transfected in the 911 cells (or 293 or PER.6 cells) using Lipofectamine (Gibco BRL) to generate the corresponding viruses vBS1, vBS2 and vBI1. The intermediate plasmid backbones AE31, AE32 and AE33 were also constructed by homologous recombination between shuttle plasmid IE28 and the pBI1, pBS1 and pBS2 plasmid backbones. These plasmid backbones which contain a xylE expression cassette instead of the HVR5 hexon loop together with short-shafted fibers were further used to facilitate the recovery of plasmid backbones combining short-shafted fibers and HVR5-modified hexons (e.g., with insertion of UPAR- or integrin-binding peptides; see example 10).

In parallel, the intermediate plasmid backbones AE34, AE35 and AE36 were constructed by recombination between shuttle plasmid pJD3 and the pBI1, pBS1 and pBS2 plasmid backbones. These plasmid backbones were further used to facilitate the recovery of plasmid backbones combining short-shafted fibers and HI-modified fibers (e.g., with insertion of UPAR- or integrin-binding peptides).

Other methods. The cells, antibodies, viruses, immunoprecipitation assays, and neutralization assays were as described in Example 1, supra.

Results and Discussion

Viruses with shortened fiber proteins are expected to increase accessibility of binding peptides exposed at the hexon surface and/or reducing wild-type (i.e., native) virus/cell interactions. These constructs are summarized in Table 9.

TABLE 9

Shortened fiber protein adenoviruses.

| Virus | structure of the chimeric fiber |
|---|---|
| vBI1 | Ad5 tail - Ad3 shaft - Ad5 knob |
| vBS1 | Short-shafted fiber from Ad5 (deletion encompassing shaft repeats 4–16) |
| vBS2 | Short-shafted fiber from Ad5 (deletion encompassing shaft repeats 4–19) |

Viral productivity was drastically reduced in all three cases (although to different degrees), most likely because of the inability of the modified fibers to interact efficiently with its cellular receptor. That the defect occurred at such an early stage is indeed supported by normal viral DNA replication parameters in 293-infected cells (i.e., Xgal-positive), together with normal accumulation of viral late proteins. Also, Western blotting under non-denaturing conditions demonstrated that proper trimerization of the modified fibers occurred in all three cases.

Figure 3:
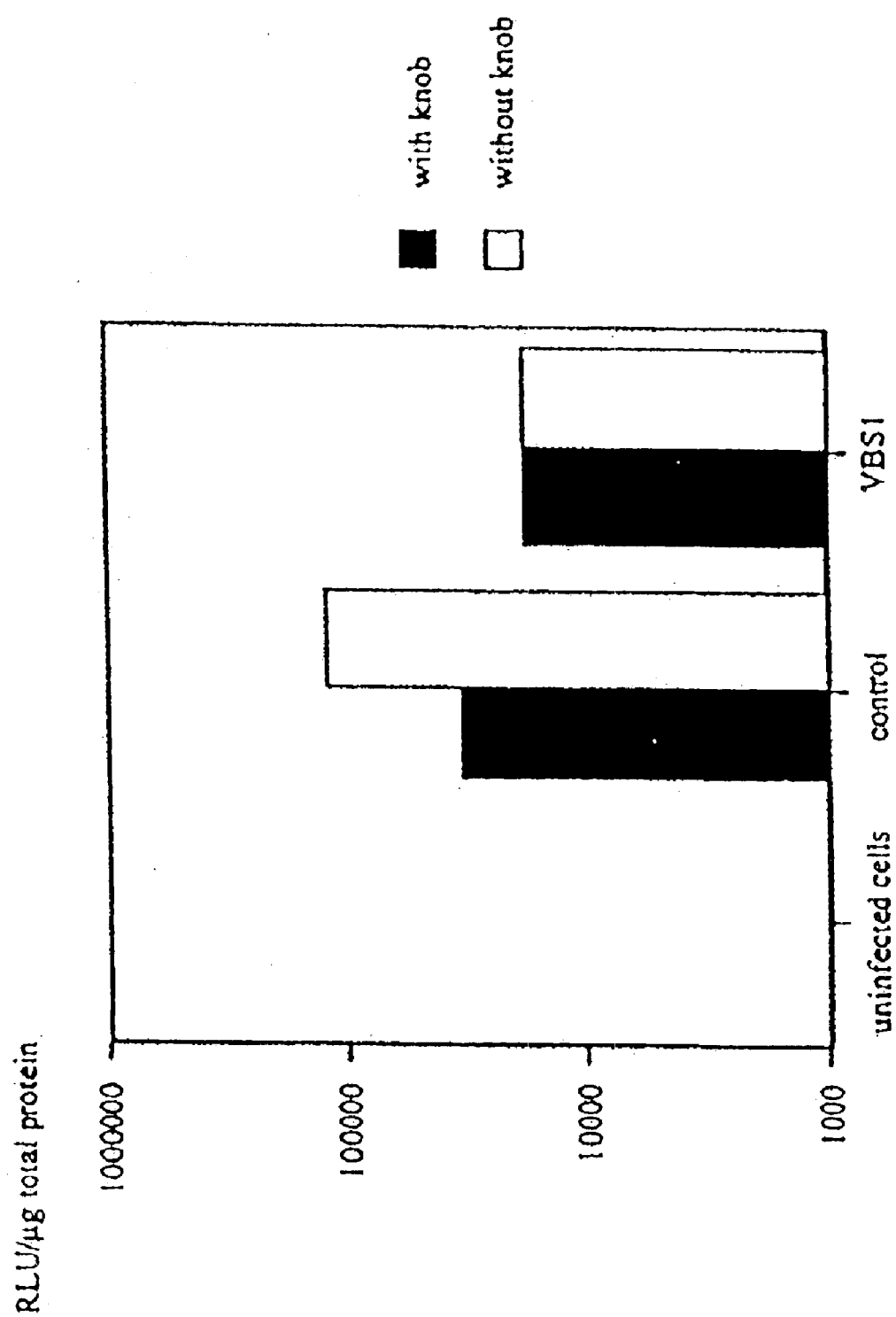
FIG. 3: Knob competition in 293 cells.

Although vBS1 binds less efficiently to CAR (Coxsackie and adenoviruses receptor)-positive cells, it could however be amplified in PER.C6 up to a lab-scale stock. As shown in FIG. 3, it was also observed that infection of 293 cells with vBS1 resulted in a 10-fold decrease in cell transduction as compared to that of a control virus displaying the native Ad5 fiber, which indicates a significant loss in Ad receptor binding. In this experiment, 293 cells were incubated with PBS or purified fiber knob (100 μg/ml) for 30 min at RT before infection at an moi of 50 (VP/cell) for 30 min at RT. Cells were then washed twice with PBS and furter incubated 24 h at 37° C. in medium before preparation of protein extracts. Specific lacZ expression was then quantified (units per protein extract).

Based on these data, C57/B16 mice were injected iv with the vBS1 construct or its control virus (unmodified shaft) to determine the profile of lacZ expression in major organs. Liver, heart and lung were analyzed for β-galactosidase expression by histochemistry. Results are presented in the following table 10 (% of XGal-positive cells: mean and range of values).

TABLE 10

Profile of transgene expression in major organs

| | injected dose (VP) | control virus | vBS1 |
|---|---|---|---|
| liver | $3.10^9$ (n = 5) | 15 (10–20) | 0 (0–0) |
| | $10^{10}$ (n = 5) | 50 (50–60) | 5 (2–5) |
| | $3.10^{10}$ (n = 5) | 50 (20–80) | 15 (10–20) |
| heart | $3.10^9$ (n = 5) | 0 | 0 |
| | $10^{10}$ (n = 5) | 0 | 0 |
| | $3.10^{10}$ (n = 5) | 0 | 0 |
| lung | $3.10^9$ (n = 5) | 0 | 0 |
| | $10^{10}$ (n = 5) | 0 | 0 |
| | $3.10^{10}$ (n = 5) | 0 | 0 |

These data indicate a dose-response effect for both adenoviruses in the liver, whereas no XGal-positive cells could be evidenced in the heart and lung tissues from either treated groups. Most interestingly, shortening of the fiber shaft resulted in a 10-fold decrease in liver transduction emphasizing the usefulness of manipulating the fiber shaft to direct infection mostly to the desired organs/cells in vivo, provided the recombinant adenovirus has been equipped with an additional, CAR-independent, entry pathway.

Example 4

Specific Targeting of Cells Expressing a Urokinase-type Plasminogen Activator Receptor Various high affinity uPAR-binding peptides were included within the hexon HVR5 and the fiber HI loops, or added to the C-terminal end of the fiber protein. These peptides originate either from wild-type ATF (Rettenberg et al., 1995, Biol. Chem. Hoppe-Seyler 376:587–594) and mutant ATF (Magdolen et al., 1996, Eur. J. Biochem. 237:743–751), a phage library (Goodson et al., 1994, Proc. Natl. Acad. Sci. 91:7129–7133), and an associated mutant, or human vitronectin (Waltz et al, 1997, J. Clin. Invest. 100:58–67). All viruses contain a gene expression cassette (lacZ or Gax) inserted in place of the E1 genes.

The methods for insertion of these peptides in the hexon HVR5 loop and the fiber protein HI loop were as described for the poliovirus epitopes in Examples 1 and 2, above. Shortening of the fiber protein was achieved as described in Example 3. Further Material and Methods are described hereunder.

Cell culturing of PERC6 cells

PER.C6 cells were grown in Dulbecco's modified medium (DMEM), 10% FCS and 10 mM $MgCl_2$ in a 10% $CO_2$ atmosphere at 37° C. (Fallaux et al , 1998, Hum Gene Ther, 9:1909–1917).

Recombinant adenoviral genomes

Recombinant adenoviral genomes were cloned into an RK2-derived plasmid by homologous recombinations in *E. coli* utilizing the EDRAG technology as described in the French application FR 2 730 504. The technology was simplified by replacing the ColE1 origin of replication by the origin of R6K in the suicide shuttle, as described in WO 97/10343, which allows recombination in any recA+ *E. coli* strain. Suicide plasmids (also referred to as shuttle plasmids) were constructed by inserted Ad5 sequence at appropriate restriction sites and by modifying sequences by sequential PCR. The integrity of the EDRAG constructs was assessed by restriction enzyme mapping and Southern analysis. The regions involved in PCR amplification or homologous recombination were verified by sequence analysis.

Plasmid backbone pXL3215 is a 57.8 kb long RK2 derivative that contains a PacI-excisable E1 and E3-deleted Ad5-based genome (French application FR 2 730 504) with an E. coli lacZ gene under control of the Rous Sarcoma Virus promoter instead of the E1 region. Plasmid pXL3527 derives from pXL3215 by exchanging the E. coli lacZ expression cassette by the human GAX expression cassette utilizing the suicide shuttle pXL3521; it leads to the generation of $AV_{1.0}CMV.Gax$ adenovirus. Plasmid pXL3497 derives from pXL2689 (Crouzet et al, Proc Natl Acad Sci USA, 1997, 94 :1414–1419) and displays a $(Gly-Ser)_5$-$(Lys)_7$ peptide at the C-terminus of the fiber protein. Following PacI restriction and transfection in E1-transcomplementing cells, this backbone was used to generate virus $AV_{1,k}CMV.lacZ$ which is identical to AdZ.F (pK7)bgal described by Wickham et al (1997, J Virol, 71:8221–8229).

Production and quantitation of adenoviruses

Transfections of adenoviral genomes in PER.C6 cells were performed in the presence of lipofectAMINE in T25cm² flasks. Briefly, 5 µg of PacI-digested DNA plasmid diluted into $H_2O$ were mixed with 23 µl of Lipofectamine. After gentle mixing, the suspension was incubated for 30 min at room temperature. In the meantime, the cells at 50–60% confluence were washed twice with phosphate buffered saline which was then replaced by the LipofectAMINE/DNA mixture to which 3.8 ml of DMEM without serum were added. The cells were incubated at 37° C. for 5 to 8 hours, after which the medium was replaced by DMEM containing 10% fetal calf serum and 10 mM $MgCl_2$. Three days after transfection the cells were split into one T75cm2 flask. Cells and supernatant were harvested at full CPE (day 10–14) and freeze/thawed for three cycles followed by centrifugation and collection of the supernatant. The EDRAG technology generates a homogenous (i.e., clonal) population; therefore plaque purification is not necessary.

Adenoviral particles were precisely quantified by chromatography on a Sepharose type support.

PER.C6 cells were infected at a confluence of approximately 70% with recombinant adenovirus at an MOI between 10 and 100 viral particles per cell in T150 cm² flasks. When the cytopathic effect was complete, cells and supernatant were harvested, freeze/thawed for 3 cycles, centrifuged and the supernatant collected. In certain cases, the recovery process had to be adapted (see below).

Infectivity of the modified viruses was assessed in vitro in primary cells of various origin (with a special emphasis for smooth muscle cells and endothelial cells of human origin), and a panel of human and non-human tumor cell lines that are refractory to infection because they express limiting levels of adenovirus receptor at their cellular surface (see examples 8 to 10). Recombinant knob was used as a competitor when cells easily infectable by Ad5 were used.

Viruses modified in the HI loop by insertion of a peptide targeting uPAR.

Residues 538 to 548 of the Ad5 fiber (GTQETGDTTPS) (SEQ ID NO:72) were deleted and replaced with 6 different peptides flanked with GSS linkers. Construction of the corresponding shuttle plasmids, plasmid backbones and viruses were carried out as detailed in Example 2. All viruses were viable, but some (especially viruses AE43, AE44 and AE45) presented an altered stability as compared to their unmodified control virus. It was however possible to get yields comparable to a control virus (i.e., 10000–20000 VP/cell) by adapting the procedure: PER.C6-infected cells were harvested 3 days post infection and lysed using a mild buffer (Tris 10 mM pH7.5, MgCl2 1 mM, Tween 20 1%, NaCl 0,25M) instead of successive freezing/thawing cycles; viruses were then purified by ultracentrifugation on CsCl gradients.

TABLE 11

HI loop insertion of uPAR targeting peptides.

| adenoviral plasmid | Selected peptide | Peptide sequence with linkers | Seq ID No: |
|---|---|---|---|
| pAE42 | ATF domain (aa 14 to 32 of mature human urokinase) | gly-ser-ser-LNGGTCVSNKYFSNIHWCN-gly-ser-ser | 16 |
| pAE45 | Mutated ATF domain (increased affinity for uPAR) | gly-ser-ser-LNGGTAVSNKYFSNIHWCN-gly-ser-ser | 17 |
| pAE48 | Peptide selected by phage-display | gly-ser-ser-AEPMPHSLNFSQYLWYT-gly-ser-ser | 19 |
| pAE46 | A mutant of the above selected peptide | gly-ser-ser-AEPMPHSLNFSQYLWT-gly-ser-ser | 18 |
| pAE43 | UPAR-binding peptide (Vn4) from human vitronectin | gly-ser-ser-RGHSRGRNQNSR-gly-ser-ser | 20 |
| pAE44 | UPAR-binding peptide (Vn3) from human vitronectin | gly-ser-ser-NQNSRRPSRA-gly-ser-ser | 21 |

Viruses modified in the HVR5 loop by insertion of a peptide targeting uPAR.

Viruses modified in the HVR5loop by insertion of a peptide targeting uPAR.

Residues 269 to 281 of the Ad5 hexon (TTEATAGNGDNLT) (SEQ ID NO:125) were replaced with the above 6 uPAR-binding peptides flanked on both sides by suitable linkers (gly-ser). Construction of the corresponding plasmid backbones and adenoviruses were carried out as in Example 1. All viruses were viable. Some of the constructs (e.g., AE27, AE28) displayed some unstability and were purified accordingly (see above).

TABLE 12

HVR5 loop insertion of uPAR targeting peptides

| Adenoviral plasmid | Selected peptide | Peptide sequence with linkers | Seq ID No: |
|---|---|---|---|
| pAE26 | ATF domain | gly-ser-LNGGTCVSNKYFSNIHWCN-gly-ser | 7 |
| pAE29 | Mutated ATF domain | gly-ser-LNGGTAVSNKYFSNIHWCN-gly-ser | 8 |
| pAE47 | Peptide selected by phage-display (Goodson et al., 1994, PNAS 91:7129–7133) | gly-ser-AEPMPHSLNFSQYLWYT-gly-ser- | 10 |
| pAE30 | A mutant of the above selected peptide | gly-ser-AEPMPHSLNFSQYLWT-gly-ser- | 9 |
| pAE27 | UPAR-binding peptide (Vn4) from human vitronectin | gly-ser-RGHSRGRNQNSR-gly-ser | 11 |
| pAE28 | UPAR-binding peptide (Vn3) from human vitronectin | gly-ser-NQNSRRPSRA-gly-ser | 12 |

Viruses modified in the HI loop by insertion of a peptide targeting uPAR and harboring shortened fibers.

Residues 538 to 548 of the Ad5 fiber (GTQETGDTTPS) (SEQ ID NO:72) were deleted and replaced with 6 uPAR-binding peptides flanked on both sides by suitable linkers (gly-ser-ser) as described above. These modifications were combined with shortened fiber shafts (see Example 3) as summarized in the following table:

TABLE 13

Class of short-shafted viruses modified in the HI loop by insertion of a peptide targeting uPAR

| Tail | Shaft | Knob modification |
|---|---|---|
| Ad5 tail | Ad3 shaft | Ad5 HI loop insertions |
| Ad5 tail | repeats 1 to 3 and 17 to 22 of Ad5 | Ad5 HI loop insertions |
| Ad5 tail | repeats 1 to 3 and 20 to 22 of Ad5 | Ad5 HI loop insertions |

Viruses modified in the HVR5 loop by insertion of a peptide targeting uPAR and harboring shortened fibers.

Residues 269 to 281 of the Ad5 hexon were replaced with 6 different peptides flanked by suitable linkers (gly-ser) as described above. These modifications were further combined with the shortening of the fiber shaft as described above.

For example, virus AE65 contains the NQNSRRPSRA peptide (SEQ ID NO:6) flanked by gly-ser tinkers in place of hexon HVR5 and displays a shortened fiber (shaft deletion encompassing repeats 4 to 16). Another example is virus AE63 which is identical to AE65 except that it contains the DCRGDCF peptide (SEQ ID NO:148) instead of the Vn3 peptide (see Example 10, FIG. 13).

Viruses modified for targeting by a C-terminal addition of an 8 amino acids linker followed by a peptide targeting uPAR.

The stop codon of the fiber is replaced with the proline codon of the linker. The linker sequence used for all constructs was PKRARPGS (SEQ ID NO:149).

The 3'end of the fiber protein coding sequence was modified to introduce an FspI site. PCR mutagenesis was used to generate a single base substitution (nucleotide 32778) which creates a silent mutation introducing a novel recognition site for FspI. The Ad5 fiber knob was amplified from the Ad5 genome using primers MOL1 (5'-ggaactttagaaatggagatcttactgaagg-3') (SEQ ID NO:126) and MOL3 (5'-cgattctttattcttgcgcaatgtatgaaaaag-3') (SEQ ID NO:127). The primer MOL3 nearly matches the Ad5 nucleotides 32762–32794 with a slight modification resulting in the creation of the FspI restriction site. This amplification product was introduced in pCR2.1 (Invitrogen) to create pMA51.

The region downstream from the stop codon of the fiber protein coding sequence was modified by PCR-mutagenesis to introduce AatII, NruI, SpeI restriction sites upstream the polyA region using the oligonucleotides MOL2 (5'-cttaagtgagctgcccgggag-3') (SEQ ID NO:128) and MOL4 (5'-ggatccaatgaacttcatcaagt-3') (SEQ ID NO: 129), and cloned in pCR2.1 (Invitrogen) to create pMA52.

The sequence coding for the linker peptide was created by annealing of two single-stranded oligonucleotides: MOL7 (5'-aattctgcgcaagaaccaaagagggccaggcccggatcctaagacgtct-3') (SEQ ID NO:130) and MOL8 (5'-ctagagacgtcttaggatccgggcctggccctctttggttcttgcgcag-3') (SEQ ID NO:131). This duplex was cloned between the EcoRI and XbaI sites of pBSSK+ (Stratagene) creating pMA53.

Finally, the linker sequence was introduced at the 3'-end of the fiber protein coding sequence by cloning the fragments BglII-FspI from pMA51 and FspI-XbaI from pMA53 into the BamHI and XbaI sites of pXL2756 to create the vector pMA55.

The shuttle vector pMA56 was constructed by cloning the SmaI-AatII fragment of pMA52 into pMA55 SmaI-AatII restriction sites. Shuttle plasmid pMA55 was recombined with plasmid backbone pXL3006 in the G4977 bacterial strain according to the method described by Crouzet et al., supra, to obtain the plasmid backbone 22.3 which contains a PacI-excisable E1E3-deleted CMV/lacZ recombinant viral genome encoding fibers with C-terminal modifications.

Further cloning were performed to add the uPAR-targeting ligands at the C-ter of the fiber using a PKRAR-PGS linker. Briefly, shuttle plasmids encoding these modifications were constructed and recombined with adenoviral plasmid backbones pXL3091 (RSV-lacZ in place of E1), pXL3006 (CMV-lacZ in place of E1) or pXL3527 (hGax expression cassette in place of E1) in the G4977 bacterial strain according to the EDRAG method to generate adenoviral backbones displaying lacZ or Gax expression cassettes and C-terminally modified fiber proteins.

With the exception of bC12x, all expected viruses were recovered following transfection of PacI-restricted backbones into 911, 293 or PER.C6 cells. Their productivity (VP/cell) was comparable with that of their unmodified control virus.

TABLE 14

Viruses modified by a C-terminal addition of an 8 amino acids linker followed by a peptide targeting UPAR.

| adenoviral backbones/viruses | Selected peptide | Sequence of the peptide | Seq. ID No: |
|---|---|---|---|
| bc9x (RSV lacZ) | ATF domain (from aa 14 to 32) | LNGGTCVSNKYFSNIHWCN | 1 |
| bc10x (RSV lacZ) | mutated ATF domain (from aa 14 to 32) | LNGGTAVSNKYFSNIHWCN | 2 |
| bc12x (RSV lacZ) | peptide selected by phage-display | AEPMPHSLNFSQYLWYT | 4 |
| bc11x (RSV lacZ) | a mutant of the above selected peptide | AEPMPHSLNFSQYLWT | 3 |
| bc13x (RSV lacZ) | vitronectin uPAR-binding domain Vn3 | NQNSRRPSRA | 6 |
| bc14x (RSV lacZ), bc15x (CMV lacZ) and pXL3570 (Gax) | vitronectin uPAR-binding domain Vn4 | RGHSRGRNQNSR | 5 |

In additional experiments, these modifications were combined with shortening the fiber shaft as examplified above.

Example 5

Specific Targeting of Cells Expressing an αv Integrin Receptor

A high affinity αv integrin binding peptide (CDCRGDCFC (SEQ ID NO: 124) refered to as RGD-4C; see also Pasqualini et at., 1997, Nature Biotech. 15:542) and a variant thereof (DCRGDCF (SEQ ID NO: 148) refered to as RGD-2C) have been included within the fiber HI hexon and the HVR5 loops, or added to the C-terminal end of the fiber protein. These viruses contain a heterologous gene (lacZ) inserted in the E1 region, which has been deleted from the viruses.

The methods for insertion of these peptides in the hexon HVR5 loop and the fiber protein HI loop were as described for the poliovirus epitopes as described in Examples 1 and 2, above.

Viruses modified in the HI loop by insertion of a peptide targeting αv integrins, associated or not with a shortened fiber.

Residues 538 to 548 of the Ad5 fiber were deleted and replaced with the peptide flanked with GSS linkers. Adenoviral plasmid backbones containing a CMVlacZ expression cassette were transfected in PER.C6 cells: virus AE60 was viable and could be amplified in PER.C6 cells with a productivity comparable to a control virus, whereas repeated transfection of PacI-digested pAE59 DNA did not generate the corresponding virus, suggesting that this particular construct could not grow efficiently.

TABLE 15

Viruses modified in the HI loop by insertion of a peptide targeting αv integrins

| adenoviral backbones | Selected peptide | Sequence of the peptide with linkers | SEQ ID NO: |
|---|---|---|---|
| pAE59 | CDCRGDCFC (SEQ ID NO: 124) | gly-ser-ser-CDCRGDCFC-gly-ser-ser | 22 |
| pAE60 | DCRGDCF | gly-ser-ser-DCRGDCF-gly- | 23 |

TABLE 15-continued

Viruses modified in the HI loop by insertion of a peptide targeting αv integrins

| adenoviral backbones | Selected peptide | Sequence of the peptide with linkers | SEQ ID NO: |
|---|---|---|---|
| | | (SEQ ID NO 148) ser-ser | |

Viruses modified in the HI loop by insertion of a peptide targeting αv integrins, associated with a shortened fiber are also obtained.

Viruses modified in the HVR5 loop by insertion of a peptide targeting αv integrins, associated or not with a shortened fiber.

The amino acids 269 to 281 of the Ad5 hexon were deleted and replaced with the peptide (the same sequences as described in the table above were used) flanked with GS linkers. Adenoviral plasmids containing a LacZ or a hGax expression cassette were transfected in PER.C6 or 911 cells leading to the recovery of all 3 viruses. A loss of productivity was observed for AE58 and AE63 viruses in 293 cells, whereas AE57 behaved normally: this is likely due to an incorrect folding/stability of the hexon in the case of AE58, and to the decrease in Ad receptor binding of the shortened fiber in the case of AE63.

TABLE 16

Viruses modified in the HVR5 loop by insertion of a peptide targeting αv integrins, associated or not with a shortened fiber

| adenoviral backbones | Selected peptide | Sequence of the peptide with linkers | SEQ ID NO: | Features of fiber shaft |
|---|---|---|---|---|
| pAE58 | CDCRGDCFC (SEQ ID NO: 124) | gly-ser-CDCRGDCFC-gly-ser | 13 | unmodified |
| pAE57 (LacZ) and pXL3664 (Gax) | DCRGDCF (SEQ ID NO: 148) | gly-ser-DCRGDCF-gly-ser | 14 | unmodified |
| pAE63 | DCRGDCF (SEQ ID NO: 148) | gly-ser-DCRGDCF-gly-ser | 14 | shortened 22 of Ad5 |

The inclusion of the RGD-2C peptide in the hexon was also combined with the addition of the linker-peptide sequence PKRARPGS-K7 (SEQ ID NO: 132) at the C-terminus of the fiber. The corresponding virus was viable.

Example 6

Construction of Heparan Sulfate Proteoglycans Targeted Viruses

Fiber-modified adenoviruses containing a lacZ or Gax expression cassette were constructed by genetic modification of the adenoviral genome in *E. coli* using the EDRAG technology and produced in 911 or PER.C6 cells (see Material and Methods of Example 4).

Three ligands expected to bind to heparan sulfate proteoglycans were identified: the heptalysine stretch (K7) described by Wickham et al. (1997, J Virol, 71:8221–8229), the arginine-leucine repeated motif RRLLRRLLRR (SEQ ID NO:133), described in patent application WO95/21931, and the peptide fragment from FGF-1 binding to heparin KRGPRTHYGQK (SEQ ID NO: NO:134) described by Digabriele et al (1998, Science, 393:812–817).

Among others, five viruses have the heptalysine K7 stretch at the C-terminus of the fiber and differ by the transgene (lacZ or Gax) and/or the identity of the connecting (no linker, (GS)5 or PKRARPGS). Virus 3497 was included as a reference (Wickham et al., 1997, J Virol, 71:8221–8229). The importance of the linker and/or peptide in terms of viral production and transduction efficacy in vitro and in vivo was then assessed.

A polylysine stretch has also been included within the hexon HVR5 or the fiber HI loops in viruses containing a heterologous gene (lacZ) inserted in the E1 region

TABLE 17

Heparan Sulfate Proteoglycans Targeted viruses

| adenoviral backbones | Modification of the capsid |
|---|---|
| pAE61 | Substitution of hexon aa 269–281 with GS-K5-GS (SEQ ID NO: 135) |
| pAE62 | Substitution of fiber aa 538–548 with GSS-K7-GSS (SEQ ID NO: 136) |
| pXL3497 (lacZ) and pXL3528 (gax) | (GS)5-K7 (SEQ ID NO: 137) added to the fiber C-terminus |
| pXL3496 (lacZ) and pXL3569 (gax) | PKRARPGS-K7 (SEQ ID NO: 138) added to the fiber C terminus |
| pXL3631 (lacZ) | K7 (SEQ ID NO: 139) added to the fiber C-terminus |
| pXL3662 (lacZ) and | PKRARPGS-KRGPRTHYGQK (SEQ ID NO: 140) |

TABLE 17-continued

Heparan Sulfate Proteoglycans Targeted viruses

| adenoviral backbones | Modification of the capsid |
|---|---|
| pXL3665 (gax) | added to the fiber C-terminus |
| pXL3663 (lacZ) and pXL3666 (gax) | PKRARPGS-RRLLRRLLRR (SEQ ID NO: 141) added to the fiber C-terminus |

All these viruses were viable and could be amplified in E1 transcomplementing cells. The following table 18 summarizes the yield obtained in one experiment performed in PER.C6 cells after infection of the cells at moi 10 to 100 VP/cell.

TABLE 18

Amplification of viruses in PER.C6 cells

| Virus | Viral particles/cell |
|---|---|
| 3497 | 1200 |
| 3528 | 2300 |
| 3496 | 2700 |
| 3569 | 1000 |
| 3631 | 6000 |
| 3662 | 12160 |

Productivity was differently affected by these C-terminal fiber extensions. Overall, these and other data indicate that the presence and identity of the connecting linker sequence added to the fiber C-terminus greatly influences the adenovirus infection cycle/behavior. For a given linker sequence, the identity/nature of the foreign peptide per se was also found to be an important parameter. For example, the construct with the RRLLRRLLRR peptide (SEQ ID NO: 133: $AV_{1,r}CMV.lacZ$ or Ad3663) yielded very low titers whereas its replacement by the KRGPRTHYGQK peptide (SEQ. ID NO: 134; $AV_{1,f}CMV.lacZ$ or Ad3662) restored productivity.

The recovery process had also to be optimized for most of these viruses. For example, a total of $5.10^{12}$ VP of Ad3497 was successfully purified by a two-step chromatography procedure and finally resuspended in Tris 20 mM pH8.4–10% glycerol, with an overall particle recovery of 68% as described hereabove.

Example 7

Construction of Viruses with a Vn4 Peptide within the HI Loop

As mentionned in example 4, the AE43 virus somehow displayed some levels of unstability that required an optimized recovery process. To rescue its stability without loosing its advantageous binding characteristics, the Vn4 peptide was introduced in the HI loop in various neighboring contexts (see following table 19). The corresponding viruses (which contained a lacZ or Gax expression cassette in place of E1) were constructed by recombinational cloning in *E. coli* and amplified in 911 or PER.C6 cells as described in Example 4.

TABLE 19 viruses with a Vn4 peptide in the HI loop

| virus | Modification of the capsid | SEQ ID NO: |
|---|---|---|
| AE43 | Substitution of fiber aa 538–548 with GSS-Vn4-GSS | 20 |
| GL11 | Substitution of fiber aa 538–548 with GSS-Vn4 + Vn3-GSS* | 143 |
| GL12 | Substitution of fiber aa 538–548 with GTSE-Vn4-GSS | 144 |
| GL13 | Substitution of fiber aa 538–548 with GTQE-Vn4-GSS | 145 |
| GL14 | Substitution of fiber aa 538–548 with GSSS-Vn4-GSS | 146 |
| GL16 | Substitution of fiber aa 538–548 with GSS-Vn4-GGS | 147 |
| GL17 | Substitution of fiber aa 541–548 with SS-Vn4-GSS | 142 |
| 3630 (lacZ) and 3629 (Gax) | Insertion of SS-Vn4-GS between fiber aa 546 (Thr) and 547 (Pro) | 150 |

*Vn4 + Vn3 = RGHSRGRNQNSRRPSRA is derived from human vitronectin

Almost all constructs exhibited a productivity that was comparable to that of their unmodified control virus (see following table 20):

TABLE 20

| Virus | Viral particles/cell |
|---|---|
| control virus | 20000 (n = 2) |
| AE43 | 20000 (n = 2) |
| GL11 | 200 (n = 1) |
| GL12 | 20000 (n = 3) |
| GL13 | 25000 (n = 2) |
| GL14 | 20000 (n = 1) |
| GL16 | 4000 (n = 2) |
| GL17 | 15000 (n = 3) |
| 3630 | 10000 (n = 3) |
| 3629 | 14000 (n = 1) |

Virus stability was also differently affected by these modifications. In particular, some of them (e.g., AE43, GL11, GL14 and GL16) were sensitive to successive rounds of freezing/thawing so the infected cells had to be lysed in mild conditions (Tris 10 mM pH 7.5, MgCl2 1 mM, Tween 20 1%, NaCl 0,25M) for recovery, again emphasizing the influence of the linker sequences on the virus behavior (see also Example 9, FIG. 12).

Example 8

Evaluation of Targeted Viruses in Human Primary Cells

Materials and Methods

Cell culture

Primary cultures of rat and rabbit smooth muscle cells were prepared from thoracic aortas of adult male Spraggue-Dawley rats or of adult New Zealand White rabbits according to Mader et al (1992, J Gerontol. Biol. Sci. 47: b32–b36). Cells were propagated at 37° C. in Dulbecco's modified Eagle's medium (DMEM) containing 10% fetal bovine serum (FBS) and penicillin/streptomycin. Human aorta smooth muscle cells and HUVEC were purchased from Clonetics and cultured following instructions of the manufacturer.

Adenoviral mediated in vitro gene transfer and gene expression assays

Cells were seeded onto 24-well or 12-well plates one to two days prior to experiments. Cells were infected at moi 100 or 1000 (VP/cell) by incubation of the adenoviral vector diluted in serum free culture medium for one hour at 37° C. Cells were then washed and growth medium was added for 48 hours to allow β-galactosidase expression. The cells were then lysed and assayed for β-galactosidase activity by using Luminescent β-galactosidase genetic reporter system II (Clontech), or Xgal stained.

Results

Construction encoding β galactosidase reporter gene

Data presented in the two following tables 21 and 22 show that most viruses are able to transduce hSMC more efficiently than a control virus, and that viruses AE30, AE42, AE43, AE44, AE45, AE57, AE58, AE61, AE62, BC15X and 3497 are good candidates for further in vitro and in vivo studies. Experiments performed on primary SMCs infected at an moi of 1000 VP/cell at different passage demonstrated a very significant gain of transduction for several of the modified viruses (examples are provided in tables 21 and 22). Extracts were prepared 48 hr post-infection at which time protein and β-galactosidase activity were quantified. Transduction efficacy was then assessed by comparing the levels of lacZ specific activity (RLU/protein extract).

TABLE 21

Experiment #1

| Virus | Transduction efficacy in human SMC |
|---|---|
| control | 1 |
| AE30 | 3.5 |
| AE43 | 53 |
| AE44 | 23 |
| AE45 | 10 |
| 3497 | 115 |
| BC15X | 26 |

TABLE 22

Experiment #2

| Virus | Transduction efficacy in human SMC |
|---|---|
| control | 1 |
| AE27 | 16 |
| AE29 | 6 |
| AE30 | 133 |
| AE42 | 95 |
| AE43 | 825 |
| AE48 | 31 |
| AE57 | 846 |
| AE58 | 264 |
| AE60 | 52 |
| AE61 | 781 |
| AE62 | 772 |
| BC15X | 47 |

The following table 23 summarizes the data obtained in SMC from different species: most viruses were able to efficiently transduce non-human cells, indicating that there is no species barrier in their entry pathway.

TABLE 23 infection of SMC from different species

| Virus | Transduction efficacy in rat SMC | Transduction efficacy in pig SMC | Transduction efficacy in rabbit SMC |
|---|---|---|---|
| control | 1 | 1 | 1 |
| BC15X | — | 97 (n = 1) | — |
| AE 43 | 77 (n = 2) | 753 (n = 2) | 131 (n = 3) |
| AE 62 | 166 (n = 2) | 2166 (n = 2) | 320 (n = 5) |
| 3497 | 50 (n = 2) | 349 (n = 2) | 55 (n = 2) |
| 3496 | 295 (n = 2) | 2318 (n = 2) | 437 (n = 2) |
| AE 57 | — | 2960 (n = 1) | — |
| AE 63 | 21 (n = 2) | 293 (n = 2) | 23 (n = 2) | n = number of experiments

To demonstrate that the increase of transduction observed following capsid modification was due at least in part to an increase in infectivity, quantitative PCR was carried out on viral DNA extracted from infected human SMC at moi 1000 VP/cell. Simultaneously, RLU measurements were performed on protein extracts.

Table 24 indicates that the gain in human smooth muscle cells transduction efficiency that caracterized the best candidate viruses correlated in all cases (although to different extents) with an increase in DNA entry. The correlation was especially good for viruses AE43 and BC15X.

TABLE 24 genome delivery and transgene expression

| virus | Genomes/ cell$^a$ | RLU/µg total protein | Ratio RLU | Ratio genomes |
|---|---|---|---|---|
| control | 3, 3 | 191641 | 1 | 1 |
| AE30 | 211 | 677345 | 3, 5 | 64 |
| AE43 | 87 | 10207798 | 53 | 26, 5 |
| AE45 | 427 | 1851206 | 10 | 130 |
| 3497 | 124 | 22115125 | 115 | 38 |
| BC15X | 40 | 5004672 | 26 | 12, 3 |

$^a$genomes/cell is the ratio between the amount of viral genomes as quantified by PCR and the number of infected cells.
$^b$ratio RLU: ratio between the RLU level of the indicated virus and the RLU level of the control virus
$^c$ratio genomes: ratio between the genomes amount of the indicated virus and the genomes amount of the control virus.

Figure 4:
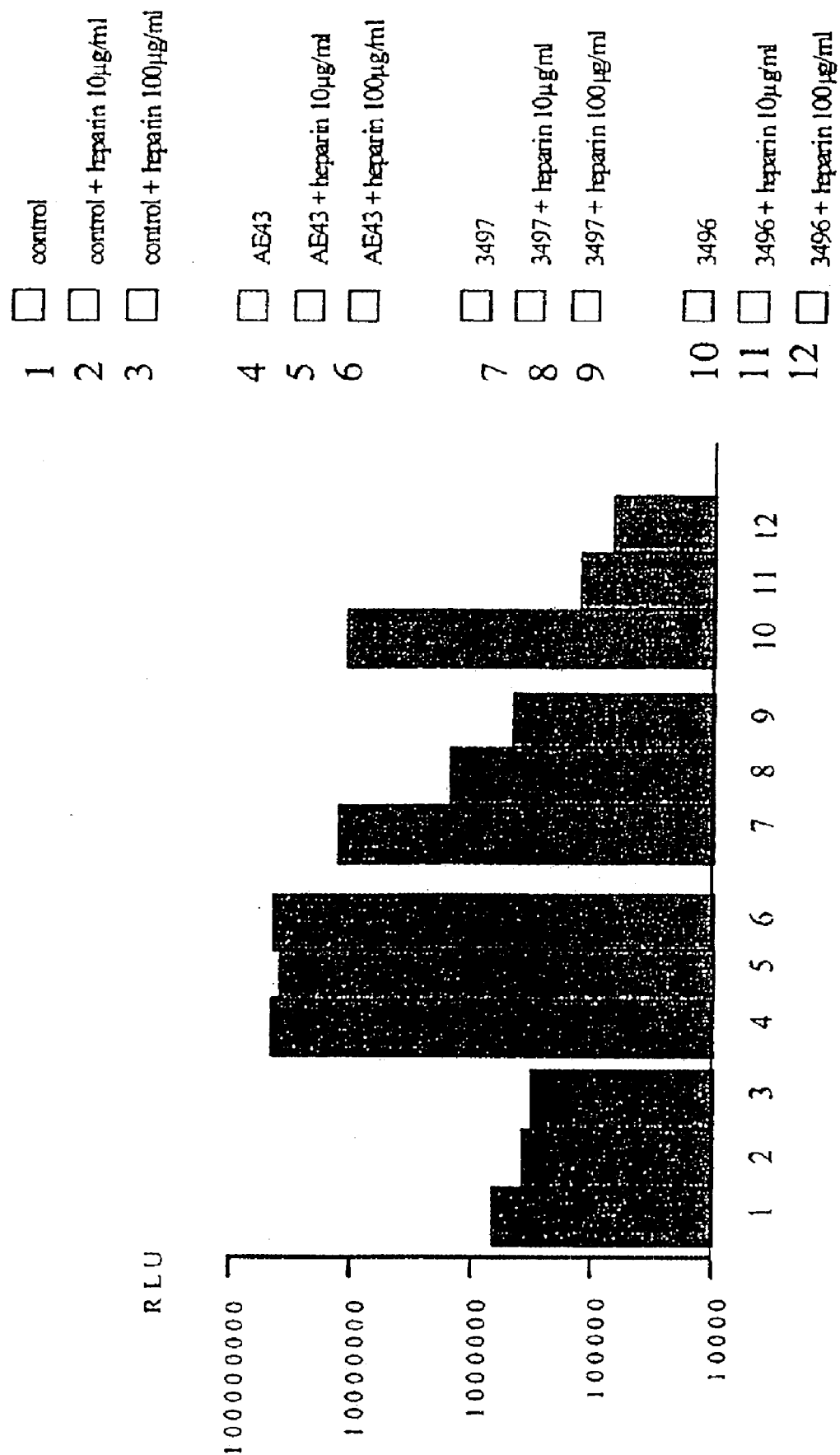
FIG. 4: Infection of hSMC with various viruses in presence of increasing doses of soluble heparin.
Figure 5:
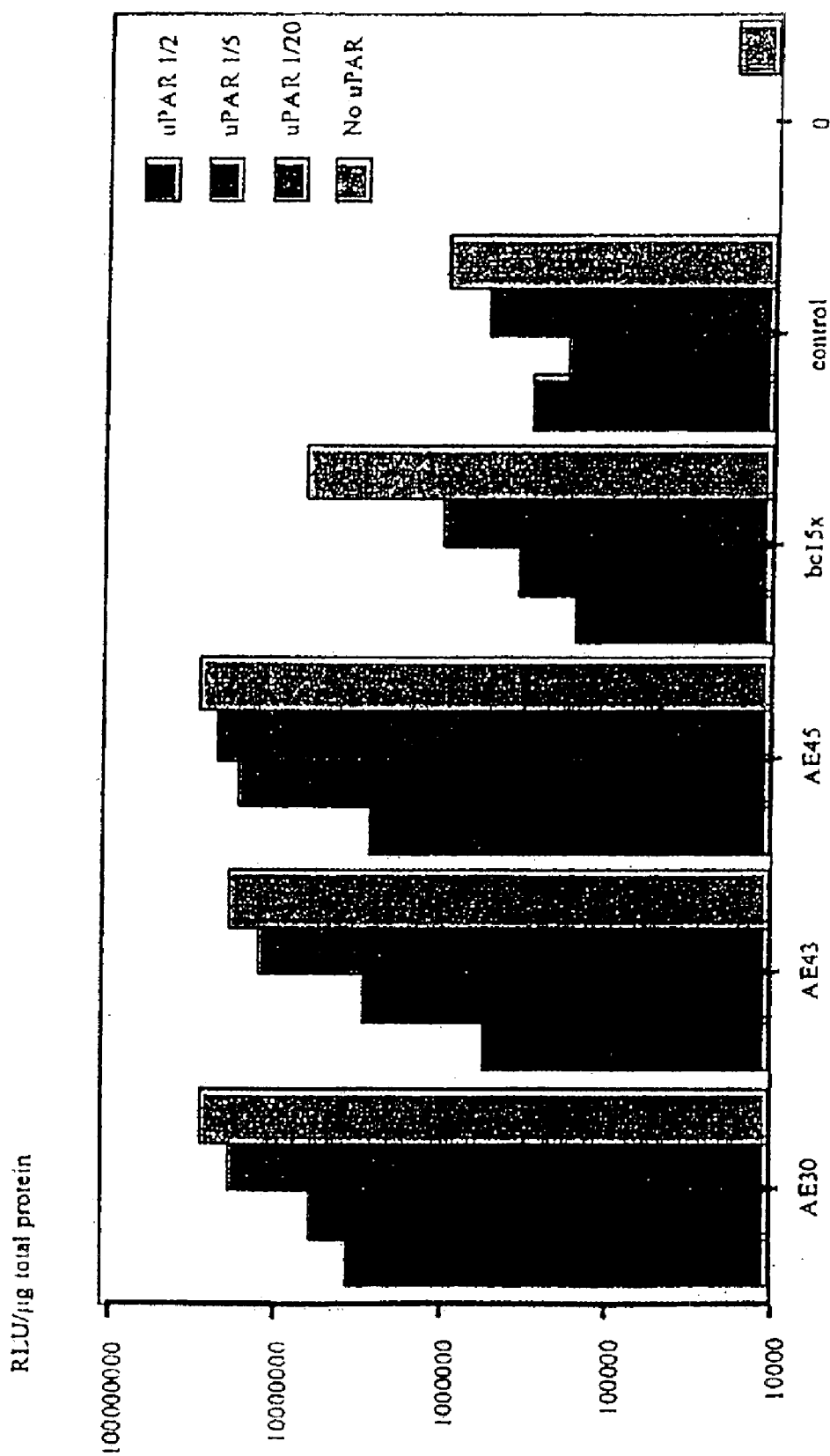
FIG. 5: Infection of hSMC with viruses preincubated with increasing doses of soluble uPAR.

The entry pathway in SMC was also analyzed in competition with soluble heparin or soluble uPAR as illustrated in FIGS. 4 and 5.

In FIG. 4, hSMC were infected at moi 1000 (VP/cell) in presence of increasing doses of soluble heparin. Cells were washed in PBS before further incubation at 37° C. Extracts were prepared 48 hr post-infection at which time total proteins and β-galactosidase activity were quantified. The data show that infection of hSMC by polylysine-containing viruses is specifically inhibited by soluble heparin showing that these viruses likely bind to cellular heparan sulfate proteoglycans at the cell surface. In contrast, and as expected, AE43 does not use this particular pathway for entry.

In FIG. 5, viruses were preincubated with increasing doses of soluble uPAR (0 to 9,4 µg/ml) before incubation on hSMC at moi 1000 (VP/cell). Cells were washed in PBS before further incubation at 37°. Extracts were prepared 48 hr post-infection at which time total proteins and β-galactosidase activity were quantified. The data show that infection of hSMC by some of the uPAR-targeting viruses (e.g., AE43) is specifically inhibited by recombinant soluble uPAR. That hSMC express uPAR at their cellular surface (data not shown) strongly suggests the use of this particular receptor for cellular entry.

Gax encoding targeted adenoviruses

Gax expression level in infected hSMC was analyzed by Western blot (following figures). The highest increase in Gax expression was obtained after infection with virus 3528 (K7 at the C-terminus of the fiber). Gax protein was detected with all modified viruses at moi 3000 VP/cell, whereas Gax expression in cells infected with the control virus at the same moi was undetectable.

Figure 6:
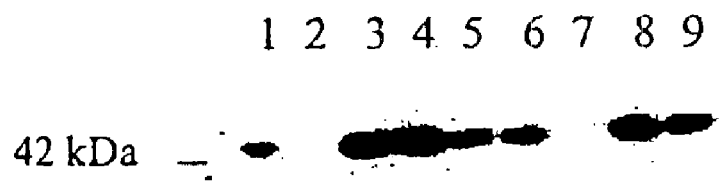
FIGS. 6 and 7: Gax expression in human SMC infected with targeted adenovirus.

FIG. 6 illustrates the Gax expression in human SMC infected with targeted adenovirus. Protein extracts were prepared 24 hours after infection at the indicated moi (VP/cell). (1) $AV_{1.0}CMVrGax$ moi $3.10^4$, (2) $AV_{1.0}CMVrGax$ moi $10^4$, (3) 3528 moi $10^4$, (4) 3528 moi $3.10^3$, (5) 3528 moi 300, (6) 3569 moi $3.10^3$, (7) 3569 moi 300, (8) 3570 moi $10^4$ and (9) 3570 moi $3.10^3$.

Figure 7:
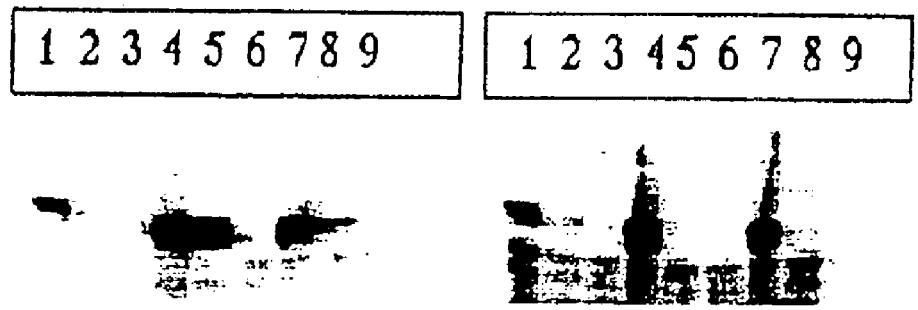
Figure 8A:
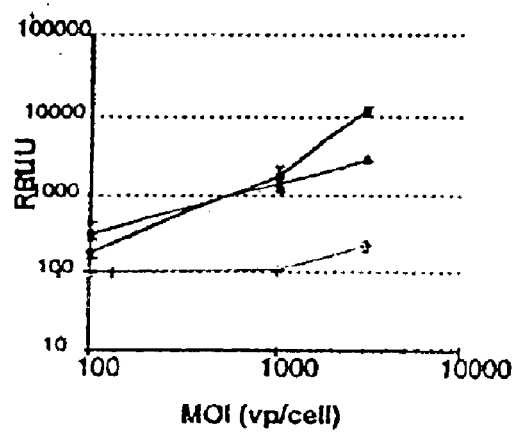
FIGS. 8A to 8C and 9: Infection of Hs578T with different targeted viruses.
Figure 8B:
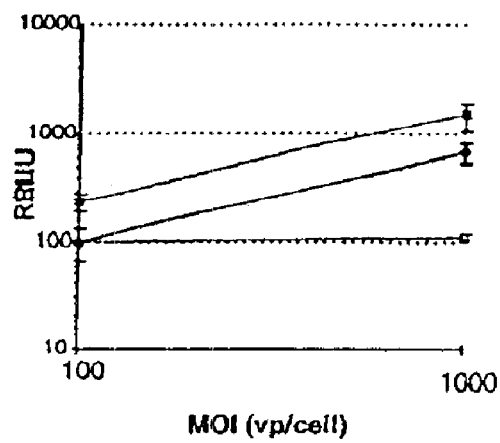
Figure 8C:
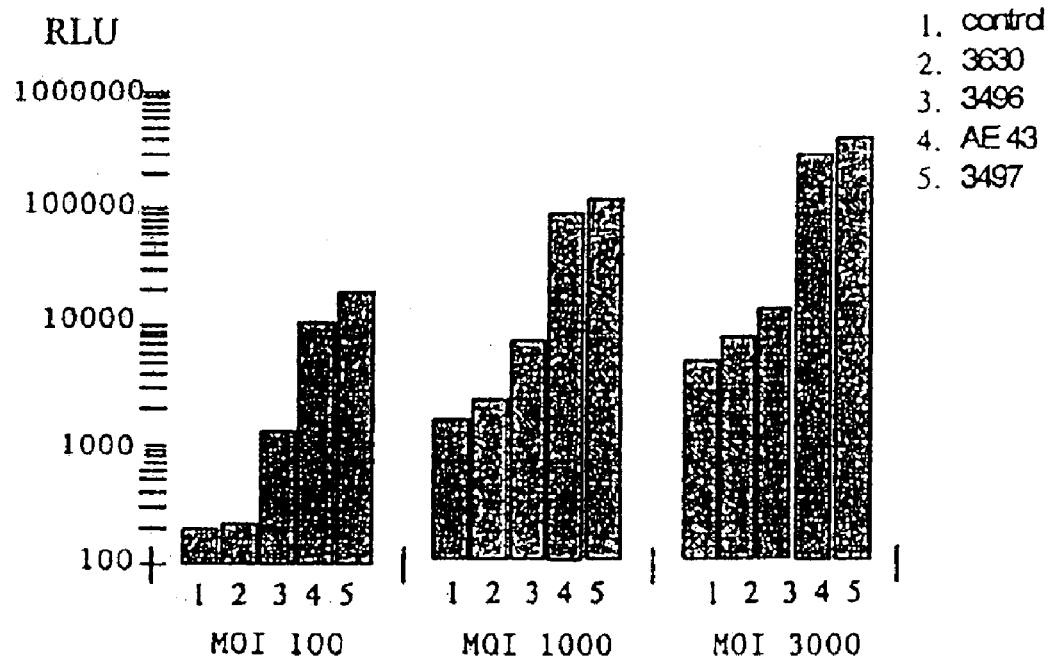
Figure 9:
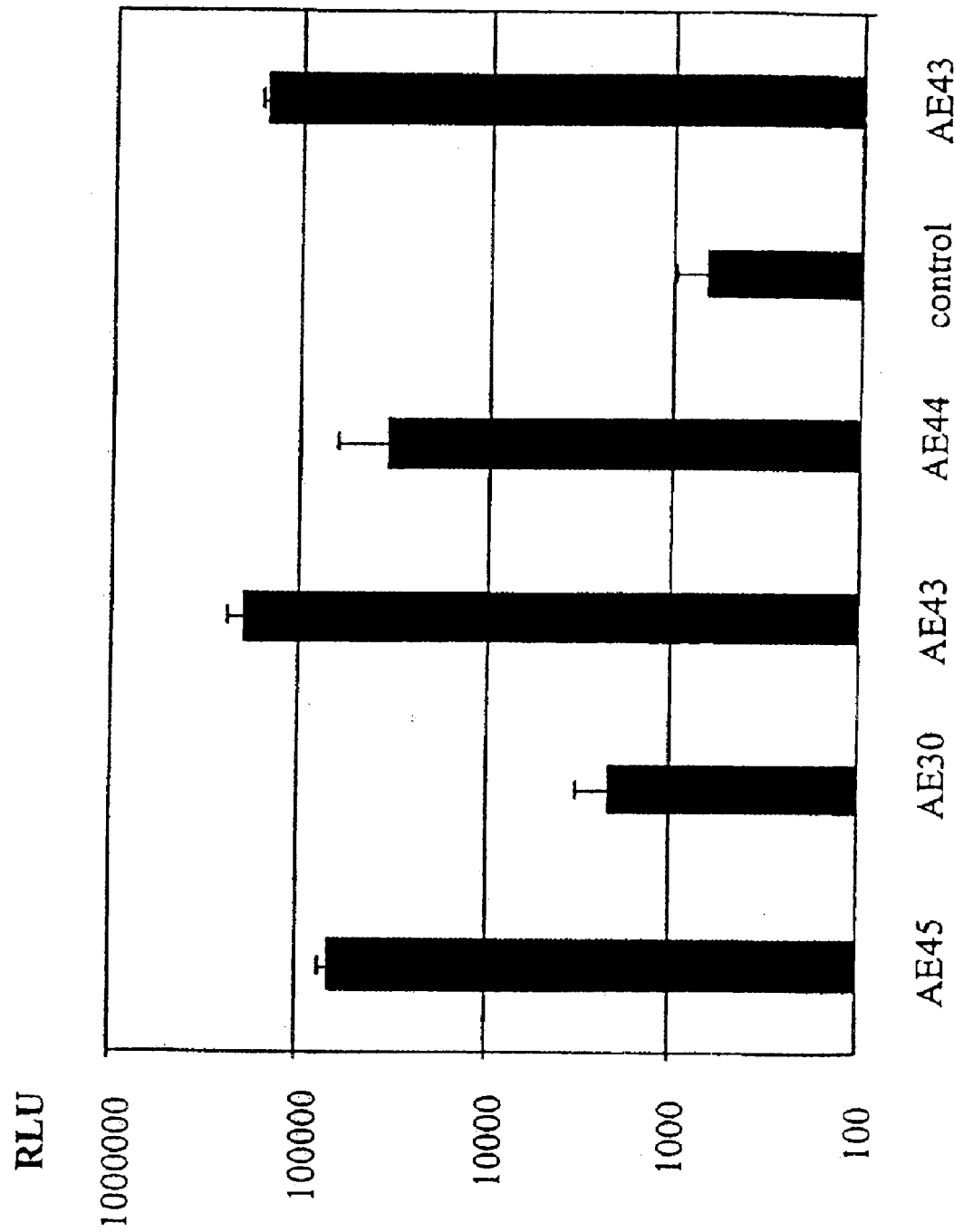

FIG. 7 ilustrates the Gax expression after human SMC infection with targeted adenovirus. Protein extracts were prepared 24 hours after infection at the indicated moi (VP/cell).

Left panel: (1) $AV_{1.0}CMVrGax$ moi $3.10^4$ (2) $AV_{1.0}CMVhGax$ moi $3.10^4$, (3) $AV_{1.0}CMVhGax$ moi $3.10^3$, (4) 3528 moi 3000, (5) 3528 moi 300, (6) 3528 moi 30, (7) 3569 moi 3000, (8) 3569 moi 300, (9) 3569 moi 30

Right panel: (1) $AV_{1.0}CMVrGax$ moi $3.10^4$ (2) $AV_{1.0}CMVhGax$ moi $3.10^4$, (3) $AV_{1.0}CMVhGax$ moi $3.10^3$, (4) 3570 moi 3000, (5) 3570 moi 300, (6) 3570 moi 30, (7) 3629 moi 3000, (8) 3629 moi 300, (9) 3629 moi 30

Gax expression was also evidenced by FACS analysis after infection of hSMC at different moi. Even if the sensitivity of this technique is much higher than Western blotting, the results correlate with Western experiments and show the relative superiority of viruses 3528 and 3569 over 3570 and 3629 in their ability to efficiently transduce hSMC, as ilustrates on the following table 25.

TABLE 25

FACS analysis of Gax expression after infection of human SMC. (% of Gax expressing cells was determined 24 hours after infection.)

| Virus | 10000 VP/cell | 1000 VP/cell | 100 VP/cell |
|---|---|---|---|
| $AV_{1.0}CMVrGax$ | 100% | 52% | — |
| $AV_{1.0}CMVhGax$ | 86% | 8% | — |
| 3528 | nd | 99% | 99% |
| 3569 | nd | 99% | 99% |
| 3570 | nd | 99% | 8% |
| 3629 | nd | 99% | 18% |

Example 9

In Vitro Evaluation of Targeted Viruses in Human Tumoral Cells

Hs578T cells (human breast tumor cells) are quire refractory to Ad5 infection most likely because they express limiting amounts of the virus receptor at their cellular surface. In practice, an moi as high as $10^5$ VP/cell is necessary to infect 50% of the cells. They were tested for their ability to be transduced by a panel of capsid-modified vectors.

FIGS. 8A, 8B, 8C and 9 illustrate infection of Hs578T with different targeted viruses. Cell extracts were prepared 48 h post infection. The data show that AE43, AE44, AE45 or 3497 are very efficient in transducing this cell type.

Figure 10:
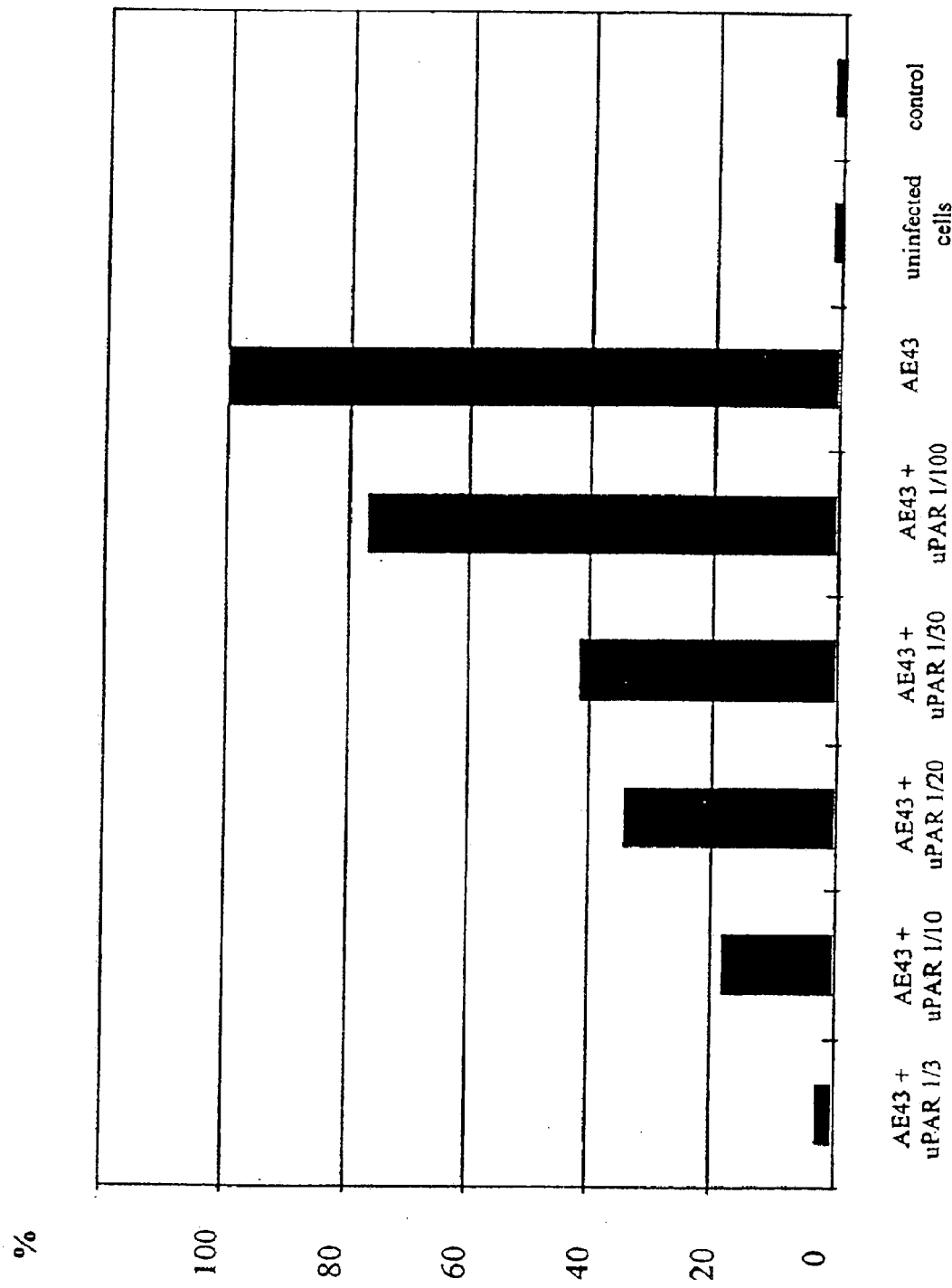
FIG. 10: Infection of Hs578T with virus AE43 preincubated with increasing doses of soluble uPAR.
Figure 11:
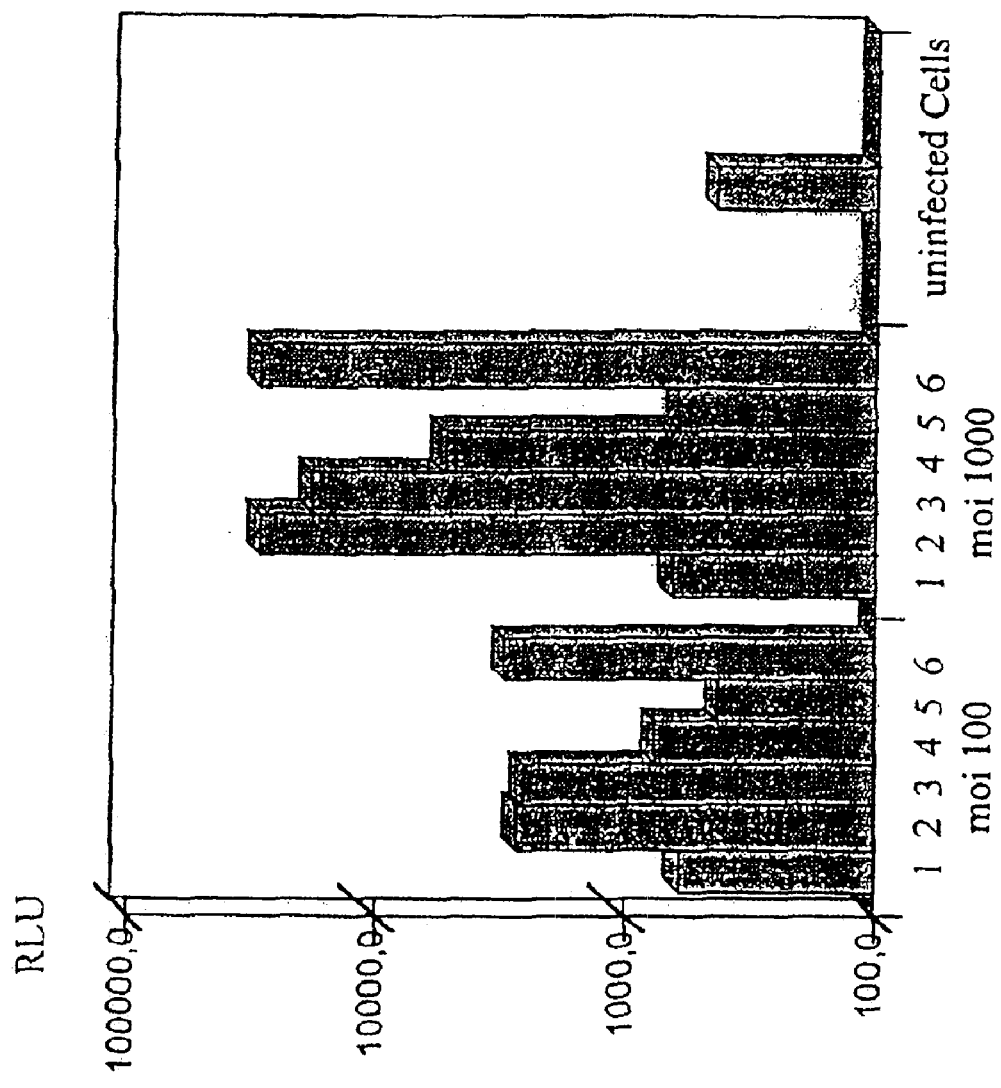
FIG. 11: Infection of Hs578T with virus AE43 preincubated with increasing doses of soluble uPAR or soluble knob.

The pathway of infection of AE43 was analyzed by competition with soluble knob fiber or soluble uPAR (FIGS. 10 and 11).

In FIG. 10, AE43 was preincubated with soluble uPAR before infection of Hs578T. Cell extracts were prepared 48 h post infection.

In FIG. 11, AE43 was preincubated with soluble uPAR (10 $\mu$g/2 $10^8$ VP) or soluble knob (100 $\mu$g/ml) before infection of Hs578T. Cell extracts were prepared 48 h post infection.

The results indicate that AE43 does not enter the cell via the classical knob-CAR pathway but rather uses a uPAR-dependent pathway for entry.

Figure 12:
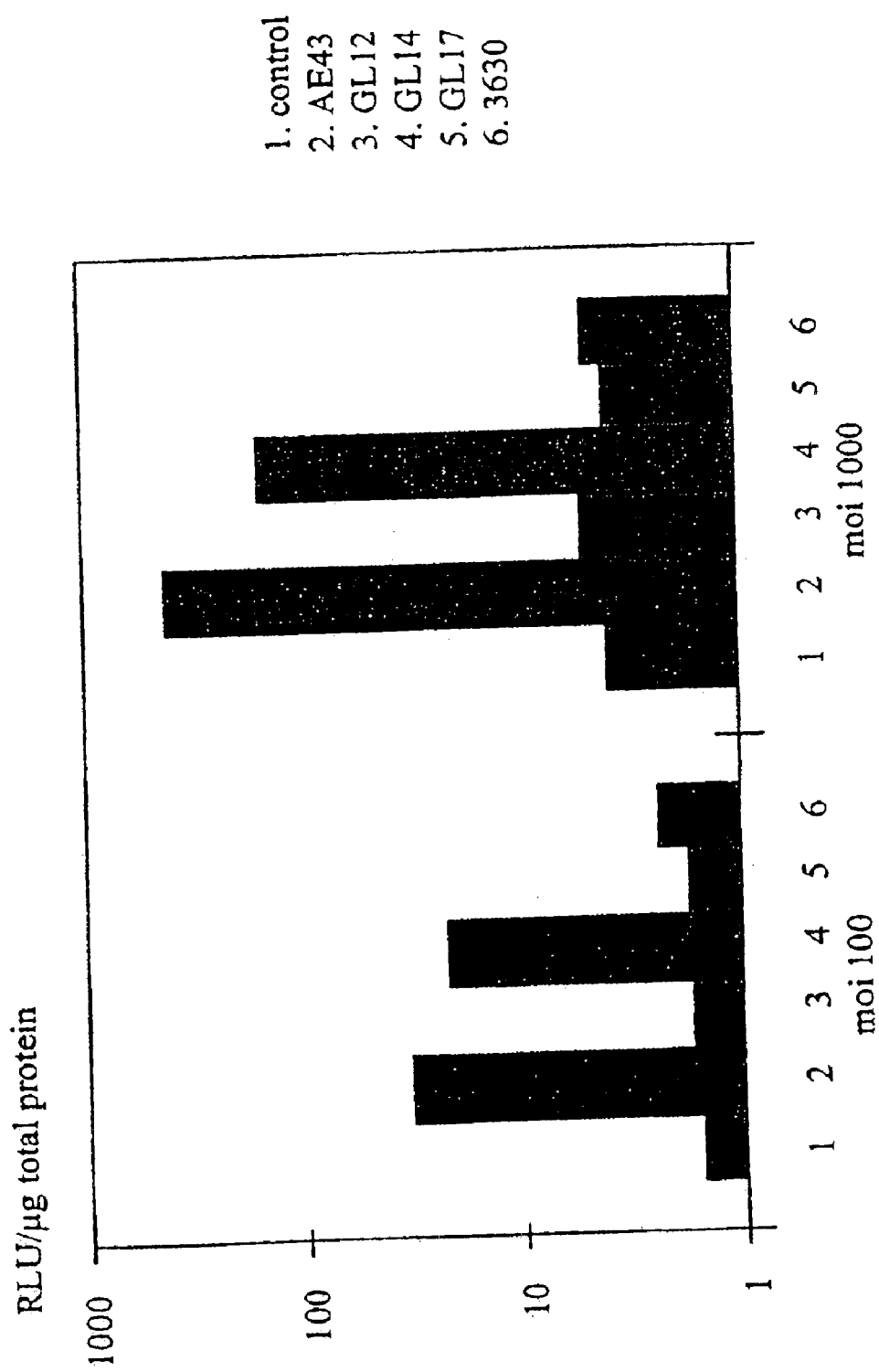
FIG. 12: Infection of Hs578T with Vn4 containing viruses.

Finally, Vn4-containing viruses 3630, GL12, GL14 or GL17 were compared to AE43 in their ability to transduce Hs578Tcells. As shown in FIG. 12 at 48 h post infection, the nature of the connecting linkers indeed can greatly influence the efficacy with which a binding peptide inserted in the HI loop interacts with its specific receptor at the cellular surface.

Example 10

In Vitro Evaluation of Targeted Viruses in Murine Tumoral Cells

Figure 13:
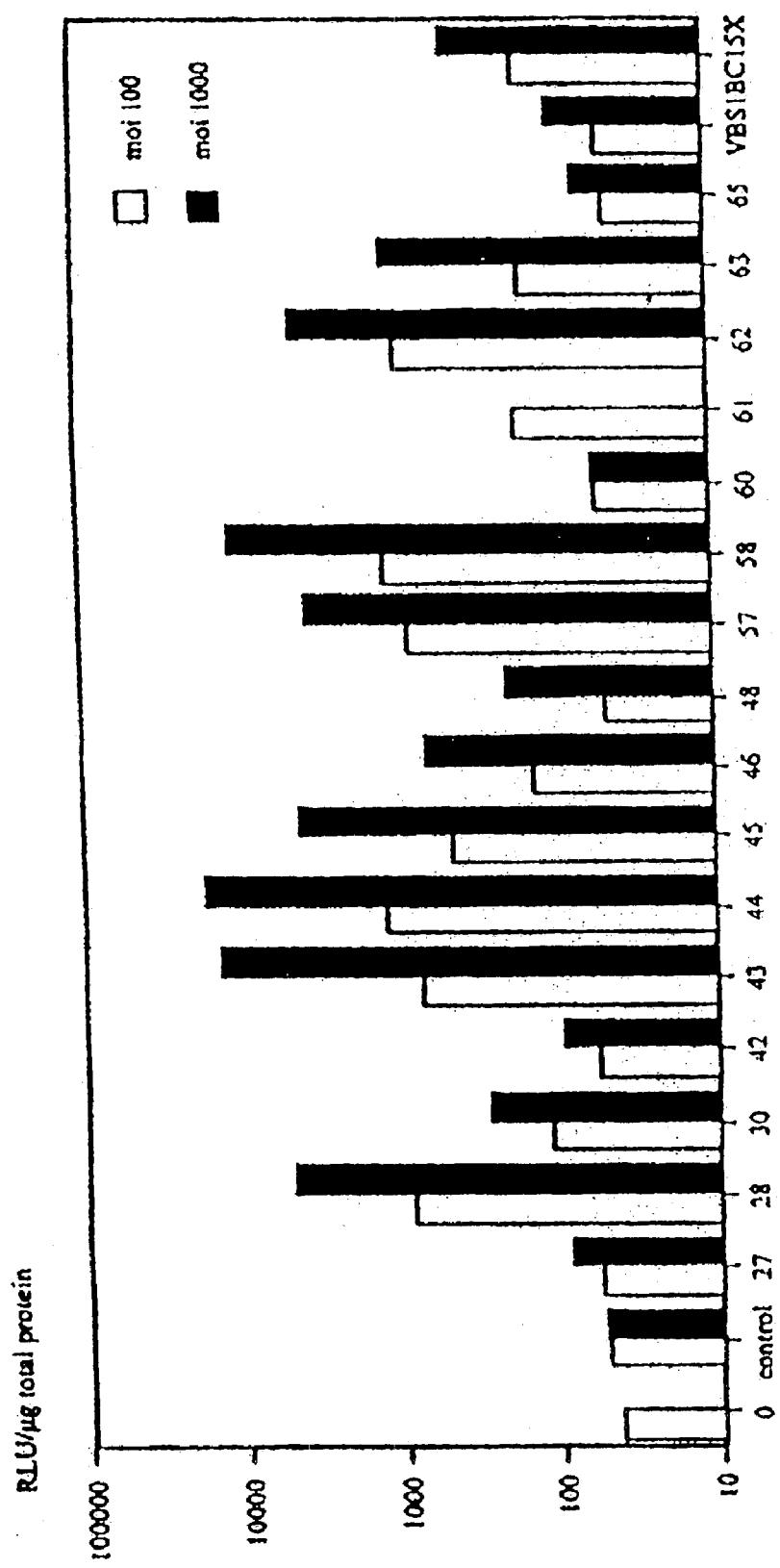
FIG. 13: Infection of NIH-3T3 with a large range of targeted viruses.

Murine NIH-3T3 cells are very resistant to Ad5 infection as more than 100000 VP/cell is necessary to infect 50% of the cells. They were tested for their ability to be transduced by a panel of capsid-modified viruses. Cell extracts were prepared 48 h post infection. FIG. 13 include data from a representative experiment which demonstrate that AE28, AE43, AE44, AE58, AE57 or AE62 are particularly efficient. Also, and importantly, AE63 (short fiber, RGD-2C in hexon) was shown to be partially able to rescue the defect associated with its short-shafted control virus (vBS1; no insertion in hexon). Capsid modifications that impair the native entry pathway (e.g., fibers displaying short shafts) can therefore be combined with capsid modifications that provide an additional, CAR-independent, pathway for infection.

The pathway of infection of AE43 and BC15X was analyzed by competition with soluble uPAR (FIGS. 14A and 14B). In FIGS. 14A and 14B, viruses BC15X (A) and AE43 (B) were preincubated with increasing doses of soluble uPAR before incubation with cells (moi 1000 and 200 VP/cell, respectively). Cells were then washed and further incubated at 37° C. for 48 h before preparation of cell extracts. These and other data indicate that these viruses use uPAR for infection.

Example 11

In Vivo Evaluation of Targeted Viruses in a Restenosis Rabbit Model

The in vivo evaluation of some of the targeted viruses was performed in a an atheromatous double injury rabbit model, which is a good model for restenosis: transfer takes place in atheromatous iliac arteries; rabbits are fed 120 g daily of 1% cholesterol diet and at 3 weeks a first injury by balloon angioplasty is performed with a 2.5 mm diameter Nycomed balloon catheter. One week later, adenoviral gene transfer is performed.

Microscopic quantification of SMC staining for $\beta$-galactosidase was used to define the efficacy of gene transfer (histochemical analysis). Briefly, 32 sections/artery were examined and XGal-positive cells were counted. The data are presented as the highest score among the 32 sections for one artery. Results are presented in the following table 26.

TABLE 26

| In vivo evaluation of targeted viruses in a restenosis rabbit model | | |
|---|---|---|
| Virus injected | $10^{11}$ VP/artery | $5.10^{11}$ VP/artery |
| Control virus | positive arteries: 0/8 | positive arteries: 7/10<br>*6 arteries with <30 stained cells<br>*1 artery with 200–400 stained cells |
| AE57<br>RGD-2C in hexon | positive arteries: 0/6 | positive arteries: 2/2<br>*2 arteries with <30 stained cells |
| AE43<br>VN4 in HI fiber | positive arteries: 5/6<br>*2 arteries with <30 stained cells<br>*2 arteries with 30–100 stained cells<br>*1 artery with >400 stained cells | |
| BC15X<br>VN4<br>at C-ter fiber | positive arteries: 4/4<br>*1 artery with <30 stained cells<br>*1 artery with 30–100 stained cells<br>*1 artery with 100–200 stained cells<br>*1 artery with 200–400 stained cells | |

These data indicate that adenoviruses AE43 and BC15X transduce arterial wall with a dramatically increased efficacy as compared to their unmodified control.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. An adenovirus wherein about 13 amino acids from the hexon HVR5 loop, corresponding to about amino acid residue 269 to about amino acid residue 281 of adenovirus serotype 5 (Ad5), is replaced with a targeting sequence flanked by connecting amino acid spacers so as to functionally display the targeting sequence's binding specificity at the capsid surface.

2. The adenovirus according to claim 1, wherein the spacers comprise an amino acid selected from the group consisting of glycine, serine, threonine, alanine, cysteine, aspartate, asparagine, methionine and proline.

3. The adenovirus according to claim 2, wherein the spacers comprise an amino acid selected from the group consisting of glycine and serine.

4. The adenovirus according to claim 2, wherein the first amino acid in at least one of the spacers is an amino acid selected from the group consisting of glycine, serine, threonine, alanine, cysteine, aspartate, asparagine, methionine and proline.

5. The adenovirus according to claim 4, wherein the first amino acid in the spacers is an amino acid selected from the group consisting of glycine, serine, threonine, alanine, cysteine, aspartate, asparagine, methionine and proline.

6. The adenovirus according to claim 5, wherein the first amino acid in at least one of the spacers is a glycine residue.

7. The adenovirus according to claim 5, wherein the first amino acid of the spacers is a glycine residue.

8. The adenovirus according to claim 2, wherein at least one of the spacers is a dipeptide.

9. The adenovirus according to claim 8, wherein at least one of the spacers is a Gly-Ser dipeptide.

10. The adenovirus according to claim 1, wherein the targeting sequence is a ligand epitope for a urokinase-type plasminogen activator receptor (UPAR).

11. The adenovirus according to claim 10, wherein the targeting sequence is selected from the group consisting of LNGGTCVSNKYFSNIHWCN (SEQ ID NO: 1); LNGGTAVSNKYFSNIHWCN (SEQ ID NO: 2); AEPMPHSLNFSQYLWT (SEQ ID NO: 3); AEPMPHSLNFSQYLWT (SEQ ID NO: 4); RGHSRGRNQNSR (SEQ ID NO: 5); and NQNSRRPSRA (SEQ ID NO: 6).

12. The adenovirus according to claim 9 wherein wherein the targeting sequence including the spacers, is selected from the group consisting of:
a) gly-ser-LNGGTCVSNKYFSNIHWCN-gly-ser (SEQ ID NO: 7);
b) gly-ser-LNGGTAVSNKYFSNIHWCN-gly-ser (SEQ ID NO: 8);
c) gly-ser-AEPMPHSLNFSQYLWT-gly-ser (SEQ ID NO: 9);
d) gly-ser-AEPMPHSLNFSQYLWT-gly-ser (SEQ ID NO: 10);
e) gly-ser-RGHSRGRNQNSR-gly-ser (SEQ ID NO: 11);
f) gly-ser-NQNSRRPSRA-gly-ser (SEQ ID NO: 12);
g) gly-ser-CDCRGDCFC-gly-ser (SEQ ID NO: 13);
h) gly-ser-DCRGDCF-gly-ser (SEQ ID NO: 14); and
i) gly-ser-KKKKKKK-gly-ser (SEQ ID NO: 15).

13. The adenovirus according to claim 1, which is derived from human adenovirus serotype.

14. The adenovirus according to claim 13, which is derived from human adenovirus subgroup C.

15. The adenovirus according to claim 14, which is derived from human adenovirus serotype 5.

16. The adenovirus according to claim 1, wherein the fiber protein is modified to have a fiber shaft that is shorter than a wild-type fiber shaft.

17. The recombinant adenovirus according to claim 16, wherein the fiber shaft has been shortened by an in-frame deletion.

18. The recombinant adenovirus according to claim 16, wherein the fiber shaft has been shortened by replacement with a shaft from another serotype.

19. The recombinant adenovirus according to claim 16, wherein the fiber shaft is from human subgroup C (Ad2 or Ad5) and has been shortened by replacement with a shaft from serotype 3 (Ad3).

20. The adenovirus according to claim 16, wherein the fiber shaft contains repeats 1 to 3 and 17 to 22 of Ad5; repeats 1 to 3 and 20 to 22 of Ad5; or an adenovirus serotype 3 (Ad3) shaft.

21. An adenovirus wherein at least a part of the hexon HI loop is replaced with a targeting sequence flanked by connecting amino acid spacers so as to functionally display the targeting sequence's binding specificity at the capsid surface.

22. The adenovirus according to claim 21, wherein about 6 to 17 amino acids from the hexon HI loop are replaced.

23. The adenovirus according to claim 22, wherein no more than 11 amino acids from the hexon HI loop are replaced.

24. The adenovirus according to claim 23, wherein about 11 amino acids from the hexon HI loop, corresponding to about amino acid residue 538 to about amino acid residue 548 of adenovirus serotype 5 (Ad5), are replaced.

25. The adenovirus according to claim 24, wherein the spacers comprise an amino acid selected from the group consisting of glycine, serine, threonine, alanine, cysteine, aspartate, asparagine, methionine and proline.

26. The adenovirus according to claim 25, wherein the spacers comprise an amino acid selected from the group consisting of glycine and serine.

27. The adenovirus according to claim 24, wherein the first amino acid in at least one of the spacers is an amino acid selected from the group consisting of glycine, serine, threonine, alanine, cysteine, aspartate, asparagine, methionine and proline.

28. The adenovirus according to claim 27, wherein the first amino acid in the spacers is an amino acid selected from the group consisting of glycine, serine, threonine, alanine, cysteine, aspartate, asparagine, methionine and proline.

29. The adenovirus according to claim 28, wherein the first amino acid in at least one of the spacers is a glycine residue.

30. The adenovirus according to claim 29, wherein the first amino acid in at least one of the spacers is a glycine residue.

31. The adenovirus according to claim 24, wherein the first amino acid in at least one of the spacers is a tripeptide.

32. The adenovirus according to claim 31, wherein the first amino acid in at least one of the spacers is a Gly-Ser-Ser tripeptide.

33. The adenovirus according to claim 24, wherein the targeting sequence is a ligand epitope for a urokinase-type plasminogen activator receptor (UPAR).

34. The adenovirus according to claim 33, wherein the targeting sequence is selected from the group consisting of LNGGTCVSNKYFSNIHWCN (SEQ ID NO: 1); LNGGTAVSNKYFSNIHWCN (SEQ ID NO: 2); AEPMPHSLNFSQYLWT (SEQ ID NO: 3); AEPMPHSLNFSQYLWT (SEQ ID NO: 4); RGHSRGRNQNSR (SEQ ID NO: 5); and NQNSRRPSRA (SEQ ID NO: 6).

35. The adenovirus according to claim 24 the targeting sequence including the spacers, is selected from the group consisting of:

A) gly-ser-LNGGTCVSNKYFSNIHWCN-gly-ser (SEQ ID NO: 7);
B) gly-ser-LNGGTAVSNKYFSNIHWCN-gly-ser (SEQ ID NO: 8);
C) gly-ser-AEPMPHSLNFSQYLWT-gly-ser (SEQ ID NO: 9);
D) gly-ser-AEPMPHSLNFSQYLWT-gly-ser (SEQ ID NO: 10);
E) gly-ser-RGHSRGRNQNSR-gly-ser (SEQ ID NO: 11);
F) gly-ser-NQNSRRPSRA-gly-ser (SEQ ID NO: 12):
G) gly-ser-CDCRGDCFC-gly-ser (SEQ ID NO: 13);
H) gly-ser-DCRGDCF-gly-ser (SEQ ID NO: 14); and
I) gly-ser-KKKKKKK-gly-ser (SEQ ID NO: 15).
J) ser-ser-RGHSRGRNQNSRRPSRA-gly-ser (SEQ ID NO: 143);
K) tyr-ser-glu-RGHSRGRNQNSR-gly-ser (SEQ ID NO: 144);
L) tyr-gln-glu-RGHSRGRNQNSR-gly-ser (SEQ ID NO: 145);
M) ser-ser-ser-RGHSRGRNQNSR-gly-ser (SEQ ID NO: 146);
N) ser-ser-RGHSRGRNQNSR-gly-gly (SEQ ID NO: 147).

36. The adenovirus according to claim 24, which is derived from human adenovirus serotype.

37. The adenovirus according to claim 36, which is derived from human adenovirus subgroup C.

38. The adenovirus according to claim 37, which is derived from human adenovirus serotype 5.

39. The adenovirus according to claim 24, wherein the fiber protein is modified to have a fiber shaft that is shorter than a wild-type fiber shaft.

40. The adenovirus according to claim 39, wherein the fiber shaft has been shortened by an in-frame deletion.

41. The adenovirus according to claim 39, wherein the fiber shaft has been shortened by replacement with a shaft from another adenovirus serotype.

42. The adenovirus according to claim 41, wherein the fiber shaft is from human subgroup C (Ad2 or Ad5) and has been shortened by replacement with a shaft from serotype 3 (Ad3).

43. The adenovirus according to claim 39, wherein the fiber shaft contains repeats 1 to 3 and 17 to 22 of Ad5; repeats 1 to 3 and 20 to 22 of Ad5; or an adenovirus serotype 3 (Ad3) shaft.

44. An adenovirus hexon comprising a deletion of about 13 amino acids from the HVR5 loop corresponding to about amino acid residue 269 to about amino acid residue 281 of adenovirus serotype 5 (Ad5) and an insertion at the site of the deletion of a targeting peptide sequence connected by a first spacer at the N-terminus and a second spacer at the C-terminus of the targeting peptide sequence.

45. An adenovirus hexon protein comprising a deletion of about 11 amino acids from the HI loop corresponding to about amino acid residue 538 to about amino acid residue 548 of adenovirus serotype 5 (Ad5) and an insertion at the site of the deletion of a targeting peptide sequence connected by a first spacer at the N-terminus and a second spacer at the C-terminus of the targeting peptide sequence.

46. A pharmaceutical composition comprising an adenovirus vector of claim 1, and an efficient quantity of a pharmaceutically active excipient.

* * * * *